(12) United States Patent
Delfour et al.

(10) Patent No.: US 8,116,987 B2
(45) Date of Patent: Feb. 14, 2012

(54) METHODS FOR THE IDENTIFICATION OF MICRORNA AND THEIR APPLICATIONS IN RESEARCH AND HUMAN HEALTH

(75) Inventors: Olivier Delfour, Toulouse (FR); Jerome Ciuti, Toulouse (FR); Florent Denoual, Toulouse (FR); David Vilanova, Toulouse (FR); Bernard Michot, Pern (FR)

(73) Assignee: Cepheid, Sunnyvale, CA (US)

( * ) Notice: Subject to any disclaimer, the term of this patent is extended or adjusted under 35 U.S.C. 154(b) by 592 days.

(21) Appl. No.: 12/092,952

(22) PCT Filed: Nov. 8, 2006

(86) PCT No.: PCT/EP2006/068246
§ 371 (c)(1),
(2), (4) Date: Sep. 11, 2008

(87) PCT Pub. No.: WO2007/054520
PCT Pub. Date: May 18, 2007

(65) Prior Publication Data
US 2009/0062135 A1 Mar. 5, 2009

(30) Foreign Application Priority Data
Nov. 8, 2005 (EP) .................................... 05292359

(51) Int. Cl.
*G01N 7/00* (2006.01)
(52) U.S. Cl. ................ 702/19; 702/20; 703/11; 703/12; 707/700; 536/24.5
(58) Field of Classification Search .................... 702/19, 702/20; 703/11, 12; 707/700; 536/24.5
See application file for complete search history.

(56) References Cited

OTHER PUBLICATIONS

Ng et al. Bioinformatics 2007 23 (11) 1321-1330.*
Bentwich, I. et al., "Identification of Hundreds of Conserved and Nonconserved Human MIcroRNAs," Jul. 2007, Nature Genetics, Nature America, vol. 37, No. 7, pp. 766-770.
Berezikov, Eugene et al., "Phylogenetic Shadowing of Computational Identification of Human MicroRNA Genes," Jan. 14, 2005, Cell, vol. 120, No. 1, pp. 21-24.
Grad Y. et al., "Computational and Experimental Identification of C. elegans MicroRNAs," May 1, 2003, Molecular Cell, Cell Press, vol. 11, No. 5, pp. 1253-1263.
Lai E. C. et al., "Computational Identification of Drosophila MicroRNA Genes," 2003, Genome Biology (Online), vol. 4, No. 7, p. R42, XP002370305.
Llave Cesar et al., "Endogenous and silencing-associated small RNAs in plants" Jul. 2002, Plant Cell, American Society of Plant Physiologists, Rockville, MD, US vol. 14, No. 7, pp. 1605-1619.
Sewer, Alain et al, "Identification of Clustered MicroRNAs Using an Ab Initio Prediction Method," Nov. 7, 2005, BMC Bioinformatics, vol. 6, pp. 1-15.
Smalheiser, Neil R., et al., "Mammalian MicroRNAs Derived from Genomic Repeats," Jun. 2005, vol. 21, No. 6, pp. 322-326, XP004911546.
Xie, Xiaohui et al., "Systematic Discovery of Regulatory Motifs in Human Promoters and 3' UTRs by Comparison of Several Mammals," Mar. 17, 2005, Nature, vol. 434, No. 7031, pp. 338-345.

* cited by examiner

*Primary Examiner* — Mary Zeman
(74) *Attorney, Agent, or Firm* — Kilpatrick Townsend & Stockton LLP

(57) ABSTRACT

The present invention concerns a method for prediction and identification of microRNA precursors (pre-microRNA) and microRNA molecules using data processing programs and databases. The invention also pertains to the isolated form of these pre-microRNAs, microRNA molecules and derived nucleic acids there of. The invention also relates to recombinant vector, host cell, support, pharmaceutical composition or kit comprising such microRNA molecules or there of derivated molecules. The invention also applies to the use of such microRNA molecules and/or their identified targets in research, prognostic, diagnostic tools/methods as well as for therapeutic applications.

29 Claims, 13 Drawing Sheets

True situation: 1 sequence in Human (query) has 3 occurrences in Mouse (hit)

3 blast report obtained (3HSPs)

```
5'      CAG       GA  A  GAGAA-       UU      C  A
   AUGG     AGAUAUU  CAU GU      AACA   GCCUU    A
   UACC     UCUGUAA  GUG CA      UUGU   CGGGA    C
3'      AGA       A-  A  AAACAG       UU      UAA
```

Secondary structure of SEQ ID 7805

```
5' G     -     AG    ACA  ACC         A------     UGCU
    CUGGCUCC UGCUC AGUG  GC  CUGUGG           GUC      G
    GACCGAGG ACGAG UCAC  CG  GACACC           CAG      G
3'       U     G-    CC-  A--         ACCAAUC     UCAU
```

Secondary structure of SEQ ID 7806

```
5' A       CAC-- --        UG         AU A  C   UU
    GUGGGGG     GU  UCAAGAA   CUAAUGA  U  U  AG   U
    UACCCUC     CG  AGUUCUU   GAUUACU  G  A  UU   U
3'        CAAAA AU        UA         CC A  U   C
```

Secondary structure of SEQ ID 7807

```
5'    C   C  - U  - -    C              - G
   GG UGG CAG GC CCGC CC CCGG  CCUCCCUGCGC  CC  G
   CC ACC GUC CG GGCG GG GGCU  GGAGGGACGCG  GG  C
3' C  -   C   A  - A  A  -              U  C
```

Secondary structure of SEQ ID 7808

```
5' C    A  A-  --            -----       AAC
    UCUCU CC  CCA  AAAUAAAUU        CAAUUACU   U
    AGAGA GG  GGU  UUUAUUUAA        GUUAAUGA   U
3'      C  GA  UC            UGGGC        -GU
```

Secondary structure of SEQ ID 7809

```
5'    - G         CAG    -  AAUG    AAG    G
   CAU GU AUUUCUGCC   UGCUC UG   UCA    UGAA  A
   GUA CA UGAGGGCGG   AUGGG AC   AGU    ACUU  A
3'    U A         CAA    C  GA--    A--    A
```

Secondary structure of SEQ ID 7810

FIG. 10

```
5'      G UA    U    U      AA         G U     C
   GCCU C  AUGG UCUAC GCUUUG  GGUUCCA G CUGUG -
   CGGA G  UGUC AGGUG UGAGGAC CCAGGGU U GACAC A
3'      G --    U    -      C-         G -     G
```

Secondary structure of SEQ ID 7811

```
5'          -       AAU  GU----     AA
   ACUUAG AGGAGUGACA    UUG     ACUUAAA A
   UGAAUC UCUUCACUGU    AAC     UGGAUUU U
3'          A       CCC  AAAAAU     -A
```

Secondary structure of SEQ ID 7812

```
5' C    CAG       AGCAAC       UA A--   -  AAA
   CCUCC    UUCCCAU    UGGGCUG GC   GC CAG   C
   GGAGG    AGGGGUG    GCCCGGU CG   CG GUU   U
3'    AA-      GAGUCA       GA ACC  A  AGU
```

Secondary structure of SEQ ID 7813

```
5'      U UGC    CUCU     GCC      UU    CA -UG
   GGAGA G  GCCCC    GCCAC   CCCACC  CCUGG GG  G
   CCUCU C  UGGGG    CGGUG   GGGUGG  GGACC CC  U
3'      - UU-    C---     AA-      UG    A- GGG
```

Secondary structure of SEQ ID 7814

```
5'    A UG   --   C-    A  C  -   U-
   CUU GGGG GGGG AGCC UGUU GCC UG UAAA  A
   GAG UCCC UCUC UCGG ACAA UGG GC AUUU  A
3'    -  UG   GG   UA    G  A  A   GA
```

Secondary structure of SEQ ID 7815

```
5'           C----     CA -    C     -  -CA
   AGUGCUUUU      UGUAA  GU CAUUUGA AUUUAAU AUAC   U
   UCACGAAAA      ACGUU  UA GUAAAUU UAAAUUA UAUG   A
3'           UCUUA     UA C    -     U  UUA
```

Secondary structure of SEQ ID 7816

FIG. 10 (continued)

```
5'      AA       G   GAUUAG  GU    CA    --    GA
   GUGAAG  UGCAGGCAG  UUGU       AG  GAGC  GUU   CCU  U
   CAUUUC  AUGUCCGUC  AAUA       UC  CUCG  UAA   GGG  U
3'      G-       A    A-----  GU    AA    UU    UG
```

Secondary structure of SEQ ID 7817

```
5'GCA          AA   C         U    -UGCU
     UCAUUAGCU  CA  AGGGAAAG  GAAA       G
     AGUAGUCGA  GU  UUCUUUUU  CUUU       U
3'--G          AC   C         -    UCAAU
```

Secondary structure of SEQ ID 7818

```
5'              C   A---        GA    --     CA
   CCUUUUGAGUGGA  CUG     AGGGUUUU  CCU   UCUU   G
   GGAG     UCACCU  GAC   UUCCAAAA  GGA   GGAA   G
3'         ---     U   AAAA        AC    AC     -A
```

Secondary structure of SEQ ID 7819

```
5'       --          UU  U  UCU  A  -   GAAA        -C
   CAUUUG  CUUGAUUAA  AC  GC   GA  ACC  CUU   ACAGA  A
   GUAGAC  GAGCUAAUU  UG  UG   CU  UGG  GAA   UGUCU  U
3'       AG          --  U--  A   U    ----        GG
```

Secondary structure of SEQ ID 7820

```
5'        AC    AG  -  -         G     ACG    AU
   GAGCUGC  AGAC  C  UG  CAAUUCAU  GGCG    CUG  U
   CUCGACG  UCUG  G  AC  GUUAGGUA  UCGC    GAC  G
3'        --    GG  U  G         -     AAA    -C
```

Secondary structure of SEQ ID 7821

FIG. 10 (continued)

METHODS FOR THE IDENTIFICATION OF MICRORNA AND THEIR APPLICATIONS IN RESEARCH AND HUMAN HEALTH

CROSS REFERENCE TO RELATED APPLICATIONS

This application is the U.S. National Stage entry of International Application No. PCT/US2006/068246, filed Nov. 8, 2006, which claims priority from and the benefit of European Application No. 05292359.6, filed on Nov. 8, 2005, the entire contents of both aforementioned applications are hereby incorporated herein by reference.

1. Field of the Invention

This invention generally relates to bioinformatics, and more particularly to the identification of RNA sequences, particularly microRNA precursor candidates.

2. Background of the Invention

The development of multi-cellular and multi-tissue organisms requires specific and coordinated control involving complex regulatory mechanisms that target every aspect of gene expression. NpcRNA (non protein coding ribonucleic acids) such as tRNA and rRNA are known essential regulators of gene expression and protein synthesis. MicroRNA (miRNA) constitute a vast family of non-protein coding RNA that play critical regulatory functions in numerous biological processes and hold the key of many important aspects of human health. For example, microRNAs orchestrate many aspects of cell, tissue and organism development. They also play key roles in the regulation of fundamental cellular mechanisms (Brennecke J and al., 3003; Chen C Z, 2004; Esau C and al., 2004; Yekta S, and al., 2004). Most microRNAs are submitted to two types of regulations: a temporal regulation which is a function of different cell growth stages, differentiation and development, and a spatial regulation. Indeed, they show specific expression patterns in each cellular or tissue type (Reinhart B J., 2000).

Besides the detection and profiling of miRNA genes, deciphering their function is also particularly challenging. With very few exceptions, their specific functions are unknown. MicroRNAs do not act alone, but act in combination to cooperatively regulate a definite biological process. This mode of action is the one generally referred to when talking about the so-called "microRNA code". The miRNAs that belong to a "functional family" need to be identified, and their "true" mRNA targets discerned from amongst thousands of possibilities. Being timely and spatially regulated, their discovery requires high-throughput methods, like microarrays, in order to find novel miRNAs, which are specifically expressed in particular cell-types, tissues and under different physiological conditions.

Additionally, the complete set of microRNA which are expressed in different organisms is unknown. Thus, one main challenge today consists in identifying the complete set of microRNAs. It appears that only the tip of the iceberg of the microRNA world is known. Contrary to what was believed for a long time, recent studies show that a great number of microRNA remain to be identified.

Today, it is a major challenge to identify novel microRNAs, and there is a growing interest of life science industries in microRNA. Indeed, the exhaustive knowledge of microRNA will make it possible to identify mechanisms of regulation, that will help to better understand the gene and protein regulation networks, and to discover new molecular biomarkers associated with cell development and many different diseases.

The principal method used until now to discover new microRNAs consists in their detection and their quantification by biological experiments using approaches and strategies of molecular biology, such as RNA extraction, amplification, cloning, gel electrophoresis, hybridization, and sequencing. However, the large majority of the microRNA are controlled in a space-time dependent manner, where they are mostly only slightly expressed. Thus, many escape detection by these conventional biochemical and genetic approaches.

Bioinformatic approaches have emerged as powerful alternatives. Predictive bioinformatics have provided many discoveries, obtained through combination of experimental and computational approaches. Nevertheless, these approaches require the development of new strategies. The identification of microRNA is indeed especially complex because of their very short size and their great variability in sequence. There is no evident specific sequence "signature" like for protein coding genes. The nature of their structural constraint is mainly defined by the complementarities with their mRNA targets, and not by any evident structural constraints within the mature miRNA itself. Thus, most of the computational methods are based on a search for their precursors, which fold into a variable and irregular stem-loop structures (hairpin secondary structures).

A first work in 2003 (Lim and al., 2003) led the authors to estimate the number of microRNA in the human genome to be 255. Actually, current works reveal that the number of microRNAs was considerably underestimated. Indeed, to date, 474 microRNAs are already referenced in the public data base Rfam, while other scientists (Grad, 2003; Krichevsky, 2003; Bentwich and al., 2005) suggests that the number of microRNA within the human genome could be at least 800.

In the human genome, only a few of the known microRNA are fully characterized. Thus, for the largest part of them one cannot associate a function: which gene, which messenger RNA or which proteins they control. The development of a systematic approach, associating bioinformatics predictions with experimental validations makes it possible to increase the known set of microRNA molecules. Their exploitation opens new ways to discover new key regulatory and functional molecules directly implied in pathologies and to conceive a new classes of therapeutic tools (for example: biomarkers, diagnostic/prognostic molecules and drugs).

However, new computational methods need to be developed to overcome the limitations of today's standard bioinformatics and laboratory tools.

BRIEF SUMMARY OF THE INVENTION

This invention provides methods for prediction and identification of microRNA precursors (pre-microRNA) and microRNA molecules using data processing programs and databases. The invention also pertains to the isolated form of these pre-microRNAs, microRNA molecules and derived nucleic acids thereof. The invention also relates to recombinant vector, host cell, support, pharmaceutical composition or kit comprising such microRNA molecules or there of derivated molecules. The invention also applies to the use of such microRNA molecules and/or their identified targets in research, prognostic, diagnostic tools/methods as well as for therapeutic applications.

The method of the present invention brings new and effective solutions to identify new microRNA, thus offering an effective and relevant solution to allow the discovery of new microRNA, undetectable with current methods. The method of the present invention was validated by an approach using microarrays, which enabled the confirmation of the expression of predicted microRNA in different tissues. Embodiments of the method of the present invention makes it possible to eliminate most of the false positive occurrences observed with other methods, and to increase the sensitivity in the search of new microRNA.

Accordingly, in a first aspect, the invention provides a computer-implemented method of identifying microRNA precursor candidates in non-coding and coding regions of a genome. In some embodiments, the methods comprise:

receiving at least a first and a second genome from two different species, each containing a plurality of sequences including highly repetitive DNA;

masking a first set of highly repetitive DNA sequences in the first genome, wherein the first set includes SINE and LINE interspersed repeat sequences, but does not include at least 75% of other interspersed repeat sequences;

masking a second set of highly repetitive DNA sequences in the second genome, wherein the second set includes SINE and LINE interspersed repeat sequences, but does not include at least 75% of the other interspersed repeat sequences;

comparing the masked first genome to the masked second genome to determine pairs of sequences that are homologous between the two genomes;

creating a list of microRNA precursor candidates from the homologous pairs; and analyzing the list of candidates to:

eliminate sequences having less than 60 nucleotides; and identify sequences that have a stem-loop secondary structure with a 5' strand stem having from 20 to 45 nucleotides and with a 3' strand stem having from 20 to 45 nucleotides; and remove, from the list, sequences not having said stem-loop secondary structure.

In one embodiment, the other interspersed repeat sequences include processed pseudogenes, retrotranscripts, DNA transposons, and retrovirus retrotransposons.

In one embodiment, the methods further comprise the steps of:

creating a plurality of assemblies, each created from at least one pair of homologous sequences, wherein at least one assembly is created from a first group of at least two pairs of homologous sequences, wherein each pair of the first group has one sequence in common;

clustering the assemblies into a plurality of clusters, wherein each assembly of a cluster shares at least one sequence with at least one other assembly of that cluster, wherein a cluster includes one or more assemblies;

analyzing the properties of each cluster to eliminate sequences from the list of candidates.

In one embodiment, the methods further comprise the steps of:

analyzing the properties of each cluster to determine new sequences from the clusters to be added to the first set and second set of sequences that are masked, further comprising:

adding the new sequences to the first set and to the second set; and repeating masking with the first set and to the second set, comparing the masked genomes, creating a plurality of assemblies, and clustering the assemblies.

In some embodiments, analyzing the properties of a cluster to determine new sequences comprises:

determining the number of sequences of a cluster; and if the number of sequences of a cluster is greater than a predetermined number, selecting the sequences of that cluster to be added to the first set and to the second set.

In some embodiments, at least one assembly is created from a second group of at least two pairs of homologous sequences, wherein the two sequences from the first genome of the second group overlap to form a first sequence, wherein the two sequences from the first genome of the second group overlap to form a second sequence, wherein the size variation between the first sequence and the second sequence is less than 10%, and wherein the alignment between the first sequence and the second sequence shows more than 85% sequence similarity.

In some embodiments, at least one assembly is created from a second group of at least two pairs of homologous sequences, wherein the two sequences from the first genome of the second group are consecutive and form a first sequence containing an intervening sequence, wherein the two sequences from the first genome of the second group are consecutive and form a second sequence containing an intervening sequence, wherein the size variation between the first sequence and the second sequence is less than 10%, and wherein the alignment between the first sequence and the second sequence shows more than 90% sequence similarity.

In some embodiments, analyzing the properties of a cluster includes:

if a cluster has more than a predetermined number of sequences, eliminating the sequences of that cluster from the list of candidates.

In some embodiments, the predetermined number is four.

In some embodiments, the predetermined number is three.

In some embodiments, analyzing the properties of the cluster further includes:

flagging sequences that correspond to a coding gene as 'coding';

eliminating all of the sequences of the cluster if one of the sequences is flagged as 'coding'; and eliminating the sequences of an assembly if the assembly is not identical by at least 85% within a minimal window of 60 nucleotides.

In some embodiments, analyzing comprises the steps of:

eliminating a pair of homologous sequences if a secondary structure resulting from a folding of the sequences does not satisfy each of a first set of criteria including:

a number of nucleotides in a pre-miRNA stem-loop;

a terminal hairpin being of a certain length;

a percentage similarity of the sequences between the two genomes; and a Z score less than a specified amount; and eliminating a pair of homologous sequences if a secondary structure resulting from a folding of the sequences does not satisfy a predetermined number of a second set of criteria including:

a minimal free energy (MFE) of less than a specified amount;

a GC content being within a certain percent range;

a base-paring number being within a certain percent range; and perfect conservation of a sequence of a specified length along arms of the stem-loop.

In some embodiments, the first set and the second set of criteria have the following values:

the pre-miRNA stem-loop is between 60 to 120 nucleotides;

the percentage similarity of the sequences between the two genomes is at least 85%;

at least one 17 nt-long sequence is perfectly conserved along the arms of the stem-loop;

the terminal hairpin-loop is between 4 and 15 nucleotides;

the GC content is from 30% to 51%;

the base-pairing number is between 30 and 40%;
the MFE is lower than −25 kcal/mol; and
the Z score is less than 0.06.

In some embodiments, analyzing further comprises:
when a sequence has a secondary structure satisfying the first set of criteria and a predetermined number of the second set of criteria, extracting exact positions of the 5' strand start and exact positions of the 3' strand end to make a new sequence;

folding the new sequence to from a new secondary structure; and parsing the secondary structure of the new structure to determine if the secondary structure satisfies the first set of criteria and a predetermined number of the second set of criteria.

In another aspect, the invention provides a computer-implemented method of identifying non coding RNA candidates. In some embodiments, the methods comprise:

receiving at least a first and a second genome from two different species, each containing a plurality of sequences including highly repetitive DNA;

masking a first set of highly repetitive DNA sequences in the first genome, wherein the first set includes SINE and LINE interspersed repeat sequences, but does not include at least 75% of other interspersed repeat sequences;

masking a second set of highly repetitive DNA sequences in the second genome, wherein the second set includes SINE and LINE interspersed repeat sequences, but does not include at least 75% of the other interspersed repeat sequences;

comparing the masked first genome to the masked second genome to determine pairs of sequences that are homologous between the two genomes;

creating a list of non coding RNA candidates from the homologous pairs;

creating a plurality of assemblies, each created from at least one pair of homologous sequences, wherein at least one assembly is created from a first group of at least two pairs of homologous sequences, wherein each pair of the first group has one sequence in common.

clustering the assemblies into a plurality of clusters, wherein each assembly of a cluster shares at least one sequence with at least one other assembly of that cluster, wherein a cluster includes one or more assemblies;

analyzing the properties of each cluster to eliminate sequences from the list of candidates;

analyzing the list of candidates to:
eliminate sequences having less than 60 nucleotides; and
identify sequences that have a stem-loop secondary structure with a 5' strand stem having from 20 to 45 nucleotides and with a 3' strand stem having from 20 to 45 nucleotides;
remove, from the list, sequences not having said stem-loop secondary structure;
eliminating a pair of homologous sequences if the secondary structure does not satisfy each of a first set of criteria; and
eliminating a pair of homologous sequences if the secondary structure does not satisfy a predetermined number of a second set of criteria;

In a further aspect, the invention provides methods of determining a list of sequences to mask from at least one genome. In some embodiments, the methods comprise:

receiving at least a first and a second genome from two different species, each containing a plurality of sequences including highly repetitive DNA;

comparing the masked first genome to the masked second genome to determine pairs of sequences that are homologous between the two genomes;

creating a plurality of assemblies, each created from at least one pair of homologous sequences, wherein at least one assembly is created from a first group of at least two pairs of homologous sequences, wherein each pair of the first group has one sequence in common.

clustering the assemblies into a plurality of clusters, wherein each assembly of a cluster shares at least one sequence with at least one other assembly of that cluster, wherein a cluster includes one or more assemblies;

analyzing the properties of each cluster to determine if the sequences of that cluster are to be added to the list of sequences to be masked.

In some embodiments, analyzing the clusters comprises:
determining the number of sequences of a cluster; and
if the number of sequences of a cluster is greater than a predetermined number, adding the sequences of that cluster to the list of sequences to be masked.

In some embodiments, the predetermined number is 1000.

In a related aspect, the invention provides solid supports comprising at least 5 pre-microRNA or microRNA nucleic acid capture sequences, wherein each of the capture sequences are at least 15 nucleotides in length and have sufficient sequence complementary to specifically capture a nucleic acid sequence selected from the group consisting of SEQ ID NOs: 1-7803, preferably 1-4004 and 4035-7803, and the complement thereof.

In some embodiments, the at least 5 capture sequences have 100% sequence complementarity to a nucleic acid sequence selected from the group consisting of SEQ ID NOs: 1-7803, preferably 1-4004 and 4035-7803, and the complements thereof.

In some embodiments, the at least 5 capture sequences have 100% sequence complementarity to the pre-microRNA selected from the group consisting of SEQ ID NOs: 3, 5, 16, 22, 32, 34, 35, 36, 60, 70, 77, 81, 82, 90, 93, 139, 141, 151, 152, 158, 163, 170, 175, 176, 183, 184, 191, 192, 200, 205, 219, 223, 224, 248, 275, 276, 323, 328, 344, 357, 363, 366, 385, 400, 406, 407, 425, 472, 481, 489, 500, 501, 503, 512, 527, 530, 531, 563, 608, 633, 640, 651, 653, 664, 678, 728, 744, 753, 784, 785, 786, 826, 832, 858, 876, 903, 909, 911, 926, 927, 940, 942, 944, 946, 947, 951, 955, 963, 967, 975, 1055, 1060, 1083, 1118, 1129, 1137, 1145, 1160, 1161, 1166, 1173, 1174, 1175, 1198, 1205, 1207, 1217, 1233, 1238, 1251, 1267, 1299, 1321, 1323, 1343, 1352, 1396, 1403, 1429, 1485, 1531, 1545, 1547, 1559, 1586, 1592, 1601, 1610, 1611, 1617, 1634, 1645, 1649, 1653, 1656, 1661, 1667, 1681, 1686, 1688, 1693, 4773 and the complements thereof.

In some embodiments, the at least 5 capture sequences have 100% sequence complementarity to the microRNA selected from the group consisting of SEQ ID NOs. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2313, 2314, 2408-2410, 2427-2434, 2437, 2438, 2532, 2450, 2451, 2469-2471, 2476, 2477, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3232, 3233, 3249, 3250, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3557, 3567, 3619-3621, 3627, 3628, 3663, 3786, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994, 4001-4004, and the complements thereof.

In some embodiments, the at least 5 capture sequences have 100% sequence complementarity to the nucleic acid sequences selected from the group consisting of SEQ ID NOs: 4005-4034, and the complements thereof.

In some embodiments, the solid support is a nucleic acid array chip.

In a further aspect, the invention provides methods of detecting pre-microRNA or microRNA in a cell. In some embodiments, the methods comprise conducting multiplex polymerase chain reaction (PCR) to amplify at least 5 target pre microRNA or microRNA nucleic acid sequences using forward primers and reverse primers, wherein each forward and reverse primer pair member is substantially complementary to at least 15 contiguous nucleotides of a nucleic acid sequence selected from the group consisting of SEQ ID NOs: 1-7803, preferably 1-4004 and 4035-7803, and the complements thereof.

In some embodiments, the multiplex PCR methods comprise amplifying at least 5 pre-microRNA nucleic acid sequences selected from the group consisting of SEQ ID NOs: 1-1694 and 4035-5758.

In some embodiments, the multiplex PCR methods comprise amplifying at least 5 pre-microRNA nucleic acid sequences selected from the group consisting of SEQ ID NOs: 3, 5, 16, 22, 32, 34, 35, 36, 60, 70, 77, 81, 82, 90, 93, 139, 141, 151, 152, 158, 163, 170, 175, 176, 183, 184, 191, 192, 200, 205, 219, 223, 224, 248, 275, 276, 323, 328, 344, 357, 363, 366, 385, 400, 406, 407, 425, 472, 481, 489, 500, 501, 503, 512, 527, 530, 531, 563, 608, 633, 640, 651, 653, 664, 678, 728, 744, 753, 784, 785, 786, 826, 832, 858, 876, 903, 909, 911, 926, 927, 940, 942, 944, 946, 947, 951, 955, 963, 967, 975, 1055, 1060, 1083, 1118, 1129, 1137, 1145, 1160, 1161, 1166, 1173, 1174, 1175, 1198, 1205, 1207, 1217, 1233, 1238, 1251, 1267, 1299, 1321, 1323, 1343, 1352, 1396, 1403, 1429, 1485, 1531, 1545, 1547, 1559, 1586, 1592, 1601, 1610, 1611, 1617, 1634, 1645, 1649, 1653, 1656, 1661, 1667, 1681, 1686, 1688, 1693, 4773 and the complements thereof.

In some embodiments, the multiplex PCR methods comprise amplifying at least 5 microRNA nucleic acid sequences selected from the group consisting of SEQ ID NOs: 1695-4004 and 5759-7803.

In some embodiments, the multiplex PCR methods comprise amplifying at least 5 microRNA nucleic acid sequences selected from the group consisting of SEQ ID NOs. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2313, 2314, 2408-2410, 2427-2434, 2437, 2438, 2532, 2450, 2451, 2469-2471, 2476, 2477, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3232, 3233, 3249, 3250, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3557, 3567, 3619-3621, 3627, 3628, 3663, 3786, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994, 4001-4004, and the complements thereof.

Definitions

The term processed "pseudogene", as used herein refers to non-functional DNA sequences created by the reverse transcription of mRNA into cDNA with subsequent reintegration into the genome. Typically, processed pseudogenes fall into three categories. 1) those that are a complete copy of the mRNA transcribed from the functional gene; 2) those that are only a partial copy of the mRNA transcribed from the functional gene; and 3) those that contain sequences in addition to sequences expected to be present in the mRNA transcribed from the functional gene.

General structural characteristics of processed pseudogenes include: 1) the complete lack of intervening sequences found in the functional gene (e.g. introns sequences); 2) a poly A tract located at the 3'-end of the sequence; 3) direct repeats flanking the pseudogene sequence; and 4) in most cases the pseudogene is located on a different chromosome from that of the functional gene. In identifying the processed pseudogenes, the computer compares the query sequence against a database comprised of genomic sequences which encode for the functional gene.

The term "DNA transposon" or "Class II transposons", as used herein refers to DNA sequences belonging to a class of mobile elements that are capable of transposing from one site in the genome to a new site in the genome. DNA transposons transpose directly through a DNA intermediate, rather than through an RNA intermediate. A defining feature of a DNA transposon is a sequence encoding for a protein required for transposition, having at least 95% sequence identity, or sequence identity based on the default setting, whichever is lower, to the transposase of bacterial insertional sequence elements. The sequence encoding the transposase-like protein is flanked on each end by a short (i.e., 4-15 bp) inverted repeat (IR) sequence, which are required for transposition. Each inverted repeat is flanked on its outside by a short (4-15 bp) direct repeat (DR) sequence (i.e. the 5'DR is 5' to the 5'IR). Another feature of DNA transposons is that they may contain introns as part of the intervening sequence between the inverted repeats, unlike retrotransposons.

The computer identifies DNA transposons by identifying sequences that contain the following elements in the 5' to 3' direction. 5'-DR-IR-(coding sequence for protein having at least 95% sequence identity to consensus sequence for known transposases)-IR-DR-3'. As mentioned above introns may or may not be present in the coding sequence and these will be identified by comparing the coding sequence with the genomic sequence of the functional gene.

The term "retrotransposons" or "Class I transposons", as used herein refer to mobile DNA elements that transpose through an RNA intermediate utilizing reverse transcriptase activity. Retrotransposons are subdivided into two classes. The first class are retrovirus retrotransposons (synonymous with LTR transposons) because they exhibit many similarities to the genomes of retroviruses. For example, they contain long terminal repeats (LTR) which are typically about 100 bp to about 1 kb in length that flank the 5' and 3' ends of the protein coding sequence of the LTR transposon. The computer identifies retrovirus retrotransposons by comparing the query sequence against a consensus LTR sequence derived from a database of known LTR sequences.

The second class of retrotransposons are non-retrovirus retrotransposons (synonymous with non-LTR retrotransposons) because they lack the characteristic LTRs. Non-LTR retrotransposons can be further subdivided into at least two subclasses, the most abundant being long interspersed elements (LINE) and short interspersed elements (SINE).

The term "LINE" as used herein refers to long (typically greater than 5 kb) DNA sequences that represent reverse transcribed RNA molecules that were originally transcribed by RNA polymerase II. A consensus LINE element is characterized as having the following structural features. First, LINE elements are typically greater than 5 kb in size and have at least two open reading frames. Typically, ORF1 is located near the 5' end of the top strand following a region containing multiple stop codons in all possible reading frames. ORF2 is located in the top strand 3' to ORF1, and encodes a protein having at least 95% sequence identity, or sequence identity of the default settings, whichever is lower, to the reverse transcriptases of retroviruses and viral retrotransposons. Flanking the 3'-end of ORF2 is an AT rich region. The entire LINE element is flanked by direct repeats at the 3' and 5' ends.

The computer searches for LINE elements by identifying regions greater than 5 kb flanked by direct repeats. The intervening sequence, as discussed above will contain a region having multiple stop codons in all frames, followed by one to four open reading frames, one of which will share 95% sequence identity, or sequence identity of the default settings, whichever is lower, with proteins similar to reverse transcriptases of retroviruses and viral retrotransposons. The 3' most ORF is flanked on its 3'-end by an AT rich region.

The term "SINE" as used herein refers to short DNA sequences (about 500 bp or less) that represent reverse transcribed RNA molecules that were originally transcribed by RNA polymerase III into tRNA, rRNA and other small nuclear RNAs. SINES do not encode a functional protein having reverse transcriptase activity. The most common SINES are Alu elements which are typically about 300 bp and do not contain any coding sequences and can be recognized by the restriction enzyme AluI.

Most SINE elements identified to date share the following common elements. A 5' tRNA, rRNA, or other small nuclear RNA related region (including A and B boxes for internal RNA polymerase III promoters), a tRNA, rRNA, or other small nuclear RNA unrelated region, and a 3' AT rich region, flanked on both the 3' and 5' ends by direct repeats.

The computer identifies SINE sequences by identifying sequences about 500 bp or less flanked by direct repeats. These sequences will be compared to a consensus sequences for tRNA, rRNA or other small nuclear RNAs compiled from a database of known RNA sequences. Sequences meeting this criteria will then be screened for an AT rich region 5' to the direct repeat located at the 3' end.

The term "retrotranscript" as used herein refers to the RNA intermediate of the retrotransposon.

The term "homologous pair" as used herein refers to any pair of sequences that have been identified as sharing ancestry. Any method and/or criteria may be used. For example, a percentage of similarity or identity may be used. In such an embodiment, no specific percentage is required, but simply that a percentage has been specified. In some embodiments, a homologous pair shares at least 80%, 85%, 90%, 93%, 95%, 97%, 99% or 100% sequence identity. In another embodiment, a homologous pair may be identified though an associative property between two other pairs, such as is done in clustering embodiments of the present invention.

As used interchangeably herein, the terms "nucleic acid", "oligonucleotides", and "polynucleotides" include RNA, DNA, or RNA/DNA hybrid sequences of more than one nucleotide in either single-stranded or double-stranded form. The term "nucleotide" as used herein as an adjective to describe molecules comprising RNA, DNA, or RNA/DNA hybrid sequences of any length. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar. However, the polynucleotides of the invention are preferably comprised of greater than 50% conventional deoxyribose nucleotides, and most preferably greater than 90% conventional deoxyribose nucleotides. The nucleic acids of the invention may be prepared by any known method, including synthetic, recombinant, ex vivo generation, or a combination thereof, as well as utilizing any purification methods known in the art.

As used herein, the term "isolated" requires that the material be removed from its original environment (e.g., the natural environment if it is naturally occurring). For example, a naturally-occurring nucleic acid in a living animal is not isolated, but the same nucleic acid, separated from some or all of the coexisting materials in the natural system, is isolated. Such nucleic acid could be part of a vector and/or such nucleic acid could be part of a composition, and still be isolated in that the vector or composition is not part of its natural environment.

The phrases "selectively (or specifically) hybridizes to" or "selectively (or specifically) capture" interchangeably refer to the binding, duplexing, or hybridizing of a molecule only to a particular nucleotide sequence under stringent hybridization conditions when that sequence is present in a complex mixture (e.g., total cellular or library DNA or RNA). Typically, specific or selective binding will be at least twice background signal or noise and more typically more than 10 to 100 times background.

The terms "complementary" or "complement thereof" are used herein to refer to the sequences of a nucleic acid which are capable of forming Watson & Crick base pairing with another specified nucleic acid throughout the entirety of the complementary region. This term is applied to pairs of nucleic acid based solely upon their sequences and not any particular set of conditions under which the two polynucleotides would actually bind.

As used herein, the terms "complementary" or "complement" interchangeably refer to 100% antisense sequence identity.

The terms "sufficiently complementary" or "substantially complementary" interchangeably refer to antisense sequence identity between two nucleic acid sequences sufficient for hybridization under stringent hybridization conditions. Two nucleic acid sequences that are sufficiently complementary share at least 93% antisense sequence identity (i.e., 1 mismatched nucleotide over a length of 15 nucleotides). In some embodiments, sufficiently complementary nucleic acid sequences share at least 94%, 95%, 96%, 97%, 98% or 99% antisense sequence identity.

As used herein, the term "hybridizes to" is intended to describe conditions for moderate stringency or high stringency hybridization, preferably where the hybridization and washing conditions permit nucleotide sequences at least 60% identity to each other to remain hybridized to each other. Preferably, the conditions are such that sequences at least about 80%, 85%, 90%, 93%, 95%, 97%, 98%, 99% sequence identity to each other typically remain hybridized to each other. Stringent conditions are known to those skilled in the art and can be found in Ausubel, *Current Protocols in*

*Molecular Biology,* 2006, supra. A preferred, non-limiting example of stringent hybridization conditions are as follows: the hybridization step is realized at 65° C. in the presence of 6×SSC buffer, 5× Denhardt's solution, 0.5% SDS and 100 μg/ml of salmon sperm DNA. The hybridization step is followed by four washing steps:

two washings during 5 min, preferably at 65° C. in a 2×SSC and 0.1% SDS buffer;
one washing during 30 min, preferably at 65° C. in a 2×SSC and 0.1% SDS buffer;
one washing during 10 min, preferably at 65° C. in a 0.1×SSC and 0.1% SDS buffer, these hybridization conditions being suitable for a nucleic acid molecule of about 20 nucleotides in length. It will be appreciated that the hybridization conditions described above are to be adapted according to the length of the desired nucleic acid, following techniques well known to the one skilled in the art, for example be adapted according to the teachings disclosed in Hames B. D. and Higgins S. J. (1985) Nucleic Acid Hybridization: A Practical Approach. Hames and Higgins Ed., IRL Press, Oxford; and Current Protocols in Molecular Biolog (supra). Preferably, an isolated nucleic acid molecule of the invention that hybridizes under stringent conditions to a sequence of SEQ ID No 1 or 2 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As used herein, "percent sequence identity" between two nucleic acid sequences is intended to indicate a percentage of nucleotides between the two sequences to be compared, obtained after the best alignment (optimum alignment), this percentage being purely statistical and the differences between the two sequences being distributed randomly and over their entire length. The comparisons of sequences between two nucleic acid are traditionally carried out by comparing these sequences after having aligned them in an optimum manner, said comparison can be carried out, in addition to manually, by means of the local homology algorithm of Smith and Waterman (1981) [Ad. App. Math. 2:482], by means of the local homology algorithm of Neddleman and Wunsch (1970) [J. Mol. Biol. 48: 443], by means of the similarity search method of Pearson and Lipman (1988) [Proc. Natl. Acad. Sci. USA 85:2444), by means of computer software using these algorithms (GAP, BESTFIT, FASTA and TFASTA in the Wisconsin Genetics Software Package, Genetics Computer Group, 575 Science Dr., Madison, Wis., or else by BLAST N or BLAST P comparison software).

The percentage of identity between two nucleic acid sequences is determined by comparing these two sequences aligned in an optimum manner and in which the nucleic acid to be compared can comprise additions or deletions with respect to the reference sequence for an optimum alignment between these two sequences. The percentage of identity is calculated by determining the number of identical positions for which the nucleotide is identical between the two sequences, by dividing this number of identical positions by the total number of positions in the comparison window and by multiplying the result obtained by 100 in order to obtain the percentage of identity between these two sequences.

For example, one can use the BLAST program, "BLAST 2 sequences" (Tatusova et al., "Blast 2 sequences—a new tool for comparing protein and nucleotide sequences", FEMS Microbiol Lett. 174:247-250) available on the site http://www.ncbi.nlm.nih.gov/gorf/bl2.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

By a nucleic sequence having at least 80%, 85%, 90%, 91%, 92%, 93%, 94%, 95%, 96%, 97%, 98%, 99% sequence identity with a reference nucleic acid sequence, those having, with respect to the reference sequence, certain modifications, for example, a deletion, addition or substitution of at least one nucleotide, a truncation or an elongation. In the case of a substitution, it may be one or more consecutive or non-consecutive nucleotide(s).

General or current methods/protocols in molecular biology can be particularly found in the following references:
a) Sambrook and Russell, Molecular Cloning: A Laboratory Manual, 2001, Cold Spring Harbor Laboratory Press.
b) Bowtell and Sambrook, DNA Microarrays: A Molecular Cloning Manual, 2003, Cold Spring Harbor Laboratory Press.
c) Ausubel, et al., Current Protocols in Molecular Biology, 1987-2006, John Wiley Interscience.
d) Stirling and Bartlett, PCR Protocols, 2003, Humana Press.

BRIEF DESCRIPTION OF THE DRAWINGS

FIG. 10 illustrates secondary structures of select sequences (SEQ ID NOs: 7805-7821) according to one embodiment of the present invention.

DETAILED DESCRIPTION

Figure 1:
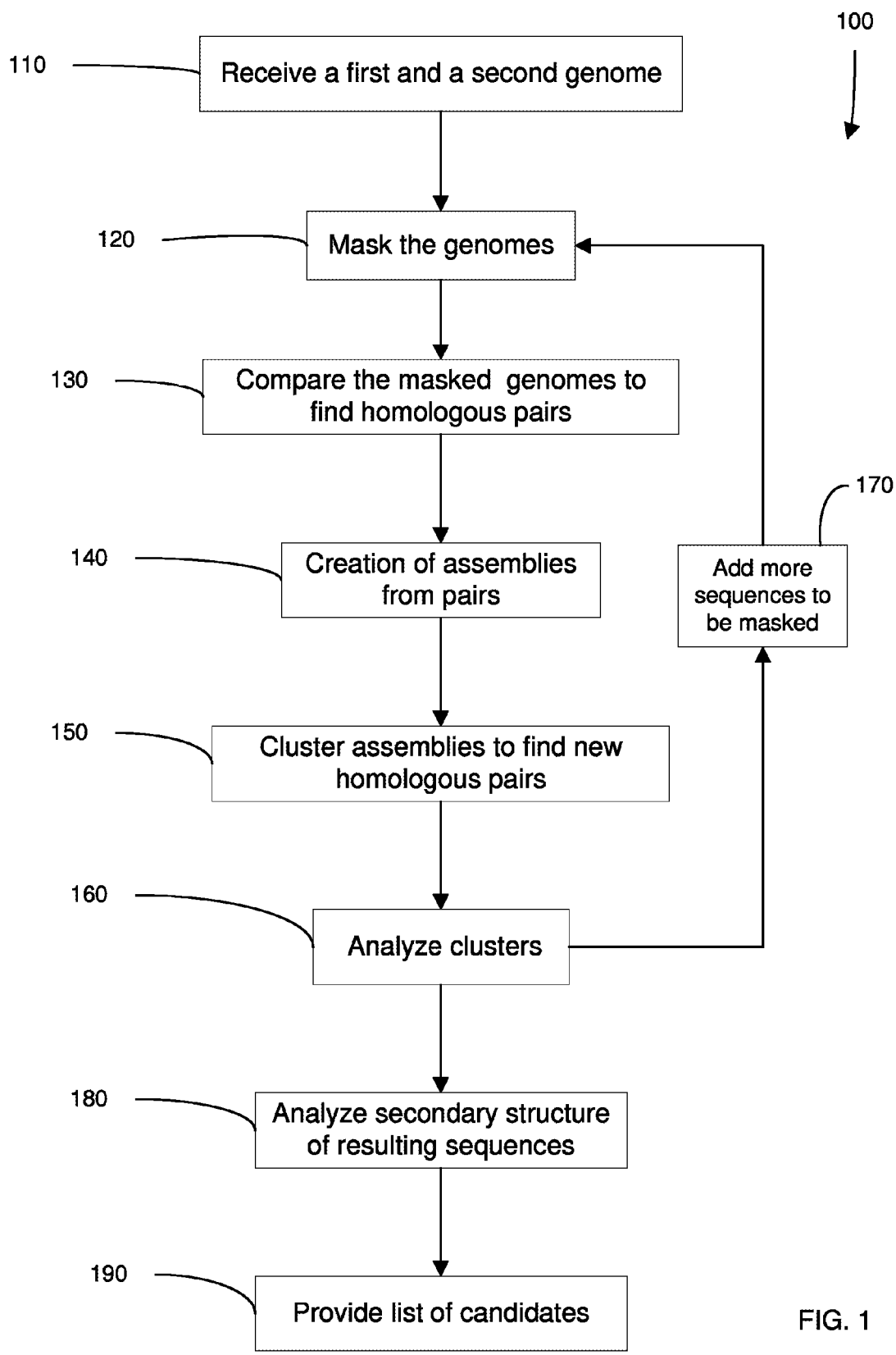
FIG. 1 illustrates a method of identifying microRNA precursor candidates in non-coding and coding regions of a genome according to an embodiment of the present invention.

This invention provides methods of identifying potential non-coding RNA, particularly microRNA precursor (pre-miRNA) candidates. In one embodiment, pre-miRNA are searched in homologous sequence pairs obtained from comparative genomics. In one aspect, to find more pre-miRNA, a different set of sequences are masked from the genomes than which is normally done. In some embodiments, the sequence pairs may be combined into assemblies and clustered to find new homologous relationships, which through analysis provide new techniques for discovering pre-miRNA. In another aspect, specific combinations of criteria and folding mechanism may be further used to determine pre-miRNA. Although, embodiments are directed to methods of finding microRNA precursor candidates, one skilled in the art will appreciate that embodiments may be used to find other non-coding RNA candidates.

I. Introduction

NpcRNA (non protein coding ribonucleic acids) such as tRNA and rRNA are known essentials regulators of gene expression and protein synthesis. MicroRNA constitute a vast family of non-protein coding RNA. These microRNA are very short in length. In the human genome their size generally varies between 17 nucleotides (for example: miR-138 and miR-496) and 25 nucleotides (for example miR-519a-1, miR519a-2). With very few exceptions, their functions are unknown.

The microRNA (or miRNA) can be processed in two different ways. In the first way of biosynthesis, the microRNA is encoded by its endogenous gene, and is transcribed as a long primary precursor called pri-microRNA (or pri-miRNA) (review Nelson et al 2003, Bartel 2004). In mammals, this pri-microRNA is cleaved by the nuclease Drosha (Lee and al., 2003) to give a precursor of approximately 60-120 nucleotides length, which is called the pre-microRNA (or pre-miRNA). This precursor folds into a short and irregular stem-loop secondary structure. The pre-microRNA is then exported by the enzyme exportin-5 to the cytoplasm of the cells (Yi and al., 2003; Lund et al. 2004; Bohnsack and al., 2004). The Dicer nuclease then cuts out the mature microRNA from the pre-microRNA (Hutvagner and al., 2001; Ketting and al., 2001; Knight and Bass 2001; Grishok and al., 2001). The mature microRNA are bound to a set of proteins, to the family of Argonaute proteins and the proteins Gemin3 and Gemin4 (most frequently in human cells), to form micro-Ribonucleoprotein complexes, called microRNP (or miRNP) (Mourelatos and al., 2002; Nelson and al., 2004).

In the second way of biosynthesis, the microRNA can be produced from introns of protein-coding genes. In this case, there is direct production of the pre-microRNA. Following maturation, steps remain common.

An essential characteristic of microRNAs are their antisense capability. The microRNAs function through more or less extended base-pairings with the 3'UTR region of specific messenger RNAs (Target Sequences of Recognition or TSR). According to the localization and the extent of complementarity (partial or complete), a microRNA will exert, either a repression of translation of this mRNA, or destruction of the messenger RNA target. In the latter case, an endonucleolytic cleavage occurs, which requires the intervention of an enzymatic complex called RISC(RNA-induced silencing complex).

MicroRNAs are involved in the cascades of events leading to cell differentiation. They control various metabolic pathways and physiological processes such as cell proliferation or cell apoptosis (Houbaviy H B., and al. 2003; He L and Hannon G J., 2004; Kasashima K, and al., 2004; Xu P., and al., 2004; Bartel P., 2004). Thus, microRNAs orchestrate many aspects of cell, tissue and organism development. They play key roles in the regulation of fundamental cellular mechanisms (Brennecke J and al., 3003; Chen C Z, 2004; Esau C and al., 2004; Yekta S, and al., 2004).

Specifically, there is now an accumulation of evidence demonstrating the direct role of microRNA in the development of pathologies, such as cancers. In the adenocarcinoma of the lung, a reduction of the expression of the microRNA let-7 is associated with a significant shortening of post-operational survival, while an over-expression of this same microRNA in a cellular line (A549) of adenocarcinoma of the lung inhibits the growth of the cancerous cells in vitro (Takamizawa J and al., 2004).

A strong expression of the precursor of the microRNA-155/BIC in the lymphoma of Burkitt was observed (Metzler Mr. and al., 2003). Two microRNAs (miR-143 and miR-145), which are conserved between human and mouse genomes, show substantial reduction of accumulation in definite stages of colorectal cancers (Michael M Z., 2003).

Deletion and decrease of expression of the microRNA miR15 and miR16 occur in the majority (approximately 68%) of leukemias of the "B cell chronic lymphocytic leukemia" type (Calin G A. and al., 2002; Calin G A. and al., 2004). These two microRNAs are localised on the chromosome 13q14, an area of 30-KB which is deleted in more than half of these leukemias. Also, it has been demonstrated that the microRNA mir-17-92 family is over-expressed in human lymphomas (He L, 2005). Moreover, an over-expression of the very same microRNAs results in a cancer in mice.

Recently, a direct link was established for the first time between microRNA and c-Myc, a proto-oncogene which encodes for a transcription factor and regulates cellular proliferation, cell growth and apoptosis (O' Donnel K A, 2005). The c-Myc simultaneously activates the transcription of the transcription factor E2F1 and the expression of 6 microRNAs, 2 of which (miR-17-5p and miR-20a) repress the expression of E2F1, thus allowing a fine control of the signals controlling cell proliferation.

MicroRNA are also involved in neurological and neurodegenerative diseases (Dostie, Z and al., 2003) and the brain expresses a great number of specific microRNAs (Kim J and al., 2004; Krichevsky AMNDT and al., 2004; Kubawara T and al., 2004); Miska E A. and al., 2004; Sempere L F. and al., 2004).

The metabolic diseases also involve microRNAs. Recently, it was shown that a microRNA (miR-375), specific to the pancreatic small islet-specific cells, controls insulin secretion. Thus, miR-375 is a regulator of the secretion of insulin and could constitute a new pharmaceutical target for the treatment of diabetes (Poy M N, and al., 2004).

MicroRNAs act through networks of interactions. Higher organism requires two levels of programming: on the one hand specification of the functional component (primarily the proteome) and on the other hand the orchestration of the expression and the assembly of these components during the stages of differentiation and development. MicroRNA, which interact with mRNA and proteins, determine how, when and where genes must be expressed. These regulations take place in a coordinated network with one microRNA regulating the expression of several different genes post-transcriptionally and one gene being regulated by several different microRNA. These interactions are imbricated, function on several levels and allow a precise adjustment, in real time, of expression/regulation of a specific set of proteins in a cell. Playing a central role in mechanisms of regulation essential for the development and the integrity of the cellular and tissue organization of organism, microRNAs multiply the possibilities of regulation and challenge our vision of the networks of interactions between gene products (Mattick J S., 2003).

Biological experiments show that changes in this network architecture are as significant as variations in the proteome components for the determination of cells differences, but also certainly determinant for the differences between species and individuals. MicroRNA expression is sensitive to environmental parameters, and has a differential susceptibility for pathologies.

The implication of the microRNA in the mechanisms responsible for the gene activation/inactivation results in changes of the protein expression profiles and therefore allows the change of the cell status, that is development and differentiation within a physiological context. However, due to this capacity, aberrant microRNA expression can lead to major changes in protein expression profiles resulting in the development of specific pathologies.

It is now acquired that the microRNA, similar to transcription factors, act in a co-operative dose-dependent manner upon their mRNA targets. Experimental results show that specific gene expression profiles of different tissues can be explained by the "microRNA code" (Hobert O., 2004; Doench J G and Sharp Pa., 2004) which relates to the specific set of microRNA expressed within different tissues.

In a general way, a set of microRNA is necessary to control the same mRNA. At the same time, a microRNA can have several different messenger RNA targets. This multiplicity of the targets and the co-operative aspect of the signals are essential features of the control of translation by microRNAs (Enright A J and al., 2003; John B and al., 2004).

MicroRNAs inhibit expression of protein-coding genes either without affecting the concentration of the targeted mRNA, or by decreasing its concentration (Lim L P and al., 2005). In vertebrates, 20 to 30% of the protein coding genes are supposed to be controlled by microRNAs (Lewis L P and al., 2005; Krek A and al., 2005; Xie X et al., 2005).

II. Methods of Identifying MICRORNA Precursor Candidates

In a first aspect, the present invention is directed to a computer-implemented method for the identification of candidate microRNA precursor molecules (pre-microRNAs). FIG. 1 illustrates a method 100 of identifying microRNA precursor candidates in non-coding and coding regions of a genome according to an embodiment of the present invention. These steps may be rearranged to be performed in a different order, and some steps may be removed. A general description of the method and these steps is initially provided. Subsequent sections provide greater detail of these specific steps and of some embodiments.

In step 110, at least two genomes are received. Any two genomes may be used and more than two genomes may be received. In one embodiment, the genomes are the *Homo Sapien* (human) genome and the *Mus Musculus* (mouse) genome. In other embodiments, the genomes may be from plants or any other living organism. In step 120, the received genomes are masked using a library of sequences. This masking reduces the amount of the genome that has to be analyzed, but does not reduce the amount of genome to be analyzed as to exclude significant portions of the genome that might include microRNAs.

In step 130, the genomes are compared, e.g., using BLAST, to determine pairs of sequences that are homologous between the two genomes. Any percentage of sequence similarity or identity may be used to define homology. In some embodiments, homologous pairs share at least 80%, 85%, 90%, 93%, 95%, 97%, 99% or 100% sequence identity. These homologues pairs may be used to create a list of microRNAs precursor candidates. In step 140, certain homologous pairs are combined into assemblies, for example, through filtering of coding sequences and optimisation of the data. In step 150, the assemblies are clustered, thereby, finding new homologous pairs of sequences.

In step 160, the clusters are analyzed. In one aspect, the sequences of certain clusters are removed from a list of microRNAs precursor candidates. In another aspect, the sequences of certain clusters are identified for being added to the library of sequences to be masked. Thus, in one embodiment, in step 170, these sequences are added to the library. At this point, steps 120-160 may be repeated as needed with the results from using the new library for masking in step 120. In step 180, the sequences remaining in the list of candidates are analyzed to determine if their secondary structure satisfies certain combination of criteria. In step 190, list of microRNAs precursor candidates is provided.

A. Masking the Genomes

A wide part of vertebrate genomes consists of stretches of highly repetitive DNA sequences classified into five categories: simple repeats, tandem repeats, segmental duplications and interspersed repeats. To avoid a tremendous number of spurious matches in whole genome comparisons or analyses, these low-complexity regions are "masked" by replacing corresponding nucleotides by another character, such "N" or "X" or a lowercase character of the same type. Typically, not only are highly repetitive sequences masked, but also pseudogenes, non-functional copies of RNA genes, small RNA pseudogenes and all active small RNAs.

Currently, almost 50% of the human genome is annotated as belonging to these classes, and is masked accordingly by the standard RepBase library. This masking of the genome has been designed for a more accurate and sensitive analysis of genomic regions directly related to the expression of coding genes. Accordingly, research has been focused on the coding part of the genomes, applying strong masking criteria and filtering out what they called <<junk DNA >>. Thus, most of these genomes lack non-coding RNA genes, mainly because the masking applied to the comparison has cleaned them out. With regards to finding microRNA, the result is that too much of the genome is masked out and removed from further analysis. When masking involves a comparison of an unknown sequence to a list of known sequences such as a list of transposons, retrotransposons or pseudogenes, the decision to mask or not to mask is made at the default settings of the software or at a 95% sequence identity level, which ever is lower, with a word size of 8, e-value of 1 and a penalty of −1 for one mismatch, unless otherwise stated.

Accordingly, in one embodiment, to find more microRNAs, non-processed pseudogenes, unitary pseudogenes, non-functional copies of RNA genes, non-protein coding RNAs, small RNA pseudogenes, snRNAs, snoRNA, and all active small RNAs are selectively or in combination not masked in appreciable numbers. This results in at least 75% of this group of sequences not being masked.

In another embodiment, only certain interspersed repeat sequences are masked, and an appreciable number of other interspersed repeat sequences are not masked. For example, the masking is restricted to an appreciable number of SINE and LINE interspersed repeated sequences, but not other interspersed repeat sequences, thus allowing this previously inaccessible part of the genome to be analyzed. In one aspect, the appreciable number of SINE and LINE sequences that are masked is from 75% to 100% of commonly attributed SINE and LINE sequences. In another aspect, an appreciable number of the other interspersed repeat sequences not being masked results in at least 75% of these other interspersed repeat sequences not being masked. In another aspect, the other interspersed repeat sequences, which are not masked, include one or more of processed pseudogenes, retrotranscripts, DNA transposons, and retrovirus retrotransposons.

In one embodiment, the sequences which are not included in the masking library are interspersed repeated sequences other than SINE and LINE, but also other non-coding RNA. For example, all non-functional genes (such as pseudogenes and small RNAs), which are normally included in the "available masking files", are not included in the masking file of an embodiment of the present invention.

Therefore, embodiments of the present invention have investigated about 20% of mostly unexplored human and mouse genome sequences (about 500 millions nucleotides located in non-coding regions never analyzed by others). Thus, subsequent steps of comparing two masked genomes, analyzing secondary structure, and identifying highly conserved areas in the secondary structure can find previously hidden microRNA precursor molecules.

In one embodiment, BLAST is used with a set (library) of repeat sequences as defined for one of the embodiments being used as the database and the genome defined as query. Other sequence alignment tools and software may be used. The result from BLAST provides where the sequences of the library appear in the genome. These found sequences can then be removed or replaced with 'X'. For example, xblast.pl may parse the results and remove sequence repeats, replace the sequences with 'X', replace the sequences with lower case letters, or replace the sequences with any other character.

In one aspect, this methodology of using a library of sequences to be masked allows for much more precision as only the sequences included in the library are masked. In contrast, RepeatMasker extends in 5' and 3' the sequences contained in their library. This results in a large masking around each sequence of the library.

B. Comparing the Two Masked Genomes

The masked genomes are compared to determine pairs of sequences that are homologous between the two genomes. In one embodiment, an alignment algorithm is used to identify between the two genomes a pair of sequences that have a sufficient percentage of similarity (identity).

In one embodiment, each genomic comparison was performed using mpiBLAST (Darling et al., The Design, Implementation, and Evaluation of mpiBLAST), that is an implementation of the ncbi Blast (Karlin, Altschul PNAS 87:2264-2268, 1990) allowing the use of a cluster of computer in a Massive Parallel Interface (MPI) language. In one aspect, four dual processor computers were used with another computer running as master controller for all the jobs.

BLAST calculates all segment-pairs between the query and the database sequences that present sequence similarity above a scoring threshold. The result is a list of high-scoring pairs (HSPs). Each HSP is a pair of sub-sequences of the same length that form an ungapped alignment. The number of HSPs found depends of the parameters set for running BLAST. In particular, BLAST will report only those sequences whose scores are over some cutoff score. In one embodiment, the BLAST parameters used were: e-value: 0.01; and word size: 11. However, any parameters and any percentage of sequence similarity or identity may be used to define homology. In some embodiments, homologous pairs share at least 80%, 85%, 90%, 93%, 95%, 97%, 99% or 100% sequence identity.

One genome may be used for making queries to the other genome, which is used as the database. In one embodiment, the masked *Homo sapiens* genome was used as the query and the masked *Mus musculus* genome was used as the database. In one aspect, MySQL was used as the database environment. In this embodiment, computing took about 6.5 days to compare the *Homo sapiens* genome (as query) and the *Mus musculus* genome (defined as database). The sequence used as query (*Homo sapiens*) was split in chunks of 100000 base pairs (bp) with an overlap of 3000 bp. This was done to increase the speed of the comparison and to avoid overloaded computer memory.

In one aspect, the homology coordinates between the query and the hit are stored in a database. The coordinates are defined as a High Scoring Pair (HSP as defined by BLAST). Each HSP is defined by a start, an end and a strand on each genome. In one embodiment, a total of over 1 million HSPs were obtained at the end of this step. These homologues pairs may be used to create a list of microRNA precursor candidates.

Since BLAST relies on heuristic procedures, it is not guaranteed to find the best matches. Also, BLAST produces only binary relationships between one sequence of genome 1 and one sequence of genome 2. Thus, some of them can be missed, in particular when long sequences are compared (such as two mammalian genomes). In our case, both the Query sequence (human genome) and the Database (mouse genome) are very long. Thus, in one embodiment, the parameters are set in order to increase the predictiveness to avoid false positive. A direct consequence is a decrease in sensitivity, i.e. the loss of true positives.

C. Creation of Assemblies from Homologous Pairs

The creation of "assemblies" can generally be achieved by two different processes. In filtering, two HSPs that overlap or are successive are combined. In optimization, HSPs that share the same sequence are collapsed into the same entry.

Filtering reduces the number of HSP (potentially over one million) by assembling the HSPs into large sequences, which are one form of an "assembly". In view to (1) avoid potential overlaps between HSP and (2) have a more realistic view of sequence homologies between the genomes compared, a unique record integrates those HSP which sequences are either overlapping or consecutive in the two genomes. These assembled HSPs are included within the term "assemblies".

Figure 2A:
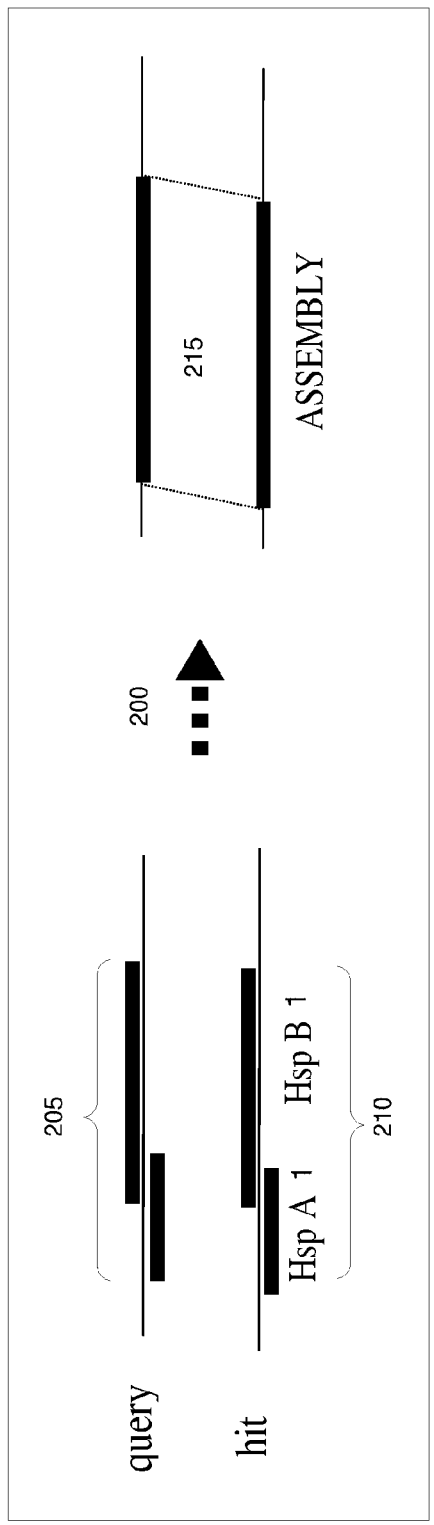
FIG. 2A illustrates an assembling process of creating an "assembly" by filtering according to one embodiment of the present invention.

FIG. 2A illustrates an assembling process 200 of creating an "assembly" by filtering according to one embodiment of the present invention. In process 200, if two or more HSPs share the same query and hit genomic sequence in terms of genomic position, then a new 'HSP' is built and an "assembly" is created. For example, HSP A1 and HSP B1 share the same query sequence 205 and hit sequence 210. Thus, they are combined into assembly 215.

Figure 2B:
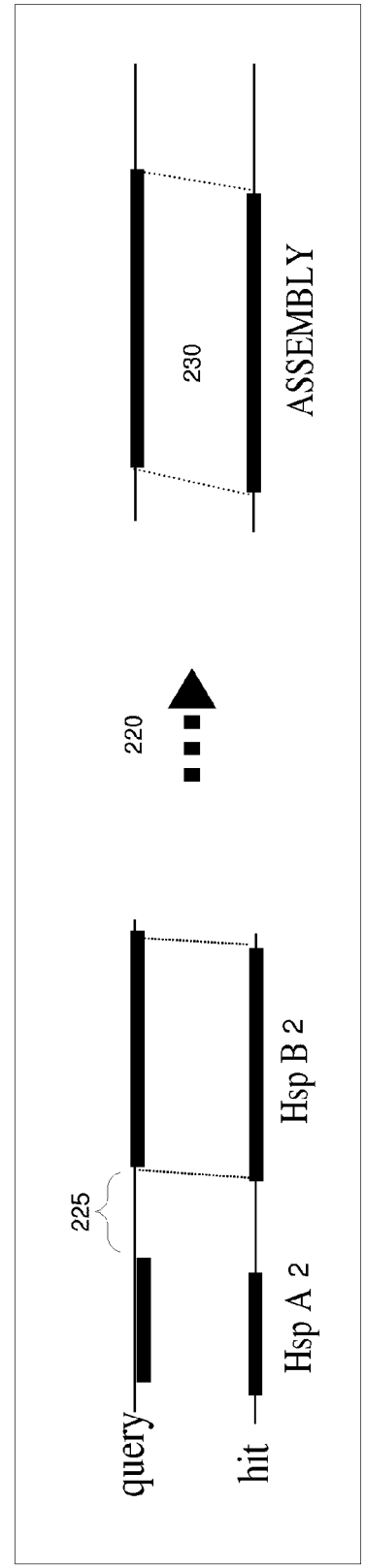
FIG. 2B illustrates another assembling process of creating an "assembly" by filtering according to one embodiment of the present invention.

FIG. 2B illustrates another assembling process 220 of creating an "assembly" by filtering according to one embodiment of the present invention. In process 220, if two queries and two hits coming from two HSPs share the same chromosome and have a distance which is similar, then a new 'HSP' is built and an "assembly" is created. For example, HSP A2 and HSP B2 share the same chromosome and have a distance 225 which is similar. Thus, they are combined into assembly 230. So, an assembly may be defined by a start, an end, a chromosome, a strand on the query and on the hit, and an internal identifier in the database.

Therefore, an assembly created by filtering is a set of HSPs that follow certain rules. In one embodiment, for the two genomes (species) included in the comparison, the size variation between two sequences of two consecutive HSP is less than 10%, and the resulting alignment including the two HSPs plus the intervening sequence must show more than 90% sequence similarity.

An "assembly" may also be created by optimization. Optimization avoids redundancies in the database, as "query" sequences having many "hits" are grouped in only one entry. When making a BLAST run, if a sequence defined as a query is present many times in the database, the results will give a report with the number of HSPs being equal to the number of times the sequence is present in the database. HSPs with the above characteristic are grouped into an "assembly". This means all the "hits" will then refer to one "query" in the database, which are then marked with an integer. This step makes it possible to reflect the situation in the genome and to make a data compression of at least 29%.

Figure 2C:
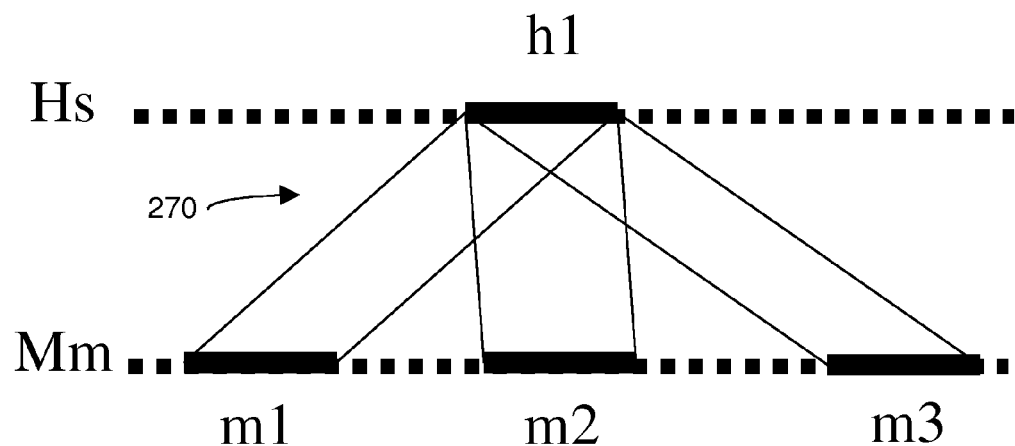
FIG. 2C illustrates an assembling process of creating an "assembly" by optimization according to one embodiment of the present invention.
Figure 2C:
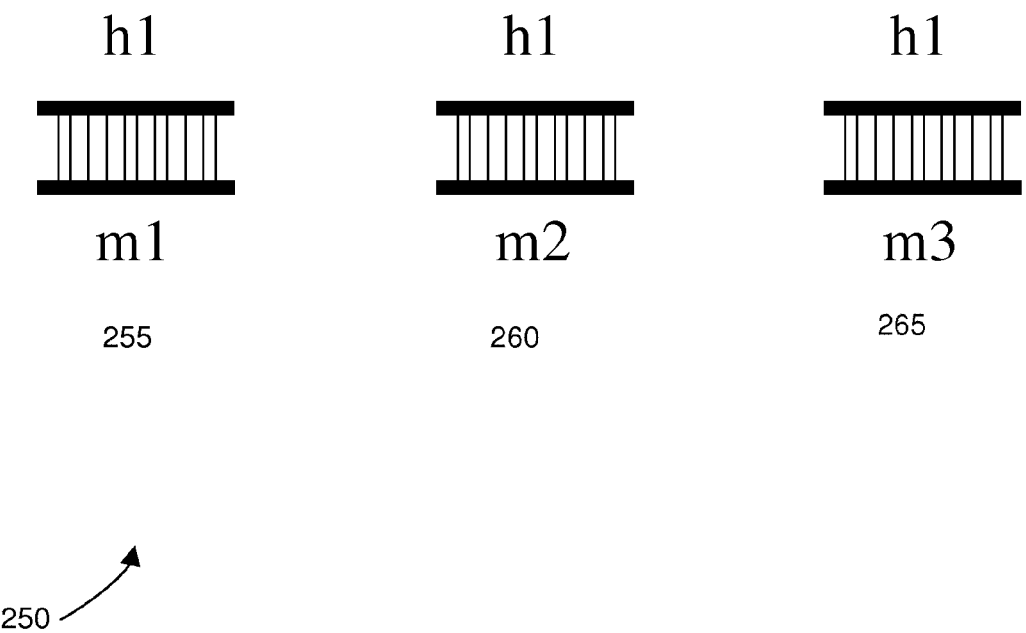

FIG. 2C illustrates an assembling process 250 of creating an "assembly" by optimization according to one embodiment of the present invention. Three BLAST reports obtained three HSPs 255-265. Each HSP 255-265 has sequence "h1" as the query. Thus, process 250 combines HSPs 255-265 into "assembly" 270.

Thus, after this step, the list of homologous sequences is recorded either in HSPs or assemblies. Each homologous pair of sequences (HSP or assembly) is recorded with exactly the same information. An assembly may be defined by the resulting file containing the mix of HSPs and "assembled HSP" from the filtering process. An "assembly" also includes HSPs that have not been combined with other HSPs. For example, in instances, where filtering and optimization does not apply to an HSP, then that HSP would be considered an assembly.

Thus, in one embodiment, an assembly is defined by: an identifier, for both human and mouse genomes a chromosome, a start, an end, a strand. One query sequence (with a chromosome, a start, an end, a strand) may belong to many "assemblies". One hit sequence (with a chromosome, a start, an end, a strand) may also belong to many "assemblies".

D. Clustering of Homologous Sequences

In order to reduce the background noise due to the genomic comparison and to filter sequences that are over represented in the two genomes, a clustering method is applied to cluster assemblies with homologous sequence but different genomic positions. In one aspect, the background noise comes from the fact that the BLAST parameters are chosen for increasing predicteness. Thus, very few false positive homologous sequences are obtained, but some true positive ones are lost. A subsequent clustering of assemblies allows finding undetected true positives.

Each assembly record contains an alignment of the two sequences identified as "homologous" by BLAST. This homology is, in particular, dependent on the degree of similarity between the two sequences. Each sequence within an assembly is defined by its coordinates (5' end, 3' end) along the genome, the genomic strand (plus or minus) and the chromosome number. The coordinates (5' end and 3' end, strand and chromosome identification) of the sequences for all assemblies are scanned. In one embodiment, assemblies are clustered together if each assembly of a cluster contains one sequence (either query or database) which has exactly the same coordinate (5' end and 3' end, strand and chromosome identification) as at least one other assembly of the cluster. The underlying assumption is: if A is homologous to B and A is homologous to C, then B and C are homologous, which potentially has been missed by BLAST. This is term an associative property of homologous pairs.

Figure 3:
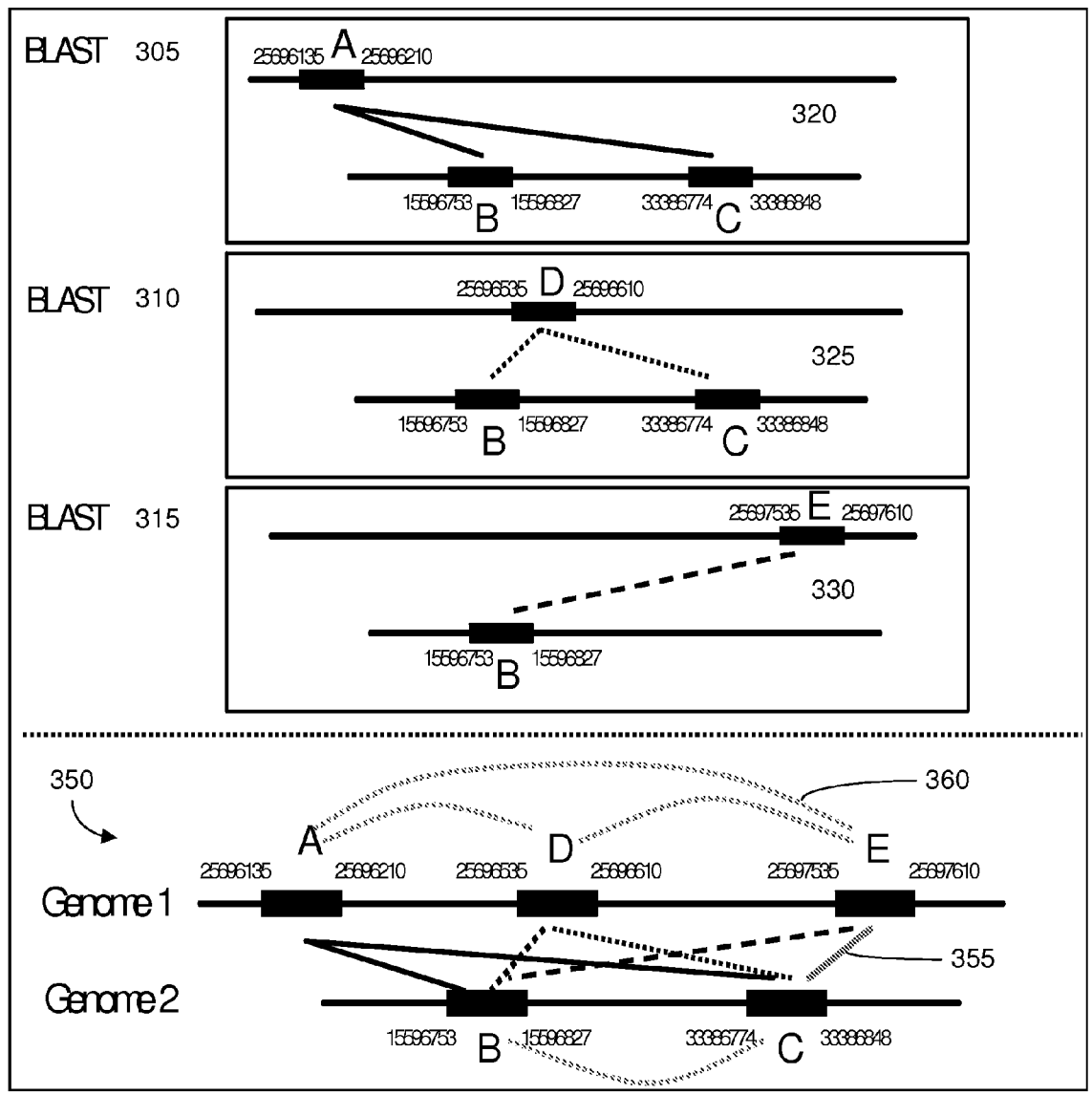
FIG. 3 illustrates a cluster created according to an embodiment of the present invention.

FIG. 3 illustrates a cluster 350 created according to an embodiment of the present invention. Three BLAST reports 305-315 provide three different assemblies 320-335. These assemblies 320-335 are combined into cluster 350 by a clustering process that tests if at least one sequence of an assembly is shared with at least one other assembly of a cluster. In this example, there is even more sharing as each assembly shares sequence B. In this manner, new homologous relationships are found.

For example, sequences E and C, which are not seen as homologous by BLAST report 315 are actually related as shown by their very high sequence similarity with the other sequences of this cluster. This homology of an orthologous type is signified by the new relationship 355. Also, sequences A, D, and E are homologous to each other. This homology of a paralogous type is signified by relationships 360. Each line in FIG. 3 signifies a homologous relationship, and each sequence in a cluster has a homologous relationship with every other sequence of that cluster.

Despite working on coordinates of homologous sequences detected by BLAST, an embodiment clusters together only sequences which have evident homologous relationships (high similarity rate). This is one of advantages of such a clustering method according an embodiment of the present invention. In one aspect, appropriate SQL syntax and Perl scripts are used to cluster "assemblies" that share at least one sequence (sequence hit or sequence query) with at least one other "assembly" of the cluster.

Figure 4:
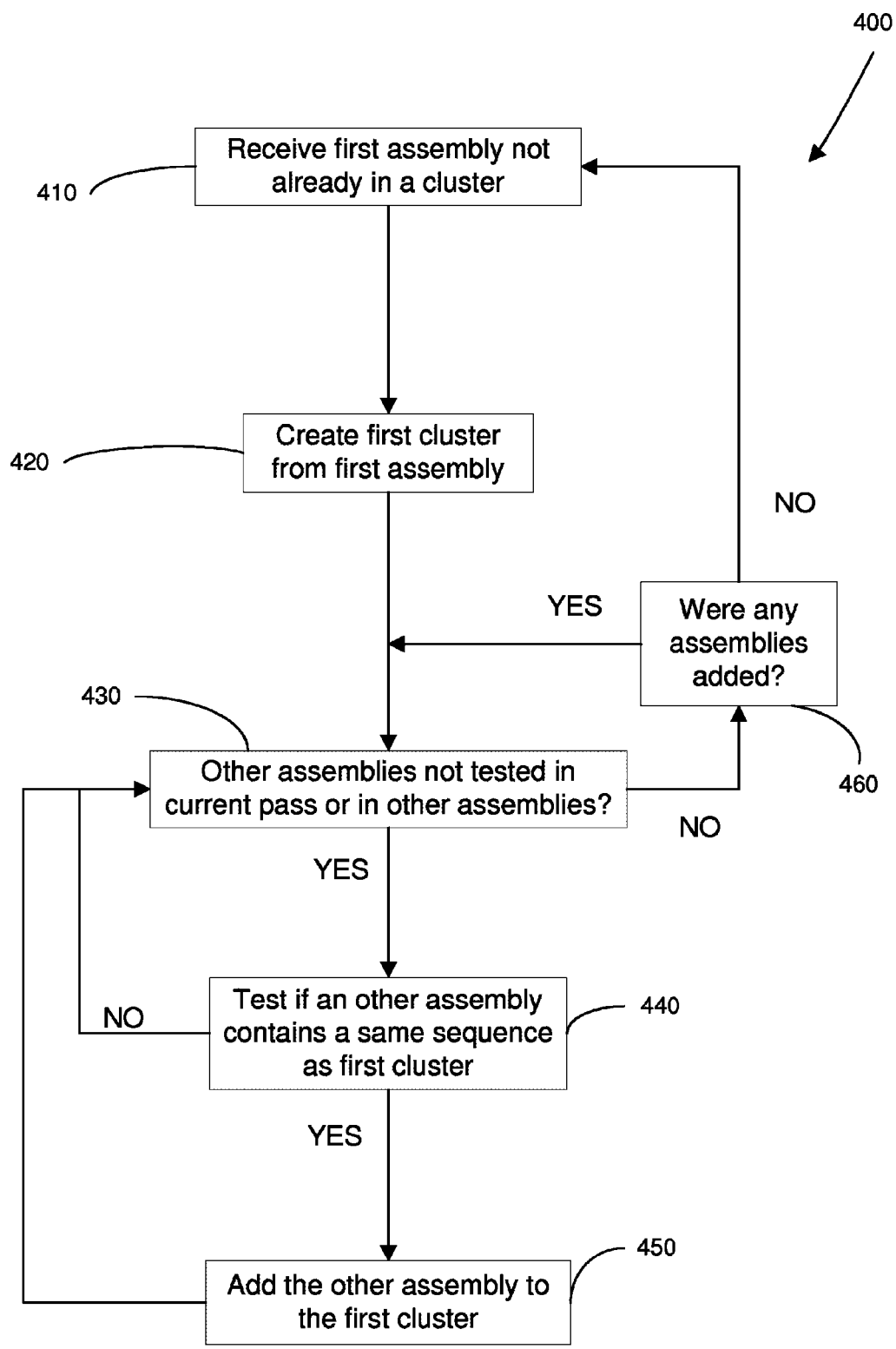
FIG. 4 illustrates a method of clustering assemblies according to an embodiment of the present invention.

FIG. 4 illustrates a method 400 of clustering assemblies according to an embodiment of the present invention. In step 410, a first assembly is received. In step 420, a cluster is created from the first assembly. At this point, the cluster and assembly are identical as no other assemblies have yet been added. In step 430, it is determined if other assemblies have not been tested. In one aspect, it is also determined if other assemblies do not already belong to a cluster.

If there is another assembly, in step 440, the other assembly is tested whether the assembly contains a sequence in the first cluster. If the other assembly does not contain a sequence that is within the first cluster, then the process reverts back to step 430 to determine if there are any other assemblies to be tested. If the other assembly does contain a sequence that is within the first cluster, then the sequences of that assembly are added to the first cluster. Once the assemblies are exhausted, the method moves form step 430 to step 460, which determines if any assemblies have been added to the first cluster in the current pass through the assemblies. If an assembly has been added in the current pass, then another pass of testing the assemblies is made. If no assemblies have been added, then method 400 repeats for the remaining assemblies not already in a cluster by receiving one of them and starting a new cluster. One skilled in the art will appreciate other methods for performing the clustering according to the rule that at least one sequence of an assembly is shared with at least one other assembly of a cluster.

Figure 5:
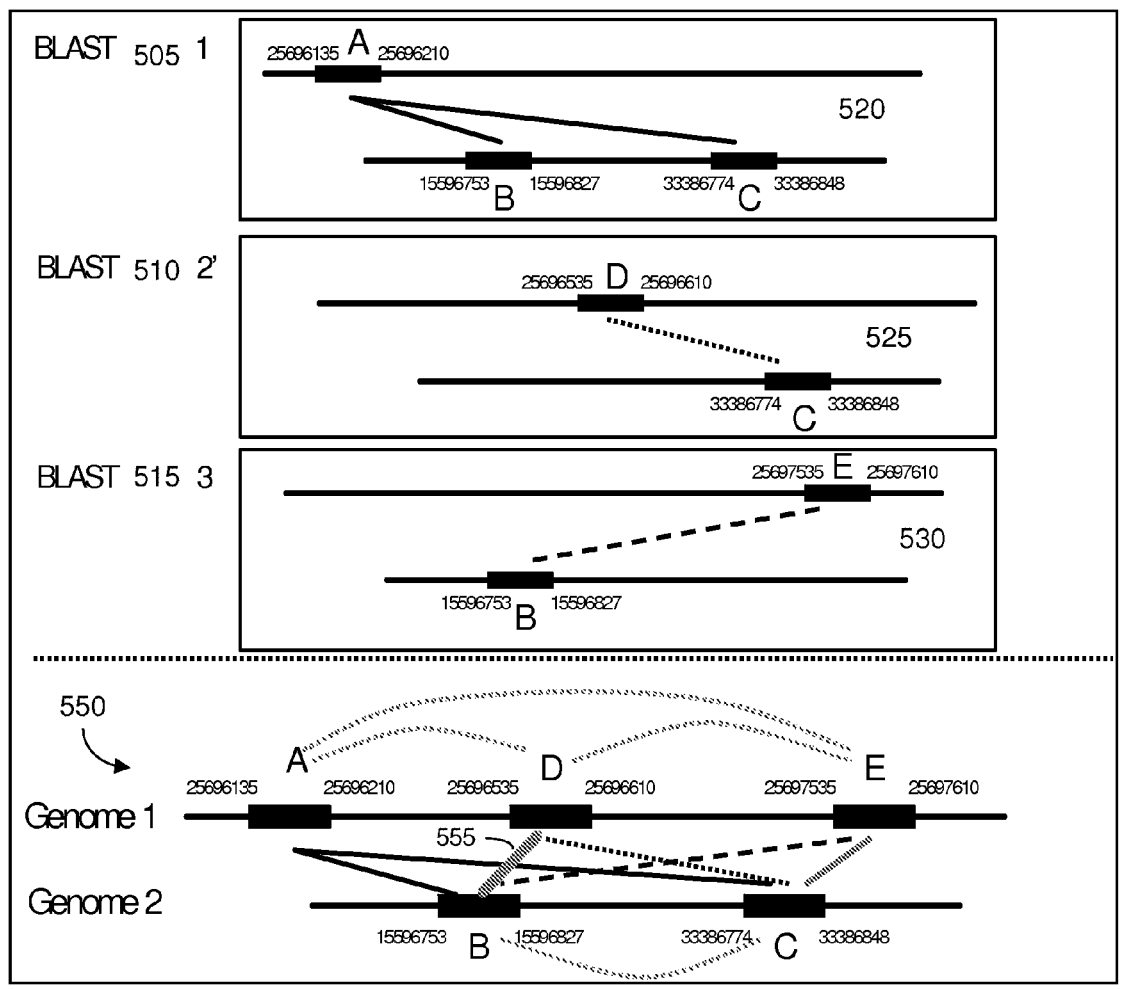
FIG. 5 illustrates a cluster created according to an embodiment of the present invention.

FIG. 5 illustrates a cluster 550 created according to an embodiment of the present invention. Three BLAST reports 505-515 provide three different assemblies 520-535. These assemblies 520-535 are combined into cluster 550 by a clustering process, which tests if at least one sequence of an assembly is shared with at least one other assembly of a cluster, e.g. method 400. In this example, BLAST report 510 has not shown a homologous relationship between sequence D and B. However, since assembly 520 and assembly 525 both share sequence C, cluster 550 contains both D and B, thus deeming them to have a homologous relationship 555, which is of the orthologous type to be precise.

In one embodiment of using method 400, the first assembly received (410) is the assembly 520 of sequences A, B, and C. In step 420, cluster 550 is formed from assembly 520. In step 430, it is determined that assemblies 525 and 530 have not been tested. Control then moves to step 440, where assembly 525 is tested if assembly 525 contains a sequence in common with the sequences of cluster 550, which at this point are sequences A, B, and C. Since assembly 525 shares sequence C with cluster 550, sequence D is added to cluster 550, in step 450. Then upon returning to step 430, it is determined that assembly 530 has not been tested. At step 440, sequence B is determined to be shared between assembly 530 and cluster 550. Thus, at step 450, sequence E is added to cluster 550.

If there were other assemblies that were not added to cluster 550, then these remaining assemblies would be clustered in a similar procedure. In one aspect, another pass at the remaining assemblies is done to determine if any of them share sequences with assemblies (effectively then entire cluster) that were added to the cluster after that assembly was tested. This may be needed to ensure that a cluster has all assemblies of the genome that are homologous within one cluster. Continued passes over the remaining assemblies may be performed until no more assemblies are added. At that point, a new cluster may be created from one of the remaining assemblies, and method 400 may be repeated for that cluster.

Thus, in one embodiment, a cluster is created as a set of "assemblies" that are homologous in sequence. In one aspect, a cluster is referenced by an identifier which refers to the set of identifiers for each of the assembly of the cluster. In another aspect, a cluster is also referenced by the number of homologous sequences (links) that a cluster contains from the organisms that have been used for the comparative genomics. The number of links for each cluster is then stored in the database, along with the corresponding assemblies.

In one aspect, this clustering method allows grouping of paralogous sequences and orthologous sequences together. Paralogous sequences are sequences that have diverged from a common ancestral sequence. Orthologous sequences are sequences that have evolved directly from an ancestral sequence. According to this clustering method, the number of times a sequence is present in the genomes is known, and specifically the number of times a sequence is present in the query genome and how many times the same sequence is present in the database sequence is known.

The initial BLAST comparison is based on the similarities between the sequences to identify homology relationships. In one aspect, our clustering method allows to group together all the sequences of both genomes which are homologous, between the two genomes. In addition, this clustering step allows identifying all the paralogous sequences within each genome. The underlying tenet is a systematic reference to homology relationships between sequences of the two genomes compared by BLAST.

In another aspect, this clustering method allows increasing the sensitivity of the BLAST result without increasing the number of false positive. The clustering method can identify homology relationships not detected by BLAST. The predictiveness of BLAST results is consequently also considerably increased.

E. Analyzing Clusters

1. Selecting Sequences to Add to Masking Library

In one embodiment, the clustering of assemblies was also used to identify new highly repeated sequences. These new repeat sequences may be added to the masking library, as described in step 170 of FIG. 1. These new repeat sequences may be determined from the clusters of assemblies. In one aspect, these new repeat sequences are taken from clusters that have a large number of sequences within that cluster. For example, clusters having more than 1000 sequences may be identified as being highly repetitive and are added to the masking library. In other embodiments, the required number of sequences may be as low as 500.

In one embodiment, 1200 different clusters having more than 1000 sequences were identified. In one aspect, for each cluster, one sequence is sufficient to define a cluster. Thus, one new repeat sequence may be added to the masking library for each cluster having a sufficient number of sequences.

Then, as was previously done in step 120 of FIG. 1, BLAST is used to mask each genome with these new sequences.

2. Annotation of the Conserved Non-Coding DNA

In one embodiment, to predict non-coding genes and in particular microRNA genes, all the coding regions as defined by an official genome annotation are flagged in order to exclude them for future predictions.

Using a database of the "assemblies" and knowing the exact position of the sequence corresponding to the query (e.g., human genome) and using human annotation provided by Ensembl on the same genome, the exact position of the query sequence which does not code for a protein with a 'non-coding' flag is stored in the database. Thus, in one aspect, the coordinates of each query sequence, which is conserved, are used to define whether sequence is part of a coding gene or not. All the conserved regions are then flagged 'coding' when they correspond to a coding gene. Then, the coordinates for the non-coding part of the conserved query genome are stored in a database.

Figure 6:
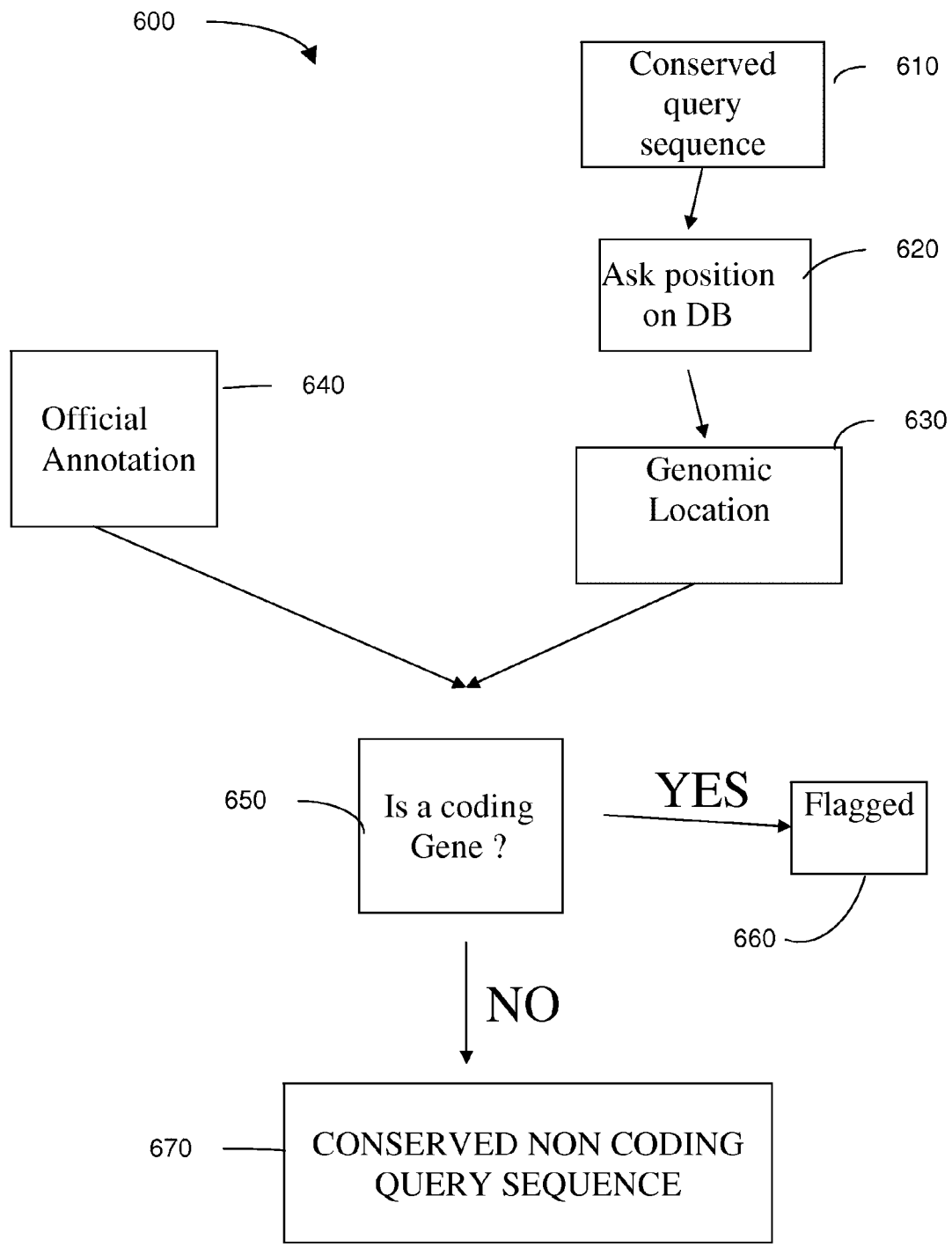
FIG. 6 illustrates a method of annotating the sequences of assemblies as containing coding or non-coding DNA according to an embodiment of the present invention.

FIG. 6 illustrates a method 600 of annotating the sequences of assemblies as containing coding or non-coding DNA. In step 610, conserved query sequences are taken from the sequences of the assemblies belonging to one of the genomes, e.g., the query genome. In step 620, the positions of the sequences are obtained from the database. In step 630, the genomic location of the sequence is determined from the positions. In step 650, these sequences are compared to the official annotation 640 to determine if a gene is coding or not. In step 660, if the gene is coding then the sequence is flagged as coding. In step 670, if the sequence does not contain a coding gene then it is determined to be a conserved non-coding query sequence.

3. Elimination of Assemblies and Clusters

In one embodiment, the sequences of the clusters are analyzed in order to eliminate one or more of the sequences as microRNA precursor candidates. In one aspect, one or more of the following characteristics are used to eliminate sequences. MicroRNA are: (1) present as only a relatively low number or less of copies in one genome, e.g., about 6 per genome, which results in about 12 per cluster when two genomes are used; (2) flagged as non-coding; (3) at least 60 nucleotides (nt) in length under the form of their precursor; and (4) conserved with at least 85% identity between two genomes, such as *Homo sapiens* and *Mus musculus*. In one embodiment, only the length characteristic is used.

Figure 7:
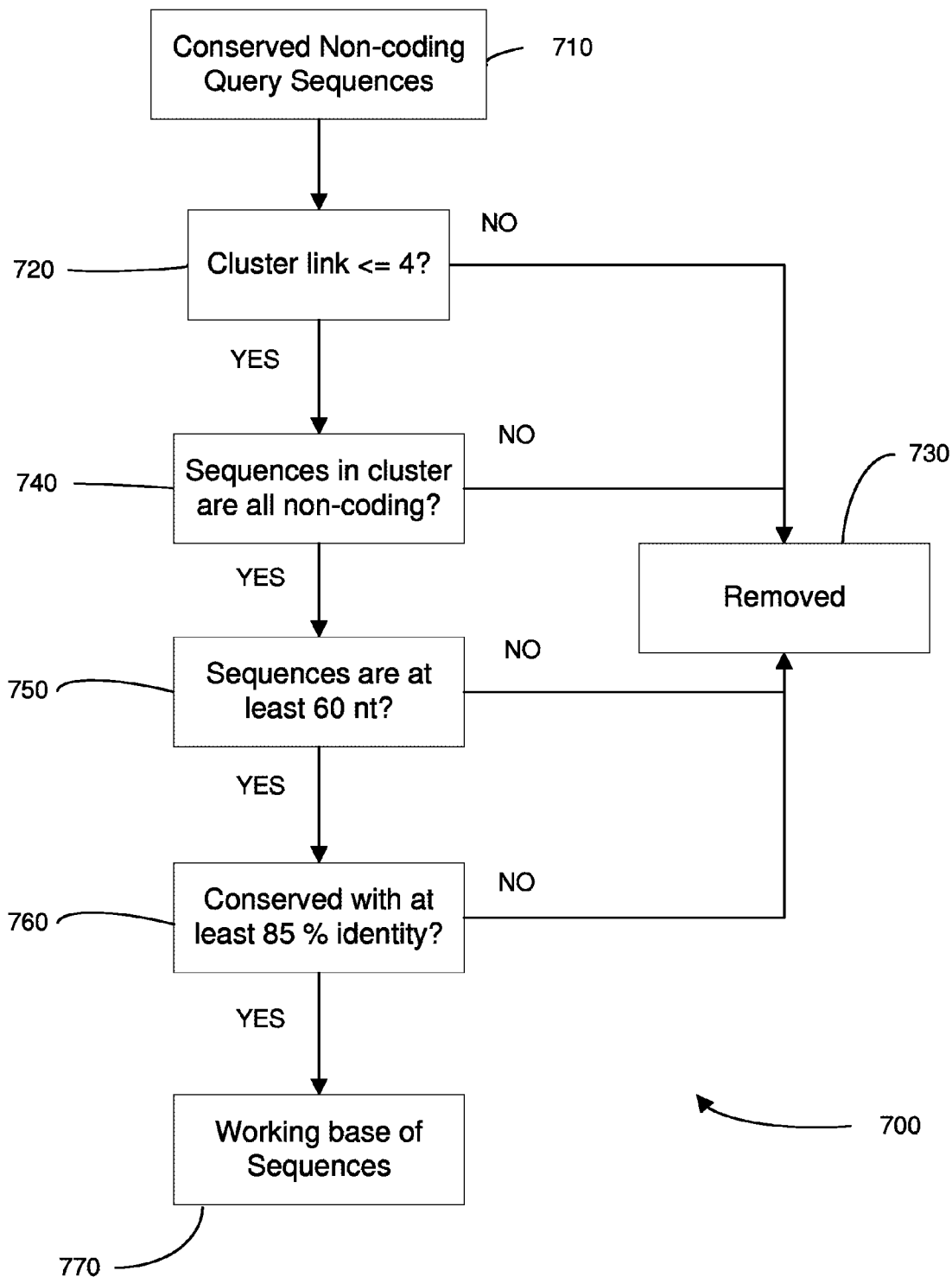
FIG. 7 illustrates a method of eliminating sequences of assemblies and clusters according to an embodiment of the present invention.

FIG. 7 illustrates a method 700 of eliminating sequences of assemblies and clusters according to an embodiment of the present invention. In step 720, non-coding sequences 710 based on the query annotations are checked to see if they are in a cluster with less than or equal to a certain number of homologous sequences (links). For example, if four links is used, then a sequence is checked to determine if the sequence is in a cluster with no more than 2 hits and no more than 2 queries. If a cluster satisfies this characteristic, one or more of the sequences of a cluster remain in the list of candidates. If a cluster does not satisfy this characteristic, then the sequences of the cluster are removed from the list of candidates at step 730. The total number of hits and queries may also be used, in addition to the number specifically in each genome.

In step 740, all the sequences in a given cluster are checked to determine if they are all flagged as 'non-coding'. If a cluster satisfies this characteristic, the cluster remains in the list of candidates, and if not, then it is removed in step 730. In step 750, sequences are checked if they have at least 60 nucleotides. In step 760, an assembly is checked to determine if the sequences of the assembly are at least 85% identical. In step 770, the remaining sequences are put into a working database of sequences.

This method helps to filter down the number of sequences to scan afterwards. The use of the cluster allows building a working database with sequences that have any of the characteristics of not coding for a gene, not over represented in the two compared genomes, sufficient length, or have at least 85% identity.

F. Analyzing Secondary Structure of Resulting Sequences

In one embodiment, the secondary structures of sequences in the list of candidates (working database) are analyzed. A pre-microRNA transcript is a precursor RNA having a stem-loop like structure. Using the working base (WB) described before, the inventors use folding algorithms to predict secondary structures of all the sequences in the WB in the forward and in the reverse strand. The algorithm which has been used comes from the Vienna package (Hofacker I L. Vienna RNA secondary structure Nucleic Acids Res., 2003, July 1; 31(13):3429-31).

Figure 8:
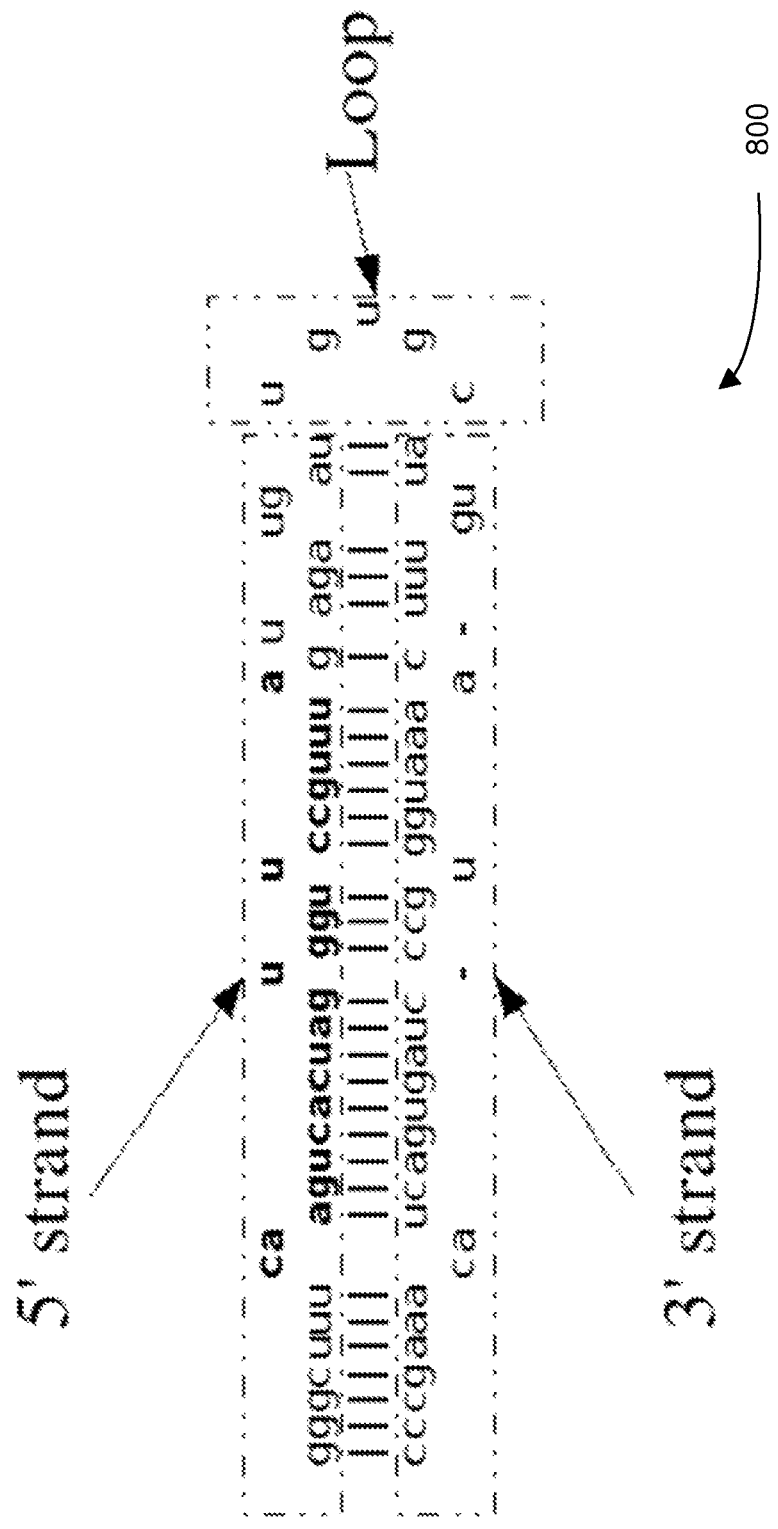
FIG. 8 illustrates a secondary structure of an exemplary sequence (SEQ ID NO: 7804) according to an embodiment of the present invention.

FIG. 8 illustrates a secondary structure 800 of an exemplary sequence. There is a 5' strand stem (arm), a 3' strand stem (arm), and a loop parts of secondary structure 800. In one aspect, the secondary structure is searched to locate a microRNA in the 5' strand stem or 3' strand end or both.

Knowing the secondary structure of a pre-microRNA, the results are parsed to find out if the sequences have a secondary structure which may correspond to the classical structure of pre-microRNA family members using an appropriate Perl script. Perl script evaluates a certain combination of criteria before accepting a sequence as a potential pre-microRNA candidate.

In one embodiment, sequences are identified that have a stem-loop secondary structure with a 5' strand (arm) stem having from 20 to 45 nucleotides and with a 3' strand stem having from 20 to 45 nucleotides. In one aspect, sequences are identified that also satisfy the following four criteria: (1) a number of nucleotides (nt) in the sequence, i.e. the pre-miRNA stem-loop; (2) a length of the loop; (3) a percent identity; and (4) a Zscore. The loop length is the length in nucleotides of the hairpin loop of the stem loop, i.e. not including arms. The percent identity is the percentage of conserved nucleotides between two sequences.

The Zscore is a statistical test. The principle of this method is to generate N random sequences having the same nucleotide composition of a given sequence. Each of these N random sequences are then folded and the Minimal Free Energy (MFE) is given. If R is the number of sequences with MFE<MFE of initial sequence, the Zscore equals R/(N+1). In one embodiment, the number of nucleotides (nt) required is 60-120 nt; the loop length is 4-15 nucleotides; and the percent identity is at least 85%.

In one embodiment, sequences with a Zscore (using N=1.000) less than 0.06 are kept. When a sequence and its reverse complement are less than 0.06, the one with the lower Zscore is kept. In one aspect, if the sequence comes from an orthologous region with less than 100% identity, the same statistical test is applied to the orthologous sequence. In another aspect, the sequence is kept, if the orthologous one is also under 0.06.

In one embodiment, four more criteria are analyzed to determine if a predetermined number (subset) of them are satisfied: (1) energy (MFE); (2) % GC; (3) % of base pairing; and (4) minimum conserved nucleotide of one arm. The "% GC" is the percentage of nucleotides G+C in a given sequence. The "% base pairing" is the number of bases which are paired between the two arms. The minimum number of conserved nucleotides of one arm (Arm conserved) is the minimum number of nucleotides, which are perfectly conserved between the two species compared in at least one arm of the stem loop. In one embodiment, the following values for the criteria are used: % GC from 30 to 51%; percentage base pairing between 30 and 40%; a Minimum Free Energy less than 25 kcal/mol; and a minimum 17 nucleotides are perfectly conserved between the two species compared in at least one arm of the stem loop. In one aspect, three of the four criteria are required to be satisfied.

Figure 9:
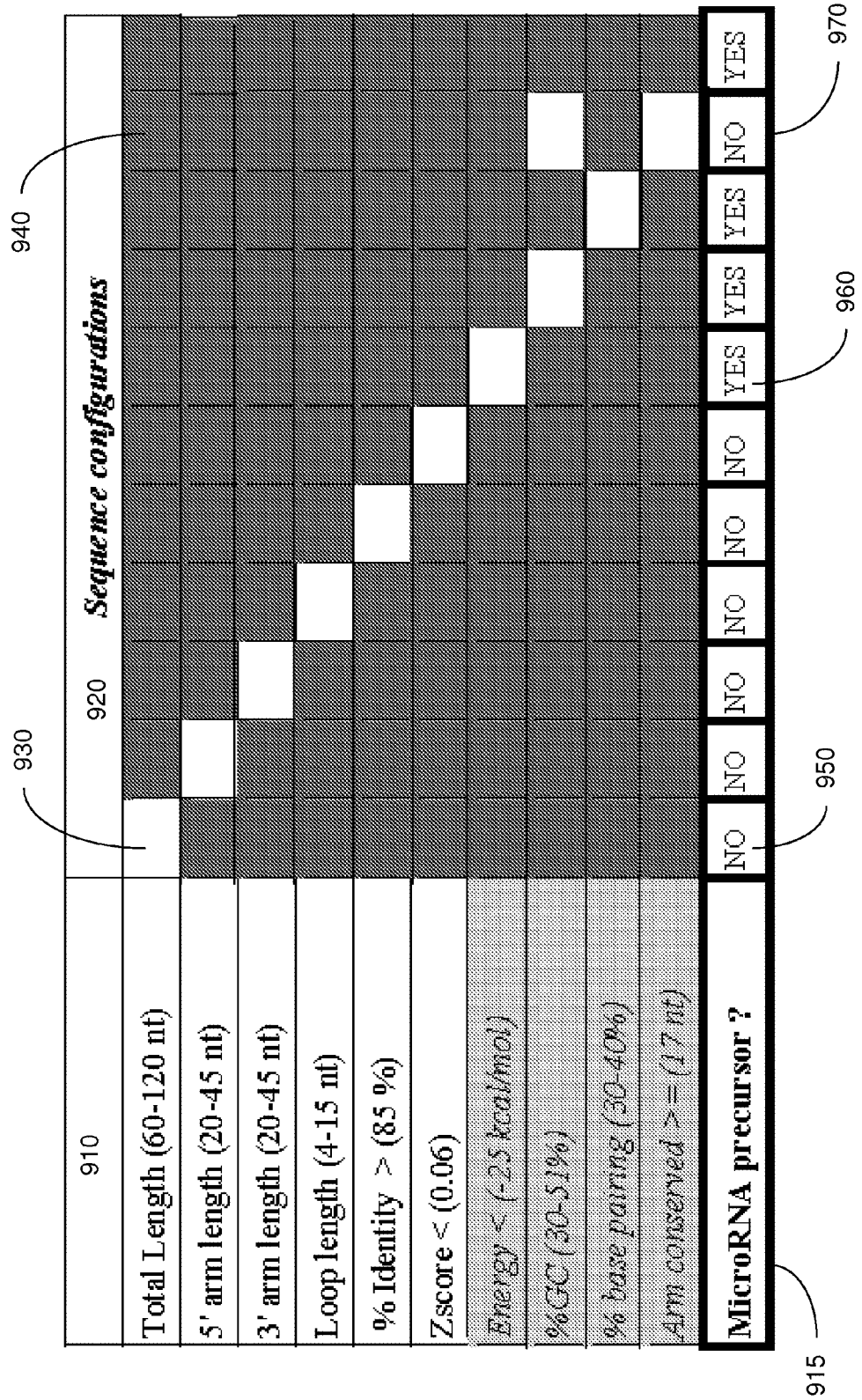
FIG. 9 illustrates a table showing the criteria and the decision of whether a sequence is a microRNA precursor candidates according to an embodiment of the present invention.

FIG. 9 illustrates a table 900 showing the criteria and the decision of whether a sequence is a microRNA precursor candidate. Column 910 lists ten different criteria. In one embodiment, each of the first six criteria (with the light background) is deemed required. The last four criteria (with a shaded background) are deemed optional, and only a subset of them are required. In one aspect, three out of the last four criteria are required. Each of columns 920 signify a sequence whose secondary structure is analyzed. Row 915 shows the decision as to whether a sequence is a candidate.

A white box 930 signifies that the criterion is not satisfied. A dark box 940 signifies that the criterion is satisfied. In one embodiment, sequence 950 is deemed to not be a candidate as the first required criteria of total length is not satisfied. In one embodiment, sequence 960 is deemed to be a candidate since only one optional criterion (energy) is not satisfied. In one embodiment, sequence 970 is deemed not to be a candidate since two optional criteria (% GC and ARM conserved) are not satisfied.

In one embodiment, when a stem-loop is found, the exact positions of the 5' strand start and the exact positions of the 3' strand end are extracted to make a new sequence. This new sequence is then folded again and the structure parsed again to see if it fits with a secondary structure corresponding to a pre-microRNA stem-loop. This is done because secondary structure may change according to the neighbouring nucleotide sequence. Genomic positions of sequences having a pre-microRNA secondary like structure are kept in the database. In one aspect, sequences are computed to find their tissue annotations by comparison with the dbEST database. FIG. 10 illustrates secondary structures of select sequences.

III. Sequences Identified by the Present Methods

A. Isolated Nucleic Acids

In one aspect, present invention provides isolated pre-microRNA nucleic acid molecules, identified by the method of the invention, selected from the group of pre-microRNA molecules consisting of the pre-microRNA molecules having the following nucleic acid sequences:

a) a nucleic RNA sequence having a DNA sequence selecting from the group consisting of the DNA sequences SEQ ID NOs. 1 to 1694 and 4035 to 5758, preferably of the DNA sequences SEQ ID NOs. 3, 5, 16, 22, 32, 34, 35, 36, 60, 70, 77, 81, 82, 90, 93, 139, 141, 151, 152, 158, 163, 170, 175, 176, 183, 184, 191, 192, 200, 205, 219, 223, 224, 248, 275, 276, 323, 328, 344, 357, 363, 366, 385, 400, 406, 407, 425, 472, 481, 489, 500, 501, 503, 512, 527, 530, 531, 563, 608, 633, 640, 651, 653, 664, 678, 728, 744, 753, 784, 785, 786, 826, 832, 858, 876, 903, 909, 911, 926, 927, 940, 942, 944, 946, 947, 951, 955, 963, 967, 975, 1055, 1060, 1083, 1118, 1129, 1137, 1145, 1160, 1161, 1166, 1173, 1174, 1175, 1198, 1205, 1207, 1217, 1233, 1238, 1251, 1267, 1299, 1321, 1323, 1343, 1352, 1396, 1403, 1429, 1485, 1531, 1545, 1547, 1559, 1586, 1592, 1601, 1610, 1611, 1617, 1634, 1645, 1649, 1653, 1656, 1661, 1667, 1681, 1686, 1688, 1693 and 4773;

b) a nucleic sequences having at least 80%, preferably at least, 85% or 90% and more preferably at least 95%, identity after optimum alignment with a sequence as defined in a);

c) a complementary sequence of a sequence as defined in a) or b);

d) a DNA molecule coding for a sequence as defined in a), b) or c); and e) a nucleic sequence having at least 12 nucleotides length, preferably 13, 14, 15, 16, 17, 18, 19, 20, 21, 22, 23, 24, 25 and 26 nucleotides length, and at most 30 nucleotides length, preferably 35, 40, 45, 50, 60, 75, 80, 90 and 100, which hybridizes under stringent conditions to a sequence as defined in a), b), c) or d).

In another aspect, present invention provides isolated microRNA nucleic acid molecules, identified by the method of the invention, selected from the group of microRNA molecules consisting of the microRNA molecules having the following nucleic acid sequences:

a) a nucleic RNA sequence having a DNA sequence selecting from the group consisting of the DNA sequences SEQ ID NOs. 1695-4004 and 5759-7803, preferably of the DNA sequences SEQ ID NOs. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2313, 2314, 2408-2410, 2427-2434, 2437, 2438, 2532, 2450, 2451, 2469-2471, 2476, 2477, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3232, 3233, 3249, 3250, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3557, 3567, 3619-3621, 3627, 3628, 3663, 3786, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994, 4001-4004;

b) a nucleic sequences having at least 80%, preferably at least, 85% or 90% and more preferably at least 95%, identity after optimum alignment with a sequence as defined in a);

c) a complementary sequence of a sequence as defined in a) or b);

d) a DNA molecule coding for a sequence as defined in a), b) or c); and e) a nucleic sequence having at least 12 nucleotides length, preferably 13, 14, 15, 16, 17, 18, 19, 20, 21, 22, 23, 24, 25 and 26 nucleotides length, and at most 30 nucleotides length, preferably 35, 40, 45, 50, 60, 75, 80, 90 and 100, which hybridizes under stringent conditions to a sequence as defined in a), b), c) or d).

In a preferred embodiment, the invention pertains to an isolated pre-microRNA nucleic acid molecule, identified by the method of the invention, selected from the group of pre-microRNA molecules consisting of the pre-microRNA molecules having the following nucleic acid sequences:

a) a nucleic acid sequence of a fragment having at least 15 consecutive nucleotides, preferably 16, 17, 18, 19, and 20 nucleotides length, and at most 24, preferably 25, 26, 27, 28, 29 and 30 nucleotides length, more preferably at least 19 and at most 24 nucleotides length, of a pre-microRNA nucleic acid sequence having a DNA sequence selecting from the group consisting of the sequences SEQ ID NOs. 1 to 1694 and 4035 to 5758, preferably of a pre-microRNA nucleic acid sequence having a DNA sequence selected from the group SEQ ID NO. 3, 5, 16, 22, 32, 34, 35, 36, 60, 70, 77, 81, 82, 90, 93, 139, 141, 151, 152, 158, 163, 170, 175, 176, 183, 184, 191, 192, 200, 205, 219, 223, 224, 248, 275, 276, 323, 328, 344, 357, 363, 366, 385, 400, 406, 407, 425, 472, 481, 489, 500, 501, 503, 512, 527, 530, 531, 563, 608, 633, 640, 651, 653, 664, 678, 728, 744, 753, 784, 785, 786, 826, 832, 858, 876, 903, 909, 911, 926, 927, 940, 942, 944, 946, 947, 951, 955, 963, 967, 975, 1055, 1060, 1083, 1118, 1129, 1137, 1145, 1160, 1161, 1166, 1173, 1174, 1175, 1198, 1205, 1207, 1217, 1233, 1238, 1251, 1267, 1299, 1321, 1323, 1343, 1352, 1396, 1403, 1429, 1485, 1531, 1545, 1547, 1559, 1586, 1592, 1601, 1610, 1611, 1617, 1634, 1645, 1649, 1653, 1656, 1661, 1667, 1681, 1686, 1688, 1693 and 4773;

b) a nucleic acid sequence having at least 80%, preferably at least, 85% or 90% and more preferably at least 95%, identity after optimum alignment with a sequence as defined in a);

c) a complementary sequence of a sequence as defined in a) or b);

d) a DNA molecule coding for a sequence as defined in a), b) or c); and e) a nucleic acid sequence having at least 12 nucleotides length, preferably 13, 14, 15, 16, 17, 18, 19, 20, 21, 22, 23, 24, 25 and 26 nucleotides length, and at most 30 nucleotides length, preferably 35, 40, 45, 50, 75 and 100, which hybridizes under stringent conditions to a sequence as defined in a), b), c) or d).

In another embodiment, the isolated microRNA nucleic acid molecule according to the present invention is selected from the group of microRNA molecules consisting of the microRNA molecules having the following nucleic acid sequences:

a) a nucleic sequence of a fragment having at least 15 consecutive nucleotides, preferably 16, 17, 18, 19, and 20 nucleotides length, and at most 24, preferably, 25, 26, 27, 28, 29 and 30 nucleotides length, more preferably at least 19 and at most 24 nucleotides length, of a pre-microRNA nucleic acid sequence having a DNA sequence selected from the group of the sequences SEQ ID NOs. 1 to 1694 and 4035 to 5758, said fragment further having at least 10 consecutive nucleotides of a microRNA nucleic acid sequence having a DNA sequence selected from the group of the sequences SEQ ID NOs. 1695-4004 and 5759-7803, preferably of the microRNA nucleic acid sequences having a DNA sequence selected from the group consisting of SEQ ID NOs. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2313, 2314, 2408-2410, 2427-2434, 2437, 2438, 2532, 2450, 2451, 2469-2471, 2476, 2477, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3232, 3233, 3249, 3250, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3557, 3567, 3619-3621, 3627, 3628, 3663, 3786, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994, 4001-4004;

b) an RNA sequence having a DNA sequence selected from the group of the sequences SEQ ID NOs. SEQ ID NOs. 1695-4004 and 5759-7803, preferably of the microRNA nucleic acid sequences having a DNA sequence selected from the group consisting of SEQ ID NOs. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2313, 2314, 2408-2410, 2427-2434, 2437, 2438, 2532, 2450, 2451, 2469-2471, 2476, 2477, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3232, 3233, 3249, 3250, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3557, 3567, 3619-3621, 3627, 3628, 3663, 3786, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994, 4001-4004;

c) a nucleic sequence having at least 80%, preferably of at least 85% or 90% and more preferably of at least 95%, identity after optimum alignment with a sequence as defined in a) or b);

d) a complementary sequence of a sequence as defined in a), b) or c);

e) a DNA molecule coding for a sequence as defined in a), b), c) or d); and f) a nucleic sequence having at least 12 nucleotides length, preferably 13, 14, 15, 16, 17, 18, 19, 20, 21, 22, 23, 24, 25 and 26 nucleotides length, and at most 30 nucleotides length, preferably 35, 40, 45, 50, 75 and 100, which hybridizes under stringent conditions to a sequence as defined in a), b), c), d) or e).

By "a nucleic RNA, microRNA or pre-microRNA sequence having a DNA sequence selecting from the group", it is intended to designate the RNA nucleic acid having the referenced DNA sequence wherein each thymine base has been replaced by an uracile base.

By "a DNA molecule coding for a sequence as defined in a)", it is intended to designate the DNA nucleic acid sequence having the DNA sequence formulated in a), or having the referenced RNA sequence wherein each uracile base has been replaced by a thymine base.

It should be understood that the invention does not relate to nucleic sequences or in a natural form, that is to say that they are not taken in their natural environment but that they can be obtained by purification from natural sources, or alternatively obtained by genetic recombination, or alternatively by chemical synthesis.

Nucleic sequence or nucleic acid is understood to mean an isolated natural, or a synthetic, DNA and/or RNA fragment comprising, natural or non-natural nucleotides, designating a precise succession of nucleotides, non-modified or modified, allowing a fragment, a segment or a region of a nucleic acid to be defined.

The isolated nucleic acid molecules according to the present invention which can be in a single stranded, partially double stranded or double stranded form.

B. Solid Supports

In another aspect, the present invention provides solid supports, that can be used for the detection and/or the quantification of the expression of a pre-microRNA, microRNA, or derived nucleic acid thereof, of the present invention.

In one embodiment, the solid support is characterized in that it comprises binding to said support at least:

a)—a nucleic acid having at least 15 consecutive nucleotides, preferably 16, 17, 18, 19, and 20 nucleotides length, and at most 24, preferably, 25, 26, 27, 28, 29 and 30 nucleotides length, more preferably at least 19 and at most 24 nucleotides length, of a fragment of nucleic acid sequence selected from the group of the sequences SEQ ID NOs. 1 to 1694 and 4035 to 5758, preferably a nucleic sequence of a fragment having at least 15 consecutive nucleotides, preferably 16, 17, 18, 19, and 20 nucleotides length, and at most 24, preferably, 25, 26, 27, 28, 29 and 30 nucleotides length, more preferably at least 19 and at most 24 nucleotides length, of the nucleic sequences SEQ ID NO. 3, 5, 16, 22, 32, 34, 35, 36, 60, 70, 77, 81, 82, 90, 93, 139, 141, 151, 152, 158, 163, 170, 175, 176, 183, 184, 191, 192, 200, 205, 219, 223, 224, 248, 275, 276, 323, 328, 344, 357, 363, 366, 385, 400, 406, 407, 425, 472, 481, 489, 500, 501, 503, 512, 527, 530, 531, 563, 608, 633, 640, 651, 653, 664, 678, 728, 744, 753, 784, 785, 786, 826, 832, 858, 876, 903, 909, 911, 926, 927, 940, 942, 944, 946, 947, 951, 955, 963, 967, 975, 1055, 1060, 1083, 1118, 1129, 1137, 1145, 1160, 1161, 1166, 1173, 1174, 1175, 1198, 1205, 1207, 1217, 1233, 1238, 1251, 1267, 1299, 1321, 1323, 1343, 1352, 1396, 1403, 1429, 1485, 1531, 1545, 1547, 1559, 1586, 1592, 1601, 1610, 1611, 1617, 1634, 1645, 1649, 1653, 1656, 1661, 1667, 1681, 1686, 1688, 1693, 4773;

or a nucleic sequence of a fragment having at least 15 consecutive nucleotides, preferably 16, 17, 18, 19, and 20 nucleotides length, and at most 24, preferably, 25, 26, 27, 28, 29 and 30 nucleotides length, more preferably at least 19 and at most 24 nucleotides length, of the sequences SEQ ID NOs. 1695 to 4004 and 5759 to 7803, preferably a nucleic sequence of a fragment having at least 15 consecutive nucleotides, preferably 16, 17, 18, 19, and 20 nucleotides length, and at most 24, preferably, 25, 26, 27, 28, 29 and 30 nucleotides length, more preferably at least 19 and at most 24 nucleotides length, of the nucleic sequences SEQ ID NOs. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2313, 2314, 2408-2410, 2427-2434, 2437, 2438, 2532, 2450, 2451, 2469-2471, 2476, 2477, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3232, 3233, 3249, 3250, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3557, 3567, 3619-3621, 3627, 3628, 3663, 3786, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994, 4001-4004;

b) one nucleic acid having at least 80%, preferably of at least 85% or 90% and more preferably of at least 95%, identity after optimum alignment with a nucleic acid as defined in a); or c) one nucleic acid having a complementary sequence of a nucleic acid as defined in a) or b); or d) a RNA nucleic acid having a DNA nucleic acid as defined in a), b) or c); or e) a nucleic acid having at least 15 nucleotides length which hybridizes under stringent conditions to a nucleic acid as defined in a), b), c) or d).

In another preferred embodiment, the solid supports of the present invention is characterized in that it comprises binding to said support at least one nucleic acid selected from the group consisting of the oligonucleotide probes depicted in Table 3, preferably at least one oligonucleotide probe corresponding to a positive control and at least one different oligonucleotide probe corresponding to a negative control for the type of tissue or cell which is desired to be tested for expression of certain pre-micro RNAs or microRNAs (see Example 3 below).

In a further preferred embodiment, the solid support is characterized in that it comprises binding to said support at least 3418 nucleic acids, wherein these 3418 nucleic acids are:

for each nucleic acid sequence SEQ ID NOs. 1 to 1694 and SEQ ID NOs. 4035 to 5758, a) a nucleic sequence of a fragment having at least 15 consecutive nucleotides, preferably 16, 17, 18, 19, and 20 nucleotides length, and at most 24, preferably, 25, 26, 27, 28, 29 and 30 nucleotides length, more preferably at least 19 and at most 24 nucleotides length, of said sequence SEQ ID NOs. 1 to 1694 and 4035 to 5758, preferably of the sequences SEQ ID NOs. 1695 to 4004 and 5759 to 7803; or b) a nucleic acid having at least 80%, preferably of at least 85% or 90% and more preferably of at least 95%, identity after optimum alignment with a nucleic acid as defined in a); or c) a nucleic acid having a complementary sequence of an acid nucleic as defined in a) or b); or d) a RNA nucleic acid having a DNA nucleic acid sequence as defined in a), b) or c); or e) a nucleic sequence which hybridizes under stringent conditions to a nucleic acid as defined in a), b), c) or d).

In another aspect, the present invention provides solid supports comprising at least 5 pre-microRNA and/or microRNA capture sequences, wherein the capture sequences are at least 15 nucleotides in length and have substantial sequence complementarity to a pre-microRNA or microRNA identified by the methods of the invention. In some embodiments, the capture sequences are at least about 13, 14, 15, 16, 17, 18, 19, 20, 21, 22, 23, 24, 25, 26, 28, 30, 35 or 40 nucleotides in length. The nucleotides can be DNA, RNA, peptide nucleic acids ("PNA"), or analogs thereof. The capture nucleic acids can comprise one or more non-naturally occurring nucleotide bases. In some embodiements, the capture sequences having substantial complementarity have at least 93% (i.e., 1 mismatch in 15 nucleotides), 94%, 95%, 96%, 97%, 98%, or 99% sequence complementarity to a pre-microRNA or microRNA identified by the methods of the invention.

In some embodiments, the solid support comprises 5 or more capture sequences having substantial complementarity or 100% sequence complementarity to a pre-microRNA selected from the group consisting of SEQ ID NOs. 1-1694, 4035-5758, and the complements thereof. In some embodiments, the solid support comprises 5 or more capture sequences have substantial complementarity or 100% sequence complementarity to a microRNA selected from the group consisting of SEQ ID NOs. 1695-4004, 5759-7803, and the complements thereof. In another embodiment, the solid support comprises 5 or more capture sequences have substantial complementarity or 100% sequence complementarity to a microRNA probe selected from the group consisting of SEQ ID NOs. 4005-4034, and the complements thereof.

In one embodiment, the solid support comprises 5 or more pre-microRNA capture sequences having 100% sequence complementarity to a pre-microRNA selected from the group consisting of SEQ ID NOs. 3, 5, 16, 22, 32, 34, 35, 36, 60, 70, 77, 81, 82, 90, 93, 139, 141, 151, 152, 158, 163, 170, 175, 176, 183, 184, 191, 192, 200, 205, 219, 223, 224, 248, 275, 276, 323, 328, 344, 357, 363, 366, 385, 400, 406, 407, 425, 472, 481, 489, 500, 501, 503, 512, 527, 530, 531, 563, 608, 633, 640, 651, 653, 664, 678, 728, 744, 753, 784, 785, 786, 826, 832, 858, 876, 903, 909, 911, 926, 927, 940, 942, 944, 946, 947, 951, 955, 963, 967, 975, 1055, 1060, 1083, 1118, 1129, 1137, 1145, 1160, 1161, 1166, 1173, 1174, 1175, 1198, 1205, 1207, 1217, 1233, 1238, 1251, 1267, 1299, 1321, 1323, 1343, 1352, 1396, 1403, 1429, 1485, 1531, 1545, 1547, 1559, 1586, 1592, 1601, 1610, 1611, 1617, 1634, 1645, 1649, 1653, 1656, 1661, 1667, 1681, 1686, 1688, 1693 and 4773, and the complements thereof.

In another embodiment, the solid support comprises 5 or more microRNA capture sequences having 100% sequence complementarity to a microRNA selected from the group consisting of SEQ ID NOs. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2313, 2314, 2408-2410, 2427-2434, 2437, 2438, 2532, 2450, 2451, 2469-2471, 2476, 2477, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3232, 3233, 3249, 3250, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3557, 3567, 3619-3621, 3627, 3628, 3663, 3786, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994, 4001-4004, and the complements thereof.

In some embodiments, the solid support comprises at least 10, 25, 50, 96, 100, 192, 200, 384, 500, 768, 1000, 1536 or more capture nucleic acids based on the pre-microRNA and microRNA nucleic acid sequences identified by the present methods.

In some embodiments, the solid support is a nucleic acid (DNA, RNA, PNA, and analogs thereof) chip array, for example, for detection and/or the quantification of the expression of a pre-microRNA, microRNA, or derived nucleic acid thereof, of the present invention. DNA chip arrays are well known in the art and are commercially available, for example, from Affymetrix (GeneChip) or Hyseq (HyChip and HyGnostics). The chips can be made from silica, glass, metals, plastic polymers, ceramic, or any other appropriate material or materials.

C. Methods of Detection

In another aspect, the present invention is directed to methods of detecting pre-microRNA or microRNA in a cell, comprising conducting multiplex polymerase chain reaction (PCR) to amplify at least 5 target pre-microRNA or microRNA nucleic acid sequences using forward primers and reverse primers, wherein each forward and reverse primer pair member is complementary to at least 15 contiguous nucleotides of a nucleic acid sequence selected from the group consisting of SEQ ID NOs: 1-1694 and 4035-5758, and the complements thereof. In some embodiments, each forward and reverse primer pair member is complementary to at least 15 contiguous nucleotides of a nucleic acid sequence selected from the group consisting of SEQ ID NOs: 1695-4004 and 5759-7803. In some embodiments, at least 5, 6, 7, 8, 9, 10, 15, 20, 25, 30, 50, 100 or more pre-microRNA and/or microRNA nucleic acid sequences are amplified using multiplex PCR.

Multiplex PCR reaction is intended to designate a PCR reaction where more than one primer set is included in the reaction pool allowing 2 or more different DNA targets to be amplified by PCR in a single reaction tube. Multiplex PCR can be quantitative and can be evaluated "real-time." Multiplex PCR reactions are useful for validation, diagnostic and prognostic purposes.

Multiplex PCR reactions can be carried out using manual or automatic thermal cycling. Any commercially available thermal cycler may be used, such as, e.g., Perkin-Elmer 9600 cycler.

The reaction products obtained by multiplex PCR reaction can be analyzed using any of several methods that are well-known in the art, such as, e.g.:
  DNA chip comprising on the solid support the corresponding pre-microRNA or microRNA nucleic acid capture sequences;
  agarose gel electrophoresis. For this method, it is preferred that the different amplified sequences are of distinct sizes and thus can be resolved in a single gel;
  dot-blot hybridization with specific oligonucleotides; or
  SSCP method ("Single Stranded Conformational Polymorphism") which can distinguish similar sized DNA fragments according to the mobility of the single-stranded DNA under polyacrylamide gel electrophoresis.

For example, multiplex PCR reactions can be carried out, e.g., in a volume of 100 µl reaction mixtures containing e.g. 2 µg of DNA sample in 1×PCR buffer (10 mM Tris-HCl, pH 8.3, 50 mM KCl, 1.5 mM $MgCl_2$), 200 µM dNTPs, and 25-100 U/ml Taq polymerase (Perkin-Elmer, Norwalk, Conn.). Primer concentrations can be ranged from 0.25 to 1.0 µM. Amplifications were carried out using a Perkin-Elmer 9600 thermocycler (Perkin-Elmer, Norwalk, Conn.) for 28 cycles with ramping (melting at 94° C. for 10 s, annealing at 50° C., 55° C., 60° C. or 65° C. for 10 s, and extension at 72° C. for 10 s). The concentration of each primer in the reaction mixture can be ranged from about 0.05 to about 4 µM. The optimal concentration for primer can be evaluated by performing single PCR reactions using each primer pair individually. Similarly, each primer pair can be evaluated independently to confirm that all primer pairs to be included in a single multiplex PCR reaction require the same amplification conditions (i.e., temperature, duration of annealing and extension steps).

After completion of the reaction, e.g. 8 µl of the reaction products can be loaded directly onto a 2% ethidium bromide-stained agarose gel and subjected to electrophoresis at 250 volts for 90 minutes. The amplification products can be visualized with a UV transilluminator and photographed.

When multiplex PCR reaction is used for identifying the presence of specific DNA from a sample initially containing RNA, the multiplex PCR method comprises a prior step of incubating said RNA sample with a reverse transcriptase under conditions effective to produce a single-stranded DNA or cDNA from each RNA or mRNA the presence of which is desired to be tested.

In one embodiment of the method of detecting pre-microRNA or microRNA in a cell, comprising conducting multiplex PCR according to the present invention, said at least 5 target pre-microRNA or microRNA nucleic acid sequences which are amplified are pre-microRNA nucleic acid sequences selected from the group consisting of SEQ ID NOs: 1-1694 and 4035-5758.

In a further embodiment, the detection methods comprise the step of amplifying at least 5 pre-microRNA nucleic acid sequences selected from the group consisting of SEQ ID NOs. 3, 5, 16, 22, 32, 34, 35, 36, 60, 70, 77, 81, 82, 90, 93, 139, 141, 151, 152, 158, 163, 170, 175, 176, 183, 184, 191, 192, 200, 205, 219, 223, 224, 248, 275, 276, 323, 328, 344, 357, 363, 366, 385, 400, 406, 407, 425, 472, 481, 489, 500, 501, 503, 512, 527, 530, 531, 563, 608, 633, 640, 651, 653, 664, 678, 728, 744, 753, 784, 785, 786, 826, 832, 858, 876, 903, 909, 911, 926, 927, 940, 942, 944, 946, 947, 951, 955, 963, 967, 975, 1055, 1060, 1083, 1118, 1129, 1137, 1145, 1160, 1161, 1166, 1173, 1174, 1175, 1198, 1205, 1207, 1217, 1233, 1238, 1251, 1267, 1299, 1321, 1323, 1343, 1352, 1396, 1403, 1429, 1485, 1531, 1545, 1547, 1559, 1586, 1592, 1601, 1610, 1611, 1617, 1634, 1645, 1649, 1653, 1656, 1661, 1667, 1681, 1686, 1688, 1693 and 4773.

In another embodiment, the methods comprise the step of amplifying at least 5 microRNA nucleic acid sequences selected from the group consisting of SEQ ID NOs: 1695-4004 and 5759-7803.

In a further embodiment, the methods comprise the step of amplifying at least 5 microRNA nucleic acid sequences selected from the group consisting of SEQ ID NOs. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2389, 2390, 2399, 2313, 2314, 2408-2410, 2427-2434, 2437, 2438, 2450, 2451, 2469-2471, 2476, 2477, 2523, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3249, 3250, 3261, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3560, 3567, 3619-3621, 3627, 3628, 3663, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994 and 4001-4004.

In a particular aspect, multiplex PCR is carried out for establishing pre-microRNA and/or microRNA expression profile in certain normal and pathologic tissue or cells:
  In prostate cells or tissue,
    the method comprises the step of amplifying at least 5 pre-microRNA nucleic acid sequences expressed by the prostate tissue, wherein said at least 5 pre-microRNA nucleic acid sequences are selected from the group consisting of SEQ ID NO. 3, 22, 32, 34, 90, 139, 163, 176, 248, 276, 328, 406, 472, 481, 407, 531, 608, 653, 678, 728, 785, 903, 926, 947, 963, 1055, 1118, 1137, 1173, 1174, 1196, 1198, 1485, 1531, 1159, 1592, 1601, 1656, 1667 and 1693; and/or
    the method comprises the step of amplifying at least 5 microRNA nucleic acid sequences expressed by the prostate tissue, wherein said at least 5 microRNA nucleic acid sequences are selected from the group consisting of SEQ ID NO. 1697, 1698, 1730-1732, 1744-1746, 1837-1839, 1896, 1897, 1933, 1934, 1952-1954, 2068, 2111, 2180, 2181, 2389, 2390, 2399, 2477, 2532, 2584-2587, 2730, 2811-2813, 2958-2961, 2999, 3025-

3027, 3048-3050, 3232, 3233, 3261, 3320-3325, 3363, 3558-3560, 3825, 3870, 3871, 3880-3882, 3959, 3960, 3973-3976 and 4001-4003.

In testes cells or tissue,
the method comprises the step of amplifying at least 5 pre-microRNA nucleic acid sequences expressed by the testes tissue, wherein said at least 5 pre-microRNA nucleic acid sequences are selected from the group consisting of SEQ ID NO. 36, 139, 205, 223, 328, 363, 406, 500, 563, 911, 946, 963, 1055, 1173, 1175, 1205, 1352, 1611 and 4773; and/or the method comprises the step of amplifying at least 5 microRNA nucleic acid sequences expressed by the testes tissue, wherein said at least 5 microRNA nucleic acid sequences are selected from the group consisting of SEQ ID NO.1749, 1750, 1896, 1897, 2000-2002, 2025, 2180, 2181, 2228, 2229, 2427-2430, 2523, 2971-2974, 3023, 3024, 3048-3050, 3320-3322, 3326-3329, 3372-3375, 3567 and 4004.

In muscle cells or tissue,
the method comprises the step of amplifying at least 5 pre-microRNA nucleic acid sequences expressed by the muscle tissue, wherein said at least 5 pre-microRNA nucleic acid sequences are selected from the group consisting of SEQ ID NO.3, 22, 32, 139, 163, 176, 328, 363, 472, 678, 728, 832, 947, 963, 1173, 1174, 1198, 1656 and 1693; and/or the method comprises the step of amplifying at least 5 microRNA nucleic acid sequences expressed by the muscle tissue, wherein said at least 5 microRNA nucleic acid sequences are selected from the group consisting of SEQ ID NO. 1697, 1698, 1730-1732, 1744, 1745, 1896, 1897, 1933, 1934, 1952-1954, 2180, 2181, 2228, 2229, 2389, 2390, 2730, 2872, 3048-3050, 3322-3325, 3363, 3959, 3960 and 4001-4003.

In liver cells or tissue,
the method comprises the step of amplifying at least 5 pre-microRNA nucleic acid sequences expressed by the liver tissue, wherein said at least 5 pre-microRNA nucleic acid sequences are selected from the group consisting of SEQ ID NO. 139, 328, 363, 728, 963, 1083 and 1173; and/or the method comprises the step of amplifying at least 5 microRNA nucleic acid sequences expressed by the liver tissue, wherein said at least 5 microRNA nucleic acid sequences are selected from the group consisting of SEQ ID NO. 1896, 2180, 2181, 2228, 2229, 2730, 2872, 3048-3050, 3189 and 3322.

In bone marrow cells or tissue,
the method comprises the step of amplifying at least 5 pre-microRNA nucleic acid sequences expressed by the bone marrow tissue, wherein said at least 5 pre-microRNA nucleic acid sequences are selected from the group consisting of SEQ ID NO.35, 328, 357, 363, 728, 963 and 1173; and/or the method comprises the step of amplifying at least 5 microRNA nucleic acid sequences expressed by bone marrow tissue, wherein said at least 5 microRNA nucleic acid sequences are selected from the group consisting of SEQ ID NO. 1747, 1748, 2180, 2181, 2219-2221, 2228, 2229, 2730, 3048-3050 and 3320-3322.

In kidney cells or tissue,
the method comprises the step of amplifying at least 5 pre-microRNA nucleic acid sequences expressed by the kidney tissue, wherein said at least 5 pre-microRNA nucleic acid sequences are selected from the group consisting of SEQ ID NO.139, 223, 328, 363, 728, 946, 963 and 1205; and/or the method comprises the step of amplifying at least 5 microRNA nucleic acid sequences expressed by kidney tissue, wherein said at least 5 microRNA nucleic acid sequences are selected from the group consisting of SEQ ID NO. 1896, 1897, 2025, 2026, 2180, 2181, 2228, 2229, 2730, 3023, 3024, 3048-3050 and 3372-3375.

In heart or brain cells or tissue,
the method comprises the step of amplifying at least 5 pre-microRNA nucleic acid sequences expressed by the heart or brain tissue, wherein said at least 5 pre-microRNA nucleic acid sequences are selected from the group consisting of SEQ ID NO. 139, 328, 728, 832, 858, 963 and 1173; and/or the method comprises the step of amplifying at least 5 microRNA nucleic acid sequences expressed by kidney tissue, wherein said at least 5 microRNA nucleic acid sequences are selected from the group consisting of SEQ ID NO. 1896, 1897, 2180, 2181, 2730, 2872, 2900, 3048-3050 and 3322.

In sperm cells or tissue,
the method comprises the step of amplifying at least 5 pre-microRNA nucleic acid sequences expressed by the sperm tissue, wherein said at least 5 pre-microRNA nucleic acid sequences are selected from the group consisting of SEQ ID NO.328, 363, 728, 926, 963 and 1173; and/or the method comprises the step of amplifying at least 5 microRNA nucleic acid sequences expressed by sperm tissue, wherein said at least 5 microRNA nucleic acid sequences are selected from the group consisting of SEQ ID NO. 2180, 2181, 2228, 2229, 2730, 2999, 3048-3050 and 3320-3322.

In spleen cells or tissue,
the method comprises the step of amplifying at least 5 pre-microRNA nucleic acid sequences expressed by the spleen tissue, wherein said at least 5 pre-microRNA nucleic acid sequences are selected from the group consisting of SEQ ID NO.139, 328, 363, 728 and 963; and/or the method comprises the step of amplifying at least 5 microRNA nucleic acid sequences expressed by spleen tissue, wherein said at least 5 microRNA nucleic acid sequences are selected from the group consisting of SEQ ID NO. 1896, 1897, 2180, 2181, 2228, 2229, 2730 and 3048-3050.

In thymus cells or tissue,
the method comprises the step of amplifying at least 5 pre-microRNA nucleic acid sequences expressed by the thymus tissue, wherein said at least 5 pre-microRNA nucleic acid sequences are selected from the group consisting of SEQ ID NO.139, 328, 363, 728, 963 and 1173; and/or the method comprises the step of amplifying at least 5 microRNA nucleic acid sequences expressed by thymus tissue, wherein said at least 5 microRNA nucleic acid sequences are selected from the group consisting of SEQ ID NO. 1896, 1897, 2180, 2181, 2228, 2229, 2730, 3048-3050 and 3320-3322.

In lung cells or tissue,
the method comprises the step of amplifying at least 5 microRNA nucleic acid sequences expressed by lung tissue, wherein said at least 5 microRNA nucleic acid sequences are selected from the group consisting of SEQ ID NO. 2870-2872 and 3048-3050.

In thymocytes cells,
the method comprises the step of amplifying at least 5 microRNA nucleic acid sequences expressed by thymocytes, wherein said at least 5 microRNA nucleic acid sequences are selected from the group consisting of SEQ ID NO. 1896, 1897, 2180, 2181, 2730 and 3048-3050.

In colon cells or tissue,
the method comprises the step of amplifying at least 5 microRNA nucleic acid sequences expressed by colon tissue, wherein said at least 5 microRNA nucleic acid sequences are selected from the group consisting of SEQ ID NO. 2180, 2181, 2228, 2229 and 3048-3050.

In blood cells or tissue,
the method comprises the step of amplifying at least 5 pre-microRNA nucleic acid sequences expressed by the blood tissue, preferably by the T cells, wherein said at least 5 pre-microRNA nucleic acid sequences are selected from the group consisting of SEQ ID NO. 3, 5, 16, 22, 32, 34, 35, 36, 60, 70, 77, 81, 82, 90, 93, 139, 141, 151, 152, 158, 163, 170, 175, 176, 183, 184, 191, 192, 200, 219, 223, 224, 248, 275, 276, 323, 328, 344, 363, 366, 385, 400, 425, 489, 500, 501, 503, 512, 527, 530, 531, 633, 640, 651, 653, 664, 678, 728, 744, 753, 784, 786, 826, 876, 903, 909, 911, 926, 927, 940, 942, 944, 947, 951, 955, 963, 967, 975, 1055, 1060, 1129, 1145, 1160, 1161, 1166, 1173, 1174, 1198, 1205, 1207, 1217, 1233, 1238, 1251, 1267, 1299, 1321, 1323, 1343, 1396, 1403, 1485, 1545, 1547, 1586, 1592, 1610, 1617, 1634, 1645, 1649, 1653, 1656, 1661, 1667, 1681, 1686, 1688, 1693, 4773; and/or
the method comprises the step of amplifying at least 5 microRNA nucleic acid sequences expressed by the blood tissue, preferably by the T cells, wherein said at least 5 microRNA nucleic acid sequences are selected from the group consisting of SEQ ID NO. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2313, 2314, 2408-2410, 2427-2434, 2437, 2438, 2532, 2450, 2451, 2469-2471, 2476, 2477, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3232, 3233, 3249, 3250, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3557, 3567, 3619-3621, 3627, 3628, 3663, 3786, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994, 4001-4004.

Efficient access to the presence of microRNA in a biological sample can be obtained through for example a basic structure comprising high-density arrays of probes attached to a solid support (the chip) at selected positions. Each DNA chip can contain thousands to millions of individual synthetic DNA probes arranged in a grid-like pattern and miniaturized to the size of a dime.

In addition, the present invention provides the nucleic acids of the present invention as markers specific to human disease.

According to another embodiment, the present invention provides the use of a nucleic acid of the present invention as a marker for determining the onset/development of a human disease.

In a preferred embodiment, present invention to provide a method for the identification and characterization of an association between the presence or the quantity of a microRNA of the present invention and a trait.

The method of detecting an association between the presence or the quantity of a microRNA, or derived acid nucleic thereof or derived pre-microRNA thereof, of the present invention and a trait (or a phenotype), comprising the steps of:
a) determining the presence or the quantity of a microRNA of the present invention in trait positive population according to a method of the invention;
b) determining the presence or the quantitty of a microRNA of the present invention in a control population; and
c) determining whether a statistically significant association exists between said presence, or said quantity, and said trait.

For example, a trait+ population suffering from a disease involving the modulation of the expression of the protein encoded by the microRNA of the present invention.

The terms "trait" or "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to a disease involving the gene whose mRNA is one of the target mRNA of the microRNA of the present invention.

The general strategy to perform association studies is to scan two group of individuals (trait+ and trait- control individuals which are characterized by a well defined phenotype as described below) in order to measure and statistically compare the presence or said quantity of such microRNA in both groups.

The invention also encompasses methods of determining whether a subject is at risk of developing a disease, comprising the steps of:
a) determining the presence or the quantity of a microRNA, or derived acid nucleic thereof or derived pre-microRNA thereof, of the present invention in the subject to be tested;
b) compare the results obtained in step a) to the presence or the quantity of said microRNA obtained to a control population; and
c) determining whether the presence or the quantity of a microRNA between said subject and the control is significant of a risk of developing said.

In another aspect, the present invention is directed to the use of a nucleic acid of the invention as a marker for the identification and/or the quantification of the presence of microRNA nucleic acid molecule, or derived pre-microRNA thereof, according to the present invention in a biological sample from an eukaryotic organism, preferably a mammal subject.

By derived pre-microRNA of microRNA nucleic acid molecule, it is intended to designate the pre-microRNA nucleic acid from which said microRNA is originated, as indicated in the numeric identifier <223> for each microRNA sequence of the invention (see the sequence listing). Are also intended to included in the wording "derived pre-microRNA thereof", the complementary and the sequences having at least 80% identity with said pre-RNA sequence identified under the identifier <223> in the sequence listing for each identified microRNA sequence of the present invention.

The term "mammals subject" includes particularly humans, dogs, cows, horses, kangaroos, pigs, sheep, goats, cats, mice, rabbits, rats, and transgenic non-human animals, preferably human.

It also provides an improved method and system for detection of the expression of novel oligonucleotides of the present invention, which modulate these target genes. In many cases the target genes may be known and fully characterized, however in alternative embodiments of the present invention, unknown or less well characterized genes may be targeted.

Preferably by microRNA nucleic acid molecule, or derivated pre-microRNA thereof, as marker according to the present invention, it is intended to designate the microRNA nucleic acid molecule of the invention or its pre-microRNA, also including their derived sequences such as fragment having at least 15 consecutive nucleotides thereof, nucleic acid having at least 80% identity, nucleic acid having a complementary sequence thereof, DNA nucleic acid coding therefore or nucleic sequence which hybridizes with these sequences as defined above for the microRNA and pre-microRNA nucleic acid molecule according to the present invention.

Samples for use in the assays of the invention when originating from mammal can be obtained by standard methods including venous puncture and surgical biopsy.

So, the present invention pertains to a method in vitro for the identification and/or the quantification of the presence microRNA nucleic acid molecule, or derived pre-microRNA thereof, in a biological sample from an eukaryotic organism, preferably from mammal, human being the most preferred, wherein said method comprises the use of a microRNA or a derived sequence thereof according to the present invention.

All the standard methods well known from a skilled person for the detection and/or the quantification of a target RNA nucleic acid in a biological sample can be used for the method of the present invention.

As described in more detail below, RT-PCR, quantitative RT-PCR, multiplex PCR methods can be used to detect or quantify the target microRNA, or derived pre-microRNA thereof.

For example, in vitro techniques for detection of target microRNA include Northern hybridizations and in situ hybridizations.

In a preferred embodiment, the invention relates to the methods according to the present invention, wherein the target microRNA, or derived pre-microRNA thereof, has a microRNA sequence as identified above for the microRNA molecule of the present invention.

When the methods according to the present invention are based to the detection or the quantification of target microRNA, or derived pre-microRNA thereof, it is also preferred that the determination of the presence, or the level, or the absence of target microRNA comprises a step of amplifying target microRNA or the cDNA coding therefore.

As used herein, the term "cDNA" shall refer to the DNA copy of the microRNA or from the pre-microRNA.

It is also preferred that the step of amplifying target microRNA or cDNA is performed by PCR (or PCR-like) or RT-PCR reaction.

"PCR" describes a method of gene amplification which involves sequenced-based hybridization of primers to specific genes within a DNA sample and subsequent amplification involving multiple rounds of annealing, elongation and denaturation using a heat-stable DNA polymerase.

"RT-PCR" is an abbreviation for reverse transcriptase-polymerase chain reaction. Subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase.

"PCR-like" will be understood to mean all methods using direct or indirect reproductions of nucleic acid sequences, or alternatively in which the labeling systems have been amplified, these techniques are of course known, in general they involve the amplification of DNA by a polymerase; when the original sample is an RNA, it is advisable to carry out a reverse transcription beforehand. There are currently a great number of methods allowing this amplification, for example the so-called NASBA "Nucleic Acid Sequence Based Amplification", TAS "Transcription based Amplification System", LCR "Ligase Chain Reaction", "Endo Run Amplification" (ERA), "Cycling Probe Reaction" (CPR), and SDA "Strand Displacement Amplification", methods well known to persons skilled in the art.

In a more preferred embodiment, the invention pertains to the methods according to the present invention, wherein the primer or pair of primers used for the PCR or RT-PCR amplification is capable of amplifying a sequence of a microRNA, or derivated sequences thereof, of the present invention.

The term "primer", as used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. A primer serves as an initiation point for nucleotide polymerization catalyzed by DNA polymerase, RNA polymerase or reverse transcriptase.

The primer may be either single-stranded or double-stranded and must be sufficiently long to prime the synthesis of the target microRNA in the presence of the inducing agent. The exact length of the primer will depend upon many factors, including temperature, sequence and/or homology of primer and the method used. For example, in diagnostic applications, the oligonucleotide primer typically contains at least 12 or more nucleotides, depending upon the complexity of the target sequence, although it may contain fewer nucleotides.

The primers herein are selected to be "substantially" complementary to the target microRNA, or derivated pre-microRNA thereof, or its cDNA sequence. This means that the primers must be sufficiently complementary to hybridize with their respective strands. Therefore, the primer sequence need not reflect the exact sequence of the template. For example, a non-complementary nucleotide fragment (i.e., containing a restriction site) may be attached to the 5' end of the primer, with the remainder of the primer sequence being complementary to the strand. Alternatively, non-complementary bases or longer sequences can be interspersed into the primer, provided that the primer sequence has sufficient complementary with the sequence to hybridize therewith and form the template for synthesis of the extension product.

This detection may be accomplished by isolating RNA from a sample. the method may be carried out by converting the isolated RNA to cDNA according to standard methods using reverse transcriptase (RT-PCR).

Following amplification, the presence or absence of the amplification product may be detected. The amplified product may be sequenced by any method known in the art. The sequenced amplified product is then compared to the reference. Alternatively, the nucleic acids may be fragmented into varying sizes of discrete fragments. For example, DNA fragments may be separated according to molecular weight by methods such as and not limited to electrophoresis through an agarose gel matrix. The gels are then analyzed by Southern hybridization.

In another embodiment, the invention relates to the methods according to the present invention, wherein the determining of the presence or the absence of the target microRNA is carried out by a probe capable of specifically hybridizing with the target microRNA.

The term "probe" denotes a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified.

One preferred method for the detection or quantification of the target microRNA, or derived pre-microRNA thereof, involves contacting the isolated target microRNA, or derivated pre-microRNA thereof, with a nucleic acid probe that can hybridize to the target microRNA. Hybridization of the target microRNA with the probe indicates that the target microRNA is being expressed. In an embodiment, the probe includes a label group attached thereto, e.g., a radioisotope, a fluorescent compound, an enzyme, or an enzyme co-factor, or another molecule, such as a spacer molecule, in order to ameliorate the binding of this probe to a solid support.

In one format, the target microRNA, or derived pre-microRNA thereof, is immobilized on a solid surface and contacted with a probe, for example by running the isolated the target microRNA on an agarose gel and transferring the target microRNA from the gel to a membrane, such as nitrocellulose. In an alternative format, the probe(s) are immobilized on a solid surface and the target microRNA is contacted with the probe (s), for example, in an Affymetrix gene chip array, an SPR (Surface Plasmon Resonance) transparent solid support. A skilled artisan can readily adapt known RNA detection methods for use in detecting or quantifying the target microRNA in the method of the present invention.

In a particular embodiment, in the method according to the present invention, the step of the detection or of the quantitative measurement of the target microRNA, or derived pre-microRNA thereof, is carried out by quantitative PCR, preferably by real time RT-PCR.

Using a combination of appropriate oligonucleotide primers, the skilled artisan may determine the level of expression of a target gene in vitro by standard polymerase chain reaction (PCR) procedures, for example, by quantitative PCR. Conventional PCR based assays are discussed, for example, in Innes et al. (1995) "PCR Protocols; A guide to methods and Applications", Academic Press and Innes et al. (1995) "PCR Strategies" Academic Press, San Diego, Calif.

Real-time RT-PCR is a method that utilizes specifically engineered DNA sequences (two primers and a fluorescently labeled probe) to detect and quantify target sequences of DNA. The probe contains a fluorescent reporter dye on one end and a quencher dye on the other. During each amplification cycle, the probe first attaches to the target sequence of DNA, followed by attachment of the primers. As the DNA strand is copied, the reporter dye is released from the probe and emits a fluorescent signal. The amount of fluorescence increases with each cycle of PCR in proportion to the amount of target DNA. This results in direct detection and quantification of the target DNA sequence with a high degree of specificity, accuracy, and sensitivity.

In another embodiment, the present invention comprises the use of the solid support of the present invention for the detection or the quantification of target microRNA.

In another aspect, the present invention comprises a composition or a kit containing as at least one nucleic acid molecule of the present invention, for diagnostic applications.

These markers will be able to be used as molecules for diagnostic or prognostic application, they can also be used as therapeutic targets for new drugs or to lead to the design of new therapeutic tools based on the functional characteristics of synthetic microRNA.

D. Therapeutic Applications

So, in another aspect, the present invention comprises nucleic acid of the present invention as RNA drug, such as microRNA of the present invention or their antisense molecules.

RNA drugs have several advantages including less immunogenicity and toxicity. Their mechanism of action based on complementarities of bases, highly specific, and allow for the reduction of undesirable side effects. The strategies of development are considerably simpler. It is indeed much easier to conceive an antisens RNA than to find a molecule active in a very selective way on a protein, which lets hope for an acceleration of the marketing of new drugs.

We already know that the profiles of expression of the microRNA vary according to tissues. But recently, a team carried out a fine and precise classification of various human cancers, of which some very little differentiated, and of their stages of evolution by studying the profile of expression of the microRNA in these tissues (Lu J and al., 2005).

The antisense molecule of the present invention may comprise any nucleotide sequence portion complementary to the microRNA molecule of the invention, or nucleic acid derived thereof. The antisense molecule will naturally be a single stranded RNA- or DNA molecule of a certain nucleotide length, comprising particularly 15 to 50 nucleotides, preferably 18 to 40 nucleotides, more preferably 18 to 30 nucleotides, still more preferred 18 to 25 nucleotides.

In another aspect, the present invention a pharmaceutical composition containing as an active agent at least one nucleic acid molecule of the present invention, and optionally a pharmaceutically acceptable carrier, preferably for therapeutic applications.

In a preferred embodiment, the pharmaceutical composition of the present invention contains an antisense molecule of the present invention for specific modulating, preferably the enhancing, the expression of the target gene, preferably involved in human diseases.

"Enhancing the expression of target gene" is defined as the ability to prevent the inhibition by the microRNA of the synthesis of the protein encoded by the target gene by blocking the binding site of said microRNA to the untranslated region (UTR) of its target mRN, this binding of said microRNA inhibiting the translation of the target protein.

In this case modulation of translation of the protein encoded by the target may be achieved by inhibiting the complex formation between the target microRNA and its target mRNA, and thus the inhibition of the controlling cellular translation of the target gene by this microRNA.

In an also preferred embodiment, the pharmaceutical composition of the present invention contains a microRNA molecule of the present invention, or a derived pre-microRNA thereof, for specific modulation, preferably the inhibition, of the expression of a specific target gene, preferably involved in human diseases.

"Inhibition of the expression of a target gene" is defined as the ability to increase the inhibition by the microRNA of the synthesis of a specific protein encoded by the target gene by increasing the presence of microRNA and thus binding sites capable of binding the UTR of a target mRNA, increasing consequently the inhibition of the translation of the target protein.

In this case modulation of translation of the protein encoded by the target gene may be achieved by increasing the level of complex formation between the microRNA and its target mRNA, and thus increasing the controlling cellular translation of the target gene by this microRNA.

So, the present invention comprises a method for the treatment of disease in a subject due to an abnormal modulation of the expression of a target gene by a microRNA of the present invention, said method comprising administering said microRNA, or a derived pre-microRNA thereof or an antisense molecule of the present invention whose sequence is complementary to said microRNA.

To improve the stability against endogenous degradation antisense molecules may be protected by pharmaceutically acceptable protection groups commonly known by the person in the art.

The nucleic acid of the invention used for modulating the expression a target gene involved in human disease may be formulated for administration by various different routes, such as topical and systemic, e.g. oral, parenteral, inhalable, and the like, by slow release, by sustained release and by a pump, and the like, and are administered in amounts which prevent or reduce the biological effects brought about by the presence of microRNA into a cell.

The nucleic acids of the invention may be administered by themselves or in conjunction with other drugs and therapies, and in a preventative/prophylactive as well as a therapeutic course and may optionally co-formulated with carriers and other formulation ingredients as known in the art.

In general, the administration of the present nucleic acids may be conducted with formulations suitable for such kind of agents. Examples are injection solutions, wherein the active agents may be protected by e.g. including them in micelles. Aqueous and alcoholic solutions and suspensions, oily solutions and suspensions and oil in-water and water-in-oil emulsions, be a hydrophobic carrier, such as lipid vesicles or particles, such as liposomes.

In a further embodiment, the present invention also concerns a method for the screening of new agents acting on the activity of the microRNA, or derived nucleic acid thereof, of the present invention, new agents which may be suitable for the treatment of a patient whose disease is associated with a gene expression modulation provoked by the presence of said microRNA.

In a preferred embodiment, the invention relates to a method for the screening of an agent for their ability to alter the activity of the microRNA, or derived nucleic acid thereof, of the present invention.

The method comprises the following steps of:
a) providing a cell line, or an organ cell, expressing the microRNA of the present invention and the gene which is modulated by said microRNA, and wherein the gene modulation is associated with a disease;
b) obtaining a candidate agent; and
c) testing the ability of the candidate agent to modify the protein expression of the gene.

Such agents can find use for patients who are not responsive to existing drugs. Screening may be effected using preferably in vitro.

In vitro methods can be carried out in numerous ways such as on transformed cells which express the considered gene and or associated microRNA of the present invention.

Screening assays of the present invention generally involve determining the ability of a candidate agent to affect the activity of microRNA of the present invention on its target mRNA, such as the screening of agents to identify those that inhibit or otherwise modify the function of microRNA of the present invention on the protein expression encoded by the target mRNA.

One method of drug screening utilizes eukaryotic host cells which are stably transformed with recombinant polynucleotides. Such cells, either in viable or fixed form, can be used for standard binding assays. One can measure, for example, the formation of protein expression products or examine the degree to which the formation of such microRNA/target mRNA complexes is interfered by the tested agent.

E. Expression Systems

In another embodiment, the present invention pertains to a cloning or expression vector comprising a nucleic acid molecule of the invention.

The vectors according to the invention preferably contain elements which allow the expression of the nucleotide sequences in a determined host cell. The vector must therefore contain a promoter, signals of initiation and termination of translation, as well as appropriate regions of regulation of transcription. It must be able to be maintained in a stable manner in the host cell. These different elements are chosen and optimized by the person skilled in the art as a function of the host cell used. To this effect, the nucleotide sequences according to the invention can be inserted into autonomous replication vectors in the chosen host, or be integrative vectors of the chosen host.

Such vectors are prepared by methods currently used by the person skilled in the art, and the resulting clones can be introduced into an appropriate host by standard methods, such as lipofection, electroporation, thermal shock, or chemical methods.

The vectors according to the invention are, for example, vectors of plasmidic or viral origin. They are useful for transforming host cells in order to clone or to express the nucleotide sequences according to the invention.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. However, the invention is intended to include such other forms of vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence. The term "regulatory sequence" is intended to include promoters, enhancers and other expression control elements (e.g., polyadenylation signals). Such regulatory sequences are described, for example, in Goeddel; Gene Expression Technology Methods in Enzymology 185, Academic Press, San Diego, Calif. (1990), the disclosure of which is incorporated herein by reference in its entirety. Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed.

In yet another embodiment, a nucleic acid of the invention is expressed in mammalian cells using a mammalian expression vector. When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see Sambrook and Russell, 2001, supra, the disclosure of which is incorporated herein by reference in its entirety.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art.

The invention further provides a recombinant expression vector comprising a DNA molecule of the invention cloned into the expression vector in an antisense orientation compared to a the target microRNA. That is, the DNA molecule is operatively linked to a regulatory sequence in a manner which allows for expression (by transcription of the DNA molecule) of an RNA molecule which is antisense to a target microRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant cloning or expression vector of the invention has been introduced. The terms "host cell" and "recombinant host cell" are used interchangeably herein.

A host cell can be any prokaryotic or eukaryotic cell. For example, a Kalpa can be expressed in bacterial cells such as *E. coli*, insect cells, yeast plant cells or mammalian cells (such as Chinese hamster ovary cells (CHO) or COS cells or human cells). Other suitable host cells are known to those skilled in the art, including *Xenopus laevis* oocytes.

Vector DNA or RNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA or RNA) into a host cell, including calcium phosphate or calcium chloride co-precipitation, DEAE-dextran-mediated transfection, lipofection, or electroporation. Suitable methods for transforming or transfecting host cells can be found in Sambrook and Russell, 2001, supra, the disclosure of which is incorporated herein by reference in its entirety), and other laboratory manuals.

A host cell of the invention, such as a prokaryotic or eukaryotic host cell in culture, can be used to produce (i.e., express) a nucleic acid of the present invention. Accordingly, the invention further provides methods for producing a using the host cells of the invention. In one embodiment, the method comprises culturing the host cell of invention (into which a recombinant expression vector encoding a nucleic acid of the present invention has been introduced) in a suitable medium such that a nucleic acid of the present invention is produced. In another embodiment, the method further comprises isolating a nucleic acid of the present invention from the medium or the host cell.

The host cells of the invention can also be used to produce nonhuman transgenic animals. For example, in one embodiment, a host cell of the invention is a fertilized oocyte or an embryonic stem cell into which a nucleic acid of the present invention have been introduced. Such host cells can then be used to create non-human transgenic animals in which exogenous nucleic acid of the present invention have been introduced into their genome. Such animals are useful for studying the function and/or activity of a nucleic acid of the present invention or fragment thereof and for identifying and/or evaluating modulators of the target mRNA of a nucleic acid of the present invention. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc.

The invention likewise concerns animals, except man, which comprise at least one cell transformed according to the invention.

EXAMPLES

The following examples are offered to illustrate, but not to limit the claimed invention.

Example 1

Identified Pre-microRNA Sequences Using the Validation Protocol in Example 3, Below See sequences SEQ ID Nos. 1 to 1694 and 4035-5758 from the sequence listing, particularly the sequence of the pre-microRNA nucleic acid having the DNA sequence SEQ ID NOs. 3, 5, 16, 22, 32, 34, 35, 36, 60, 70, 77, 81, 82, 90, 93, 139, 141, 151, 152, 158, 163, 170, 175, 176, 183, 184, 191, 192, 200, 205, 219, 223, 224, 248, 275, 276, 323, 328, 344, 357, 363, 366, 385, 400, 406, 407, 425, 472, 481, 489, 500, 501, 503, 512, 527, 530, 531, 563, 608, 633, 640, 651, 653, 664, 678, 728, 744, 753, 784, 785, 786, 826, 832, 858, 876, 903, 909, 911, 926, 927, 940, 942, 944, 946, 947, 951, 955, 963, 967, 975, 1055, 1060, 1083, 1118, 1129, 1137, 1145, 1160, 1161, 1166, 1173, 1174, 1175, 1198, 1205, 1207, 1217, 1233, 1238, 1251, 1267, 1299, 1321, 1323, 1343, 1352, 1396, 1403, 1429, 1485, 1531, 1545, 1547, 1559, 1586, 1592, 1601, 1610, 1611, 1617, 1634, 1645, 1649, 1653, 1656, 1661, 1667, 1681, 1686, 1688, 1693 and 4773.

Example 2

Identified MicroRNA Sequences (Mature MicroRNA) Using the Validation Protocol in Example 3, Below See sequences SEQ ID Nos. 1695 to 4004 and 5759-7803 from the sequence listing, particularly the microRNA having the DNA sequences SEQ ID NOs. 1697, 1698, 1700, 1719, 1720, 1730, 1731, 1732, 1744-1750, 1784, 1785, 1805-1807, 1815-1818, 1824-1828, 1837-1839, 1842, 1843, 1896-1900, 1911-1917, 1925, 1926, 1933, 1934, 1944, 1945, 1949-1954, 1959-1964, 1975-1979, 1990-1993, 2000-2002, 2025-2027, 2068, 2108, 2111, 2112, 2173-2175, 2180, 2181, 2201-2203, 2219-2221, 2228, 2229, 2231-2237, 2260, 2278-2280, 2313, 2314, 2408-2410, 2427-2434, 2437, 2438, 2532, 2450, 2451, 2469-2471, 2476, 2477, 2613, 2620-2622, 2637, 2648, 2679, 2730, 2754-2756, 2771, 2809, 2810, 2814, 2815, 2862, 2863, 2870-2872, 2900, 2958-2961, 2966-2968, 2971-2974, 2999-3001, 3015, 3017-3019, 3021, 3023-3027, 3029, 3030, 3038, 3039, 3048-3050, 3052-3054, 3061, 3062, 3162, 3189, 3232, 3233, 3249, 3250, 3271-3274, 3300-3304, 3320-3329, 3363, 3372-3375, 3378, 3379, 3391, 3392, 3416, 3417, 3422-3424, 3440-3442, 3461, 3497-3499, 3528, 3555-3557, 3567, 3619-3621, 3627, 3628, 3663, 3786, 3804-3808, 3862, 3863, 3870, 3871, 3896-3898, 3912, 3931, 3943, 3950, 3951, 3956, 3957, 3959, 3960, 3966-3968, 3973-3976, 3986, 3987, 3991-3994, 4001-4004.

Example 3

Demonstration that Identified MicroRNAs are Transcripts Present in Cells

A) Material and Methods
Protocol for the microRNA Expression Profiling ("Validation Protocol")
Sample: Total RNA from Mouse
Total RNA from three different mouse tissues listed below were tested in a first run of microRNA expression profiling based on microRNA identification performed with RNA-gate™.
Mouse Normal Tissue Total RNA
Total RNA utilized for the test experiments was purchased from Biochain Institute Inc., Hayward, Calif., USA. The RNA quality was verified with the Agilent bioanalyser.

TABLE 2

| Tissue | cat # | Size |
|---|---|---|
| Liver | R1334149-50 | 50 µg |
| Skeletal muscle | R1334171-50 | 50 µg |
| Lung | R1334152-50 | 50 µg |
| Brain | R1334035-50 | 50 µg |
| Heart | R1334122-50 | 50 µg |

In general, RNA extraction is performed such that small RNAs are not lost. To this end commercially available kits for total RNA isolation can be utilized, such as offered by Ambion, Invitrogen and other molecular biology tool providers.
MicroRNA Enrichment
MicroRNA enrichment can be achieved by utilising the mirVANA™ miRNA isolation kit, the mirVANA™ PARIS™ kit from Ambion.
miRNA purification was performed using the below described gel purification protocol to mapp mature miRNA of about 20 nt in length. The decision not to use a commercially available kit was to diminish background noise, generated when purifying total RNA with a size inferior to 200 nt.
Protocol
1 Prepare a 15% polyacrylamide denaturing gel.
2 Polymerise for 30 min.
3 Resuspend samples in sample buffer (1:1).
4 Denature RNA samples at 95° C. for 5 min.
5 Incubate on ice until loading.
6 Preheat the gel at 400 V for 20 min in 1×TBE.
7 Clear wells from urea prior to loading.
8 Run the gel until the bromophenol blue dye front (the leading dye) migrates about 4-5 cm down the gel.
9 Cut out gel slice between both dyes (bromphenol Blue and Xylene Cyanol). Corresponds to size 60-10 nt.
10 Mix gel slice with elution buffer in an Eppendorf. The gel slice has to be entirely covered.
11 Vortex to mix.
12 Incubate at 37° C. overnight.
13 Centrifuge at Vmax for 2 min.
14 Decant Supernatant 1 into a sterile tube.
15 2nd Elution: Add same amount of elution buffer as in step ten.
16 Incubate 4 min at 95° C.
17 Centrifuge at Vmax for 2 min.
18 Decant Supernatant 2 into a sterile tube.
19 Pool both supernatants.
20 Add 05 µl glycogen at 25 mg/µl.
21 Precipitate with 3 Volumes ethanol at 99% (min. 2 hours).
22 Centrifuge for 15 min at Vmax and 4° C.
23 Wash with 70% ethanol.
24 Vacuum dry for 5 min in speed-vac.
25 Disolve pellet in 3 µl sterile Rnase-free water.

| Buffers | |
|---|---|
| 10 × TBE buffer, pH 8.0 at 25° C. | |
| Tris | 890 mM |
| Boric acid | 890 mM |
| EDTA | 20 mM |
| Denaturing Polyacrylamide Gel | |
| Polyacrylamide | 15% |
| Urea | 7M |
| Ammonium Persulfat | 0.1% |
| TEMED | 25 µl/100 ml |
| in 1 × TBE | |
| Sample buffer | |
| Formamide | 95% |
| 500 mM EDTA | 20 mM |
| Bromophenol Blue | 0.05% |
| Xylene Cyanol FF | 0.05% |
| Elution buffer | |
| Sodium Acetate | 500 mM |
| EDTA | 1 mM |

Sample Labeling
Samples were labeled Cy3 and/or Cy5 using the mirVana™ miRNA labeling kit from Ambion
Microarray
Probe Design
The oligonucleotides were designed according to SEQ ID NOs: 77, 139, 223, 328, 728, 832, 858, 951, 963, 1083, 1173, 1205, 1429, 1611, 1617, 1649, 1688 and to *A. thaliana* microRNA sequence named ath-MIR156a, ath-MIR157 as negative control (the precursor sequence of both are not present in the human genome).
Probe was designed using the protocol below:
1) extracting both the 5' stem and the 3' stem of the precursor microRNA
As used herein, the oligonucleotide coming from the 5' end stem is called SEQ ID-L1, and oligonucleotide coming from the 3' end is called SEQ ID —R1;

2) check the longest sequence for both which is fully conserved with mouse genome for the oligonucleotide R1 and L1;
3) if sequence (R or L) length <=18 nt; remove it
if length<35; catch sequence
if 45>length>=35; design 2 sequences (named -1/-2) with a minimum coverage of 24 nucleotides catch sequences else,
make sequences with a walk of 10 nucleotides to cover all the sequence,
catch sequences;
4) reverse complement sequence;
5) add a spacer (15 nt) on 5' of the sequence.

Reverse complement sequences from design without spacer are SEQ ID 1815, 1896, 2026, 2180, 2181, 2730, 2870, 2871, 2872, 2900, 3029, 3050, 3189, 3322, 3374, 3663, 3912, 3951, 3993, 4004.

Following is an example of oligonucleotide design for SEQ ID 77.

Example: Oligonucleotide Design for SEQ ID 77:

```
                                            (SEQ ID NO: 7805)
5'    CAG      GA   A  GAGAA-    UU     C  A
   AUGG   AGAUAUU  CAU GU     AACA  GCCUU   A
   UACC   UCUGUAA  GUG CA     UUGU  CGGGA   C
3'    AGA      A-   A  AAACAG    UU     UAA
```

Sequence L1=5' stem
>77-L1

```
                                        (SEQ ID NO: 7822)
ATGGCAGAGATATTGACATAGTGAGAAAACATT
``` conservation of sequence L1 with mouse:

```
                                                (SEQ ID NO: 7823)
human ATGGCAGAGATATTGACATAGTGAGAAAACATTGCCTT
                                                (SEQ ID NO: 7824)
mouse ATGGCAGAGATATTGACATAGTGAGAAAACATTGCTTT
      ************************************** **
``` sequence to use to design oligonucleotide:

```
                                        (SEQ ID NO: 7825)
ATGGCAGAGATATTGACATAGTGAGAAAACATTGC
```

Length of this sequence is 35 nt, so 2 oligonucleotides for this 77-L1 with a minimum of coverage of 24 nucleotides:

```
                                        (SEQ ID NO: 1817)
L1-2     cagagatattgacatagtgagaaaacattgc
                                        (SEQ ID NO: 1818)
L1-1  atggcagagatattgacatagtgagaaaa
``` reverse complement of the 2 oligos to obtain oligonucleotides:

```
                                           (SEQ ID NO: 7826)
77-L1-1:   TTTTCTCACTATGTCAATATCTCTGCCAT
                                           (SEQ ID NO: 7827)
77-L2-2:   GCAATGTTTTCTCACTATGTCAATATCTCTG
```

Sequence R1=3' stem
>77-R1

```
                                           (SEQ ID NO: 7828)
AGGGCTTTGTTGACAAAACAGTGAAATGTCTAGACCAT
``` conservation of sequence R1 with mouse:

```
                                                (SEQ ID NO: 7828)
human AGGGCTTTGTTGACAAAACAGTGAAATGTCTAGACCAT
                                                (SEQ ID NO: 7828)
mouse AGGGCTTTGTTGACAAAACAGTGAAATGTCTAGACCAT
      **************************************
``` sequence to use to design oligo:

```
                                           (SEQ ID NO: 7828)
AGGGCTTTGTTGACAAAACAGTGAAATGTCTAGACCAT
``` length of this sequence is 35 nt, so 2 oligos for this 77-L1 with a minimum of coverage of 24 nucleotides:

```
                                         (SEQ ID NO: 1815)
R1-2     tttgttgacaaaacagtgaaatgtctagaccat
                                         (SEQ ID NO: 1816)
R1-1  agggctttgttgacaaaacagtgaaatgtc
``` reverse complement of the 2 oligos to obtain oligonucleotides:

```
                                              (SEQ ID NO: 7829)
77-R1-1:   AGACATTTCACTGTTTTGTCAACAAAGCCCT
                                              (SEQ ID NO: 7830)
77-R1-2:   ATGGTCTAGACATTTCACTGTTTTGTCAACAAA
``` add spacer to all designed oligonucleotides (TTG-TAATACGACTCA; SEQ ID NO:7831) on 5':

```
77-L1-1:                                      (SEQ ID NO: 7832)
TTGTAATACGACTCATTTTCTCACTATGTCAATATCTCTGCCAT

77-L1-2:                                      (SEQ ID NO: 7833)
TTGTAATACGACTCAGCAATGTTTTCTCACTATGTCAATATCTCTG

77-R1-1:                                      (SEQ ID NO: 7834)
TTGTAATACGACTCAAGACATTTCACTGTTTTGTCAACAAAGCCCT

77-R1-2:                                      (SEQ ID NO: 7835)
TTGTAATACGACTCAATGGTCTAGACATTTCACTGTTTTGTCAACAAA
```

See Table 3 for the sequence of OLIGO design.

TABLE 3

OLIGO design

| OLIGO NAME | SEQ ID NO: | SEQUENCE (SEQ ID Nos. 4005 to 4034) |
|---|---|---|
| 77-R1-2(10303-R1-2)* | 4005 | TTGTAATACGACTCAATG-GTCT AGACATTTCACTGTTTTGT-CAA CAAA |
| 139-R1-1(10553-R1-1) | 4006 | TTGTAATACGACTCAGCTG-GCT CCATGCTCCAGTGGG |

TABLE 3-continued

OLIGO design

| OLIGO NAME | SEQ ID NO: | SEQUENCE (SEQ ID Nos. 4005 to 4034) |
|---|---|---|
| 223-R1-2(3926-R1-2) | 4007 | TTGTAATACGACTCAATGGGAG GTTTTGCTATCAA GAAATCTAA TGAGG |
| 328-R1-1(4303-R1-1) | 4008 | TTGTAATACGACTCAAGTGCCC GCTCCTCCGACCTCCCT GCGCA CC |
| 328-R1-2(4303-R1-2) | 4009 | TTGTAATACGACTCAGGGTGGG CAGTGCCCGCTCCTCCGACCTC CCTG |
| 728-R1-1(5795-R1-1) | 4010 | TTGTAATACGACTCACTGCCCT CCAAGAAATAAATTACCCGCAA TTACT |
| 832-L1-1(6216-L1-1) | 4011 | TTGTAATACGACTCAGACATTC AGAGCACTGGGCAGAAATCACA TG |
| 832-L1-2(6216-L1-2) | 4012 | TTGTAATACGACTCATTCACTT TGACATTCAGAGCACTGGGCAG AAAT |
| 832-R1-1(6216-R1-1) | 4013 | TTGTAATACGACTCATAGTTAC TCCCGCCGTTTACCCGTG |
| 858-L1-1(6328-L1-1) | 4014 | TTGTAATACGACTCACACAGAC CTGGAACCTTCAAAAGCAGTA |
| 951-L1-1(6692-L1-1) | 4015 | TTGTAATACGACTCATTTAAGT ACCAAATTTGTCACTC |
| 963-R1-1(6752-R1-1) | 4016 | TTGTAATACGACTCACCCTCCT TTCCCCACCTCAGT |
| 1083-L1-1(7221-L1-1) | 4017 | TTGTAATACGACTCAACCTGCC AGGAAGGTGGGGCGTGGCAGA GGGG |
| 1173-L1-1(7571-L1-1) | 4018 | TTGTAATACGACTCAAGGGCTC CCCCACCCCTAAG |
| 1205-R1-1(7747-R1-1) | 4019 | TTGTAATACGACTCAAATTGCA AATATGCATTTAAATTTAATAA TAC |
| 1429-L1-1(8736-L1-1) | 4020 | TTGTAATACGACTCAACTGGCT CACCTCTAATCACAACCTGCCT GCATT |
| 1611-L1-1(9627-L1-1) | 4021 | TTGTAATACGACTCATTCACTT TCCCTGTGTTAGCTAATGATGC |
| 1617-L1-1(9644-L1-1) | 4022 | TTGTAATACGACTCAGTCAAAA CCCTTCAGGTCCACT |
| 1649-R1-1(9753-R1-1) | 4023 | TTGTAATACGACTCACTCGATT AAACAACAGATACCACTTACAG AC |
| 1688-R1-1(9955-R1-1) | 4024 | TTGTAATACGACTCAGAGCTGC AGACCCCATGCCAATCCATAGC |
| ath-MIR156a-L-1 | 4025 | TTGTAATACGACTCATTGCCTT TGTGTGCTCACTCTCTTCTGTC AG |
| ath-MIR156a-L-2 | 4026 | TTGTAATACGACTCATGCAAAT TGCCTTTGTGTGCTCACTCTCT TC |
| ath-MIR156a-R-1 | 4027 | TTGTAATACGACTCAGAGCAGT GAGCACGCAAGAGAAGCAAGTG CA |
| ath-MIR156a-R-2 | 4028 | TTGTAATACGACTCACTGACAG AAAGAGCAGTGAGCACGCAAGA GAAGCA |
| ath-MIR157a-L-1 | 4029 | TTGTAATACGACTCATCTCATC ATCTGTGCTCTCTATCTTCTGT CAACAC |
| ath-MIR157a-L-2 | 4030 | TTGTAATACGACTCACCGAATT GTATCTCATCATCTGTGCTCTC TATCTT |
| ath-MIR157a-L-3 | 4031 | TTGTAATACGACTCACTCCGAA TTGTATCTCATCATCTGTGC |
| ath-MIR157a-R-1 | 4032 | TTGTAATACGACTCAAGGCTAG AGAGCACAAAGGAGTAAGATGC AAAGAA |
| ath-MIR157a-R-2 | 4033 | TTGTAATACGACTCATGATGAC AGAAGGCTAGAGAGCACAAAGG AGTAAG |

TABLE 3-continued

OLIGO design

| OLIGO NAME | SEQ ID NO: | SEQUENCE (SEQ ID Nos. 4005 to 4034) |
|---|---|---|
| MUSTRP2 | 4034 | TTGTAATACGACTCATCG-CACC CAAAGCGAGAATCATAC-CCCTA GACCAACGAGC |

*In the wording "77-R1-2 (10303-R1-2)" for OLIGO NAME, the term in brackets 10303-R1-2 corresponds to the reference used for the name the oligonucleotide probe in Table 4.
The number "77" in the term 77-R1-2 corresponds to the number of the corresponding pre-miRNA SEQ ID NO:.

Each specific mapping sequence is preceded by a spacer sequence of 15 nt. This spacer sequence serves to prevent non-specific interactions of the oligonucleotides with the array support. The oligonucleotides are amino-modified at their 5' end to allow their fixing onto the array support.

Oligonucleotide Synthesis

The probes to be spotted onto the array were synthesized according to standard protocols from Operon Biotechnologies, Cologne, Germany, specialised in the synthesis of modified oligonucleotide.

Array Support

As support for the microarray the Nexterion microarray glass slides from Schott were utilised.

Spotting

Probe concentration is 50 μmol for each probe. The probes were spotted using the Nexterion spotting buffer+1% SDS (Sodium dodecyl sulfate) provided by Schott with the array glass support. 1% SDS was added to allow larger spots (e.g. 100-150 micron compared to 70-100 micron without SDS).

The spotter utilized was the Q array mini from Gentix. After the deposit of 1 series of spots the spotting needle was washed 5× before spotting the next series of probes. Spotted glass slides were kept at 4° C. until use.

Hybridization

Protocol

1 Prehybridize the slide with Prehybridization buffer for 30 min at 42° C.
2 Dip the slide into sterile water.
3 Dip the slide into isopropanol.
4 Dry the slide.
5 Heat the hybridization buffer up to 65° C. for 5 min immediately before use.
6 Add 3×miRNA hybridization buffer to the labeled miRNA sample (final concentration: 1×).
7 Heat the miRNA hybridization mixture to 95° C. for 3 min, then briefly centrifuge.
8 Transfer the miRNA hybridization mixture to a microarray. Be careful to avoid bubbles when placing the cover slip.
9 Place the array into a hybridization cassette (coming chamber). Add diluted salt to maintain humidity in the chamber.
10 Incubate 42° C. for 12-16 hr.
11 Remove the array from the cassette and submerge it in low stringency wash solution at room temperature for 1 min under agitation. The cover slip will disengage from the slide.
12 Transfer the array to a second low stringency wash solution for 1 min. under agitation.
13 Transfer the array to a high stringency wash solution for 1 min under agitation.
14 Dip the slide into water.
15 Dip the slide into isopropanol.
16 Dry the slide.

Buffers
Prehybridization Buffer
  3×SSC
  0.1% SDS
  10 mg/ml Salmon sperm DNA
3×miRNA Hybridization Buffer
  Solution delivered with mirVana Probe set kit Ambion
Washing Solution
  Solutions delivered with mirVana Probe set kit Ambion
  Low stringency wash solution: 940 ml water
  10 ml detergent concentrate from Ambion
  50 ml Salt concentrate from Ambion
  High stringency wash solution: 995 ml water
Image Acquisition
  Name of the Scanner: Fluoroskan Ascent (Labsystem)
  The digital images are acquired from the Axon scanner using the software Genepix. The image is formatted in tif format, defined by an image color depth of 16 bits/pixel (1600*1600). Pixels can have intensities values ranging from 0 to 65,535. Pixels exhibiting the maximum intensity value are "saturated" assigned the value 65,535.
  Resolution: Scan array at 10 μm/px
  Settings: For hybridization experiments using different fluorescent dyes (e.g Cy5 and Cy3) the photomultiplier tube (PMT) is adjusted to the higher intensity spot. Cy3 is scanned at lower PMT settings.
Image Analysis
  A photo-multiplier of a laser scanner digitizes a captured fluorescence for a given "point" of a slide (or screen) and stores a numerical value in a pixel corresponding to that point. A picture composed of such pixels is analyzed during image analysis.
  First task for image analysis is to detect the spot position and limits. This stage is often called segmentation. Usually spots are segmented by circles of adaptable or fixed radius. To be reliably segmented and quantified, the spot diameter should be more than 5-6 pixels. Before segmentation an indexing grid is provided giving approximate positions of spots. The segmentation itself detects the limits of spots near the grid nodes. The segmentation must be conducted in rather flexible way because of spotting imperfection or support deformation. Put in other way, the spots lye almost never on perfect rectangular grid.
  The second task of image analysis is to quantify spots and export data in a result file. This is relatively easy and well defined task once the spots were determined on the image. Statistics most frequently used to quantify spot intensity are the mean or median of pixels belonging to a spot. Median is more robust than mean value in presence of outlier pixels. In practice, however, there are little differences in results obtained using mean or median.
miRNA Array Prehybridization
  Incubated the miRNA array in a solution: 3×SSC, SDS 0.1%, 1% (V/V) salmon sperm at 10 mg/ml for 30 min at 42° C., then wash the slide by dipping them in water, then isopropanol and dry the slide before the hybridization.
miRNA Array Hybridization
  Heat the 3×miRNA hybridization buffer to 65° C. for 5 min immediately before use to dissolve it completely.
  Add 3×miRNA hybridization buffer to the labeled miRNA sample for a final 1× concentration of miRNA hybridization buffer.
  Heat the miRNA hybridization mixture to 95° C. for 3 min, then briefly centrifuge.
  Transfer the miRNA hybridization mixture to a microarray. Be careful to the bubble Place the array into a hybridization cassette (coming chamber). Add diluted salt to maintain humidity in the chamber.
Incubate 42° C. for 12-16 hrs.

Washing

Remove the hybridized miRNA array from the cassette and submerge it in Low stringency wash at room temperature for 1 min under agitation. The cover slip will disengage from the slide.

Transfer the hybridized miRNA array to a second low stringency wash clean slide holder for 1 min under agitation.

Then transfer the hybridized miRNA array to a high stringency wash clean slide holder for 1 min. under agitation.

Dip the slide into water, than isopropanol and dry the slide.

Low stringency wash solution: 940 ml water
  10 ml detergent concentrate from Ambion
  50 ml Salt concentrate from Ambion High stringency wash solution: 995 ml water
  5 ml Salt concentrate from Ambion Results Tables 4, 5 and 6 demonstrate the presence of the microRNA transcripts identified by the present methods in cells of different tissues.

TABLE 4

| TESTED TISSUES | Well | OLIGO NAME | Position Row/column | | Intensity | SEQ ID precursor | SEQ ID mature |
|---|---|---|---|---|---|---|---|
| LUNG | 2B13 | MUSTRP2 | 19 | 5 | 0.61 | Positive control | |
| | 2B13 | MUSTRP2 | 20 | 5 | 0.55 | Positive control | |
| | 2A20 | ath-MIR156a-L-1 | 9 | 41 | −0.92 | Negative control | |
| | 2A21 | ath-MIR156a-L-2 | 11 | 5 | −0.88 | Negative control | |
| | 2B2 | ath-MIR157a-L-3 | 14 | 17 | −0.72 | Negative control | |
| | 2B4 | ath-MIR157a-R-2 | 14 | 41 | −0.67 | Negative control | |
| | 2D22 | 10553-R1-1 | 47 | 17 | −0.39 | 139 | 1896 |
| | 2D22 | 10553-R1-1 | 48 | 17 | −0.35 | 139 | 1896 |
| | 2G4 | 4303-R1-1 | 25 | 42 | −0.06 | 328 | 2180 |
| | 2G4 | 4303-R1-1 | 26 | 42 | −0.06 | 328 | 2180 |
| | 2G5 | 4303-R1-2 | 27 | 6 | −0.4 | 328 | 2181 |
| | 2G5 | 4303-R1-2 | 28 | 6 | −0.53 | 328 | 2181 |
| | 2K7 | 5795-R1-1 | 27 | 31 | −0.6 | 728 | 2730 |
| | 2K7 | 5795-R1-1 | 28 | 31 | −0.57 | 728 | 2730 |
| | 2L4 | 6216-L1-1 | 37 | 43 | 1.52 | 832 | 2870 |
| | 2L4 | 6216-L1-1 | 38 | 43 | 1.54 | 832 | 2870 |
| | 2L5 | 6216-L1-2 | 39 | 7 | 1.6 | 832 | 2871 |
| | 2L5 | 6216-L1-2 | 40 | 7 | 1.61 | 832 | 2871 |
| | 2L6 | 6216-R1-1 | 39 | 19 | 1.91 | 832 | 2872 |
| | 2L6 | 6216-R1-1 | 40 | 19 | 1.88 | 832 | 2872 |
| | 2N9 | 6752-R1-1 | 17 | 8 | 0.73 | 963 | 3050 |
| | 2N9 | 6752-R1-1 | 18 | 8 | 0.7 | 963 | 3050 |
| | 2O19 | 7571-L1-1 | 33 | 32 | −0.14 | 1173 | 3322 |
| | 2O19 | 7571-L1-1 | 34 | 32 | −0.15 | 1173 | 3322 |
| | 3C16 | 9627-L1-1 | 31 | 45 | −0.61 | 1611 | 4004 |
| | 3C16 | 9627-L1-1 | 32 | 45 | −0.54 | 1611 | 4004 |
| | 3D7 | 9955-R1-1 | 39 | 33 | −0.76 | 1688 | 3993 |
| | 3D7 | 9955-R1-1 | 40 | 33 | −0.6 | 1688 | 3993 |
| MUSCLE | 2B13 | MUSTRP2 | 19 | 5 | 0.16 | Positive control | |
| | 2B13 | MUSTRP2 | 20 | 5 | 0.21 | Positive control | |
| | 2A21 | ath-MIR156a-L-2 | 12 | 5 | −0.11 | Negative control | |
| | 2B2 | ath-MIR157a-L-3 | 13 | 17 | −0.42 | Negative control | |
| | 2B1 | ath-MIR157a-L-2 | 14 | 5 | −0.43 | Negative control | |
| | 2B3 | ath-MIR157a-R-1 | 13 | 29 | −0.58 | Negative control | |
| | 2A21 | ath-MIR156a-L-2 | 11 | 5 | −0.65 | Negative control | |
| | 2B1 | ath-MIR157a-L-2 | 13 | 5 | −1.01 | Negative control | |
| | 2D22 | 10553-R1-1 | 47 | 17 | 0.08 | 139 | 1896 |
| | 2D22 | 10553-R1-1 | 48 | 17 | 0.03 | 139 | 1896 |
| | 2G4 | 4303-R1-1 | 25 | 42 | 0.48 | 328 | 2180 |
| | 2G4 | 4303-R1-1 | 26 | 42 | 0.47 | 328 | 2180 |
| | 2G5 | 4303-R1-2 | 27 | 6 | 0.02 | 328 | 2181 |
| | 2G5 | 4303-R1-2 | 28 | 6 | −0.03 | 328 | 2181 |
| | 2K7 | 5795-R1-1 | 27 | 31 | −0.05 | 728 | 2730 |
| | 2K7 | 5795-R1-1 | 28 | 31 | −0.01 | 728 | 2730 |
| | 2L4 | 6216-L1-1 | 37 | 43 | 1.99 | 832 | 2872 |
| | 2L4 | 6216-L1-1 | 38 | 43 | 2.04 | 832 | 2872 |
| | 2L5 | 6216-L1-2 | 39 | 7 | 1.98 | 832 | 2872 |
| | 2L5 | 6216-L1-2 | 40 | 7 | 1.98 | 832 | 2872 |
| | 2L6 | 6216-R1-1 | 39 | 19 | 2.26 | 832 | 2872 |
| | 2L6 | 6216-R1-1 | 40 | 19 | 2.25 | 832 | 2872 |
| | 2N9 | 6752-R1-1 | 17 | 8 | 1.03 | 963 | 3050 |
| | 2N9 | 6752-R1-1 | 18 | 8 | 1.01 | 963 | 3050 |
| | 2O19 | 7571-L1-1 | 33 | 32 | 0.02 | 1173 | 3322 |
| | 2O19 | 7571-L1-1 | 34 | 32 | 0.08 | 1173 | 3322 |
| | 3C17 | 9644-L1-1 | 33 | 9 | −0.04 | 1617 | 3912 |
| | 3C17 | 9644-L1-1 | 34 | 9 | −0.04 | 1617 | 3912 |
| LIVER | 2B13 | MUSTRP2 | 19 | 5 | 0.21 | Positive control | |
| | 2B13 | MUSTRP2 | 20 | 5 | 0.21 | Positive control | |
| | 2B2 | ath-MIR157a-L-3 | 13 | 17 | −0.1 | Negative control | |
| | 2B1 | ath-MIR157a-L-2 | 14 | 5 | −0.24 | Negative control | |
| | 2A21 | ath-MIR156a-L-2 | 12 | 5 | −0.33 | Negative control | |
| | 2B3 | ath-MIR157a-R-1 | 14 | 29 | −0.41 | Negative control | |

TABLE 4-continued

| TESTED TISSUES | Well | OLIGO NAME | Position Row/column | | Intensity | SEQ ID precursor | SEQ ID mature |
|---|---|---|---|---|---|---|---|
| | 2A23 | ath-MIR156a-R-2 | 11 | 29 | −0.57 | Negative control | |
| | 2A22 | ath-MIR156a-R-1 | 12 | 17 | −0.63 | Negative control | |
| | 2B1 | ath-MIR157a-L-2 | 13 | 5 | −0.65 | Negative control | |
| | 2D22 | 10553-R1-1 | 47 | 17 | 0.04 | 139 | 1896 |
| | 2D22 | 10553-R1-1 | 48 | 17 | 0.01 | 139 | 1896 |
| | 2G4 | 4303-R1-1 | 25 | 42 | 0.26 | 328 | 2180 |
| | 2G4 | 4303-R1-1 | 26 | 42 | 0.21 | 328 | 2180 |
| | 2L4 | 6216-L1-1 | 37 | 43 | 2.09 | 832 | 2872 |
| | 2L4 | 6216-L1-1 | 38 | 43 | 2.09 | 832 | 2872 |
| | 2L5 | 6216-L1-2 | 39 | 7 | 2.14 | 832 | 2872 |
| | 2L5 | 6216-L1-2 | 40 | 7 | 2.16 | 832 | 2872 |
| | 2L6 | 6216-R1-1 | 39 | 19 | 2.48 | 832 | 2872 |
| | 2L6 | 6216-R1-1 | 40 | 19 | 2.47 | 832 | 2872 |
| | 2N21 | 7221-L1-1 | 23 | 8 | 0.12 | 1083 | 3189 |
| | 2N21 | 7221-L1-1 | 24 | 8 | 0.08 | 1083 | 3189 |
| | 2N9 | 6752-R1-1 | 17 | 8 | 1.15 | 963 | 3050 |
| | 2N9 | 6752-R1-1 | 18 | 8 | 1.13 | 963 | 3050 |
| | 2O19 | 7571-L1-1 | 33 | 32 | 0.04 | 1173 | 3322 |
| | 2O19 | 7571-L1-1 | 34 | 32 | 0.03 | 1173 | 3322 |
| | 3B5 | 8736-L1-1 | 15 | 9 | −0.01 | 1429 | 3663 |
| | 3B5 | 8736-L1-1 | 16 | 9 | 0.04 | 1429 | 3663 |
| HEART_BRAIN Cy5 | 2B13 | MUSTRP2 | 19 | 5 | 0.93 | Positive control | |
| | 2B13 | MUSTRP2 | 20 | 5 | 0.81 | Positive control | |
| | 2B2 | ath-MIR157a-L-3 | 14 | 17 | −0.01 | Negative control | |
| | 2B2 | ath-MIR157a-L-3 | 13 | 17 | −0.18 | Negative control | |
| | 2A21 | ath-MIR156a-L-2 | 11 | 5 | −0.22 | Negative control | |
| | 2B1 | ath-MIR157a-L-2 | 13 | 5 | −0.23 | Negative control | |
| | 2A24 | ath-MIR157a-L-1 | 11 | 41 | −0.26 | Negative control | |
| | 2A21 | ath-MIR156a-L-2 | 12 | 5 | −0.29 | Negative control | |
| | 2B4 | ath-MIR157a-R-2 | 13 | 41 | −0.31 | Negative control | |
| | 2A23 | ath-MIR156a-R-2 | 12 | 29 | −0.31 | Negative control | |
| | 2B3 | ath-MIR157a-R-1 | 13 | 29 | −0.31 | Negative control | |
| | 2A23 | ath-MIR156a-R-2 | 11 | 29 | −0.38 | Negative control | |
| | 2B1 | ath-MIR157a-L-2 | 14 | 5 | −0.38 | Negative control | |
| | 2A20 | ath-MIR156a-L-1 | 9 | 41 | −0.41 | Negative control | |
| | 2A20 | ath-MIR156a-L-1 | 10 | 41 | −0.41 | Negative control | |
| | 2B4 | ath-MIR157a-R-2 | 14 | 41 | −0.43 | Negative control | |
| | 2A22 | ath-MIR156a-R-1 | 11 | 17 | −0.45 | Negative control | |
| | 2G4 | 4303-R1-1 | 25 | 42 | 0.26 | 328 | 2180 |
| | 2G4 | 4303-R1-1 | 26 | 42 | 0.3 | 328 | 2180 |
| | 2G5 | 4303-R1-2 | 27 | 6 | 0.02 | 328 | 2181 |
| | 2G5 | 4303-R1-2 | 28 | 6 | 0.02 | 328 | 2181 |
| | 2L4 | 6216-L1-1 | 37 | 43 | 2.08 | 832 | 2872 |
| | 2L4 | 6216-L1-1 | 38 | 43 | 2.09 | 832 | 2872 |
| | 2L5 | 6216-L1-2 | 39 | 7 | 2.04 | 832 | 2872 |
| | 2L5 | 6216-L1-2 | 40 | 7 | 2.06 | 832 | 2872 |
| | 2L6 | 6216-R1-1 | 39 | 19 | 2.4 | 832 | 2872 |
| | 2L6 | 6216-R1-1 | 40 | 19 | 2.42 | 832 | 2872 |
| | 2L8 | 6328-L1-1 | 39 | 43 | 0.4 | 858 | 2900 |
| | 2L8 | 6328-L1-1 | 40 | 43 | 0.07 | 858 | 2900 |
| | 2N3 | 6692-L1-1 | 13 | 32 | −0 | 951 | 3029 |
| | 2N3 | 6692-L1-1 | 14 | 32 | 0.03 | 951 | 3029 |
| | 2N9 | 6752-R1-1 | 17 | 8 | 1.09 | 963 | 3050 |
| | 2N9 | 6752-R1-1 | 18 | 8 | 1.04 | 963 | 3050 |
| | 2O19 | 7571-L1-1 | 33 | 32 | 0.15 | 1173 | 3322 |
| | 2O19 | 7571-L1-1 | 34 | 32 | 0.09 | 1173 | 3322 |
| HEART_BRAIN Cy3 | 2B13 | MUSTRP2 | 19 | 5 | 0.18 | Positive control | |
| | 2B13 | MUSTRP2 | 20 | 5 | 0.09 | Positive control | |
| | 2B3 | ath-MIR157a-R-1 | 13 | 29 | −0.21 | Negative control | |
| | 2B4 | ath-MIR157a-R-2 | 13 | 41 | −0.25 | Negative control | |
| | 2B1 | ath-MIR157a-L-2 | 14 | 5 | −0.31 | Negative control | |
| | 2A24 | ath-MIR157a-L-1 | 12 | 41 | −0.32 | Negative control | |
| | 2A24 | ath-MIR157a-L-1 | 11 | 41 | −0.33 | Negative control | |
| | 2B2 | ath-MIR157a-L-3 | 14 | 17 | −0.34 | Negative control | |
| | 2B3 | ath-MIR157a-R-1 | 14 | 29 | −0.35 | Negative control | |
| | 2B1 | ath-MIR157a-L-2 | 13 | 5 | −0.39 | Negative control | |
| | 2B2 | ath-MIR157a-L-3 | 13 | 17 | −0.41 | Negative control | |
| | 2A23 | ath-MIR156a-R-2 | 11 | 29 | −0.45 | Negative control | |
| | 2A23 | ath-MIR156a-R-2 | 12 | 29 | −0.46 | Negative control | |
| | 2A21 | ath-MIR156a-L-2 | 12 | 5 | −0.67 | Negative control | |
| | 2D1 | 10303-R1-2 | 37 | 5 | −0.2 | 77 | 1815 |
| | 2D1 | 10303-R1-2 | 38 | 5 | −0.16 | 77 | 1815 |
| | 2F2 | 3926-R1-2 | 13 | 18 | −0.17 | 223 | 2026 |
| | 2F2 | 3926-R1-2 | 14 | 18 | −0.19 | 223 | 2026 |
| | 2G4 | 4303-R1-1 | 25 | 42 | −0.04 | 328 | 2180 |
| | 2G4 | 4303-R1-1 | 26 | 42 | 0.02 | 328 | 2180 |
| | 2L4 | 6216-L1-1 | 37 | 43 | 1.44 | 832 | 2872 |

TABLE 4-continued

| TESTED TISSUES | Well | OLIGO NAME | Position Row/column | | Intensity | SEQ ID precursor | SEQ ID mature |
|---|---|---|---|---|---|---|---|
| | 2L4 | 6216-L1-1 | 38 | 43 | 1.44 | 832 | 2872 |
| | 2L5 | 6216-L1-2 | 39 | 7 | 1.47 | 832 | 2872 |
| | 2L5 | 6216-L1-2 | 40 | 7 | 1.45 | 832 | 2872 |
| | 2L6 | 6216-R1-1 | 39 | 19 | 1.8 | 832 | 2872 |
| | 2L6 | 6216-R1-1 | 40 | 19 | 1.83 | 832 | 2872 |
| | 2N9 | 6752-R1-1 | 17 | 8 | 0.48 | 963 | 3050 |
| | 2N9 | 6752-R1-1 | 18 | 8 | 0.5 | 963 | 3050 |
| | 2O19 | 7571-L1-1 | 33 | 32 | −0.16 | 1173 | 3322 |
| | 2O19 | 7571-L1-1 | 34 | 32 | −0.15 | 1173 | 3322 |
| | 2P2 | 7747-R1-1 | 37 | 20 | −0.1 | 1205 | 3374 |
| | 2P2 | 7747-R1-1 | 38 | 20 | −0.14 | 1205 | 3374 |
| | 3D3 | 9753-R1-1 | 37 | 33 | −0.19 | 1649 | 3951 |
| | 3D3 | 9753-R1-1 | 38 | 33 | −0.12 | 1649 | 3951 |

TABLE 5

Validated pre-microRNA Sequences

| SEQ ID NO: | OLIGO ID. | Tissue of Validation |
|---|---|---|
| 3 | 8587-R2-1 | Commercial prostate cell line androgen independent (Cline 2 and 3) |
| | 8587-R2-2 | Commercial prostate cell line immortalized (Cline 5) |
| | 10010-R2-1 | muscle after insulin injection (CTRav) |
| | 10010-R2-2 | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal (Cline 7) |
| | | T cells control |
| | | T cells treated with synthetic androgen "R1881" |
| | | Total prostate RNA (Cline 1) |
| | | Th1 |
| 5 | 10018-L1-1 | Th1eH |
| | | Th2eH |
| 16 | 10058-R1-1 | Th1eH |
| 22 | 10093-L2-1 | Commercial prostate cell line androgen dependent (Cline 4) |
| | 10093-R2-1 | Commercial prostate cell line androgen independent (Cline 2 and 3) |
| | 10093-R2-2 | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 32 | 10138-L2-1 | Commercial prostate cell line androgen dependent (Cline 4) |
| | 10138-L2-2 | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 34 | 10145-L2-1 | T cells control |
| | | T cells treated with synthetic androgen "R1881" |
| | | Total prostate RNA (Cline 1) |
| 35 | 10149-R1-1 | bone_marrow |
| | | Th1eH |
| | | Th2eH |
| 36 | 10154-R1-1 | fat |
| | | testes |
| 60 | 10233-L2-2 | T cells treated with synthetic androgen "R1881" |

TABLE 5-continued

Validated pre-microRNA Sequences

| SEQ ID NO: | OLIGO ID. | Tissue of Validation |
|---|---|---|
| 70 | 10273-L1-1 | Th1eH |
|  | 10273-R1-2 | Th1lH |
|  |  | Th2eH |
|  |  | Th2lH |
| 77 | 10303-L1-1 | Th2eM |
| 81 | 10324-L1-1 | Th1eH |
|  | 10324-L1-2 | Th2eM |
| 82 | 10325-R2-1 | T cells treated with synthetic androgen "R1881" |
| 90 | 10342-R2-2 | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | Prostate primary cell line cancer (Cline 8) |
|  |  | T cells control |
|  |  | T cells treated with synthetic androgen "R1881" |
|  |  | Total prostate RNA (Cline 1) |
| 93 | 10347-L1-2 | Th1eH |
|  |  | Th2eH |
| 139 | 10553-L1-1 | Th1lH |
|  | 10553-R1-1 | Th2lH |
|  |  | brain |
|  |  | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | GFP.RV |
|  |  | kidney |
|  |  | muscle after insulin injection (CTRav) |
|  |  | muscle before insulin injection (CTRav) |
|  |  | Prostate primary cell line cancer (Cline 8) |
|  |  | Prostate primary cell line normal (Cline 7) |
|  |  | RVp |
|  |  | RV.Tbet |
|  |  | spleen |
|  |  | T cells control |
|  |  | T cells treated with synthetic androgen "R1881" |
|  |  | testes |
|  |  | Thymocytes |
|  |  | thymus |
|  |  | Total prostate RNA (Cline 1) |
| 141 | 10562-L1-1 | Th1lH |
|  | 10562-L1-2 | Th2eM |
|  |  | Th2lH |
|  |  | Th2lH |
| 151 | 10615-L1-1 | Th2lH |
|  | 10615-L1-2 | Th1lH |
|  | 10615-R1-1 | Th2eM |
| 152 | 10617-R1-1 | Th1lH |
|  |  | Th2lH |
| 158 | 4155-L1-1 | Th1eM |
| 163 | 3717-L2-1 | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | muscle after insulin injection (CTRav) |
|  |  | muscle after insulin injection to diabetic subject (DIABav) |
|  |  | muscle before insulin injection (CTRav) |
|  |  | muscle before insulin injection to diabetic subject (DIABav) |
|  |  | Prostate primary cell line cancer (Cline 8) |
|  |  | Prostate primary cell line normal + cancer (Cline 6) |
|  |  | Prostate primary cell line normal (Cline 7) |
|  |  | T cells control |
|  |  | T cells treated with synthetic androgen "R1881" |
|  |  | Th1 |
|  |  | Total prostate RNA (Cline 1) |
| 170 | 3740-R1-1 | Th2lH |
| 175 | 3755-L1-2 | Th1lH |
|  |  | Th2eH |
|  |  | Th2eM |
|  |  | Th2lH |
| 176 | 3758-R2-2 | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | muscle after insulin injection (CTRav) |
|  |  | muscle after insulin injection to diabetic subject (DIABav) |
|  |  | muscle before insulin injection (CTRav) |
|  |  | muscle before insulin injection to diabetic subject (DIABav) |
|  |  | Prostate primary cell line cancer (Cline 8) |
|  |  | Prostate primary cell line normal + cancer (Cline 6) |

TABLE 5-continued

Validated pre-microRNA Sequences

| SEQ ID NO: | OLIGO ID. | Tissue of Validation |
|---|---|---|
| | | Prostate primary cell line normal (Cline 7) |
| | | T cells control |
| | | T cells treated with synthetic androgen "R1881" |
| | | Th1 |
| | | Total prostate RNA (Cline 1) |
| 183 | 3784-R1-2 | Th1eH |
| 184 | 3788-R2-2 | T cells treated with synthetic androgen "R1881" |
| 191 | 3817-R1-1 | Th1lH |
| | | Th2eM |
| | | Th2lH |
| 192 | 3819-L2-2 | T cells treated with synthetic androgen "R1881" |
| 200 | 3849-L1-2 | Th1lH |
| | | Th2lH |
| 205 | 3872-L1-1 | testes |
| 219 | 3920-L1-1 | Th1eH |
| | | Th1lH |
| | | Th2eH |
| | | Th2eM |
| | | Th2lH |
| 223 | | fat |
| | | kidney |
| | | T cells control |
| | | T cells treated with synthetic androgen "R1881" |
| | | testes |
| | | Th1lH |
| 224 | 3931-L1-1 | Th2eH |
| 248 | 3995-L2-1 | T cells control |
| | 3995-L2-2 | T cells treated with synthetic androgen "R1881" |
| | | Total prostate RNA (Cline 1) |
| | | Commercial prostate cell line androgen independent (Cline 2 and 3) |
| | | Total prostate RNA (Cline 1) |
| 275 | 4088-L1-2 | Th1lM |
| | | Th2lM |
| 276 | 9977-R2-1 | T cells control |
| | 4097-R2-1 | T cells treated with synthetic androgen "R1881" |
| 323 | 4284-L1-1 | Th1lH |
| | 4284-L1-2 | Th2lH |
| | | Th2eH |
| 328 | 4303-R1-1 | bone_marrow |
| | 4303-R1-2 | brain |
| | | colon |
| | | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFPp |
| | | GFP.RV |
| | | GFPs |
| | | kidney |
| | | liver |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | rat oestrogene stimulated |
| | | RVp |
| | | RVs |
| | | RV.Tbet |
| | | Sperm (PACH) |
| | | Sperm (SR) |
| | | spleen |
| | | T cells control |
| | | T cells treated with synthetic androgen "R1881" |
| | | testes |
| | | Th1 |
| | | Th1_early_human |
| | | Th1_early_mouse |
| | | Th1eH |
| | | Th1_late_mouse |
| | | Th2_early_human |
| | | Th2_early_mouse |
| | | Th2eH |
| | | Th2_late_mouse |

TABLE 5-continued

Validated pre-microRNA Sequences

| SEQ ID NO: | OLIGO ID. | Tissue of Validation |
|---|---|---|
| | | Thp |
| | | Thymocytes |
| | | thymus |
| | | Thymus |
| | | Total prostate RNA (Cline 1) |
| 344 | 4352-L1-1 | Th1eH |
| | | Th1lH |
| | | Th2eH |
| | | Th2eM |
| | | Th2lH |
| 357 | 4392-L1-2 | bone_marrow |
| 363 | 4417-R1-1 | bone_marrow |
| | | colon |
| | | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFP.RV |
| | | kidney |
| | | liver |
| | | muscle after insulin injection (CTRav) |
| | | muscle before insulin injection (CTRav) |
| | | Prostate primary cell line cancer (Cline 8) |
| | | Prostate primary cell line normal + cancer (Cline 6) |
| | | Prostate primary cell line normal (Cline 7) |
| | | RV.Tbet |
| | | Sperm (SR) |
| | | spleen |
| | | T cells control |
| | | testes |
| | | Th1 |
| | | Th1_early_human |
| | | Th1_early_mouse |
| | | Th1_late_mouse |
| | | Th2_early_human |
| | | Th2_early_mouse |
| | | Th2_late_mouse |
| | | Thp |
| | | thymus |
| | | Thymus |
| | | Total prostate RNA (Cline 1) |
| 366 | 4432-L1-1 | Th1eH |
| | 4432-L1-2 | Th2eH |
| | 4432-R1-1 | |
| 385 | 4482-R1-1 | Th1eH |
| 400 | 4528-R1-1 | Th1lH |
| | | Th2lH |
| 406 | 4567-L1-1 | Commercial prostate cell line androgen independent (Cline 2 and 3) |
| | | Commercial prostate cell line immortalized (Cline 5) |
| | | Prostate primary cell line normal (Cline 7) |
| | | testes |
| | | Th1eH |
| | | Th2eH |
| | | Total prostate RNA (Cline 1) |
| 407 | 5232-L2-1 | Commercial prostate cell line androgen independent (Cline 2 and 3) |
| | | Total prostate RNA (Cline 1) |
| 425 | 4638-L1-1 | Th2eM |
| 472 | 4829-R2-1 | Commercial prostate cell line androgen dependent (Cline 4) |
| | 4829-R2-2 | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| | | T cells treated with synthetic androgen "R1881" |
| 481 | 4875-R2-2 | Total prostate RNA (Cline 1) |
| 489 | 4892-L1-1 | Th1lH |
| | 4892-R1-1 | Th2lH |
| | 4892-R1-2 | |

TABLE 5-continued

Validated pre-microRNA Sequences

| SEQ ID NO: | OLIGO ID. | Tissue of Validation |
|---|---|---|
| 500 | 4939-L1-2 | Th1lH |
|  | 4939-R1-2 | Th2lH |
|  |  | fat |
|  |  | testes |
| 501 | 4946-L1-1 | Th2eH |
|  | 4946-R1-1 | Th1lH |
|  |  | Th2eM |
|  |  | Th2lH |
| 503 | 4958-R2-2 | T cells control |
|  |  | T cells treated with synthetic androgen "R1881" |
| 512 | 4983-L1-1 | Th1lH |
|  |  | Th2eM |
|  |  | Th2lH |
| 527 | 5063-L2-2 | T cells treated with synthetic androgen "R1881" |
| 530 | 5070-L1-1 | Th1lH |
|  |  | Th2eM |
|  |  | Th2lH |
| 531 | 5071-R2-1 | Commercial prostate cell line androgen independent (Cline 2 and 3) |
|  |  | T cells control |
|  |  | T cells treated with synthetic androgen "R1881" |
|  |  | Total prostate RNA (Cline 1) |
| 563 | 5193-R1-1 | testes |
| 608 | 5380-R2-2 | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | Prostate primary cell line cancer (Cline 8) |
|  |  | Prostate primary cell line normal (Cline 7) |
|  |  | Total prostate RNA (Cline 1) |
| 633 | 5478-L2-2 | T cells treated with synthetic androgen "R1881" |
| 640 | 5497-R1-1 | Th1eH |
|  |  | Th2eH |
| 651 | 5534-L1-1 | Th2eM |
| 653 | 5554-L2-1 | T cells control |
|  | 5554-R2-1 | T cells treated with synthetic androgen "R1881" |
|  |  | Total prostate RNA (Cline 1) |
|  |  | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | Prostate primary cell line cancer (Cline 8) |
|  |  | Prostate primary cell line normal (Cline 7) |
|  |  | Th1 |
| 664 | 5598-R2-2 | T cells control |
|  |  | T cells treated with synthetic androgen "R1881" |
| 678 | 5638-L1-1 | Th1eH |
|  | 5638-R2-1 | Th2eH |
|  |  | Commercial prostate cell line androgen independent (Cline 2 and 3) |
|  |  | muscle after insulin injection (CTRav) |
|  |  | Total prostate RNA (Cline 1) |
| 728 | 5795-R1-1 | bone_marrow |
|  |  | brain |
|  |  | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | fat |
|  |  | GFP.RV |
|  |  | GFPs |
|  |  | kidney |
|  |  | liver |
|  |  | muscle after insulin injection (CTRav) |
|  |  | muscle after insulin injection to diabetic subject (DIABav) |
|  |  | muscle before insulin injection (CTRav) |
|  |  | muscle before insulin injection to diabetic subject (DIABav) |
|  |  | Prostate primary cell line cancer (Cline 8) |
|  |  | Prostate primary cell line normal + cancer (Cline 6) |
|  |  | Prostate primary cell line normal (Cline 7) |
|  |  | rat oestrogene stimulated |
|  |  | RVp |
|  |  | RVs |
|  |  | RV.Tbet |
|  |  | Sperm (PACH) |
|  |  | Sperm (SR) |
|  |  | spleen |
|  |  | T cells control |
|  |  | testes |
|  |  | Th1_early_human |
|  |  | Th1_early_mouse |

TABLE 5-continued

Validated pre-microRNA Sequences

| SEQ ID NO: | OLIGO ID. | Tissue of Validation |
|---|---|---|
| | | Th1eH |
| | | Th1_late_mouse |
| | | Th2_early_human |
| | | Th2_early_mouse |
| | | Th2eH |
| | | Th2_late_mouse |
| | | Thymocytes |
| | | thymus |
| | | Thymus |
| | | Total prostate RNA (Cline 1) |
| 744 | 5872-L1-1 | Th1eH |
| | 5872-L1-2 | Th2eH |
| | | Th2eM |
| | | Th1eM |
| 753 | 5903-R1-1 | Th1eH |
| | | Th2eH |
| 784 | 6008-R1-1 | Th1eH |
| | | Th2eH |
| 785 | 6016-R2-1 | Commercial prostate cell line androgen independent (Cline 2 and 3) |
| | 6016-R2-2 | Total prostate RNA (Cline 1) |
| 786 | 6023-R1-1 | Th1eH |
| | | Th1lH |
| | | Th2eH |
| | | Th2lH |
| 826 | 6190-R1-1 | Th1eH |
| | | Th2eH |
| 876 | 6404-R1-1 | Th1lH |
| | | Th2lH |
| 903 | 6478-L2-2 | Commercial prostate cell line androgen independent (Cline 2 and 3) |
| | 6478-R2-2 | Commercial prostate cell line immortalized (Cline 5) |
| | | Prostate primary cell line normal (Cline 7) |
| | | T cells control |
| | | T cells treated with synthetic androgen "R1881" |
| 909 | 6509-L1-1 | Th1eH |
| | 6509-L1-2 | Th1lH |
| | | Th2eH |
| | | Th2lH |
| | | Th2eM |
| 911 | 6521-L1-1 | Th1lH |
| | 6521-R1-1 | Th2lH |
| | 6521-R1-2 | fat |
| | | testes |
| | | Th1eH |
| 926 | 6584-L1-1 | Commercial prostate cell line androgen independent (Cline 2 and 3) |
| | | Sperm (SR) |
| | | Th2eH |
| | | Total prostate RNA (Cline 1) |
| 927 | 6587-R1-1 | Th1eH |
| | | Th2eH |
| 940 | 6647-R2-1 | T cells treated with synthetic androgen "R1881" |
| 942 | 6658-L1-1 | Th1lH |
| | | Th2lH |
| 944 | 6664-R2-1 | T cells control |
| | | T cells treated with synthetic androgen "R1881" |
| 946 | 6680-L1-1 | fat |
| | | kidney |
| | | testes |
| 947 | 6681-R1-1 | Commercial prostate cell line androgen dependent (Cline 4) |
| | 6681-R2-2 | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Total prostate RNA (Cline 1) |
| 951 | 6692-L1-1 | Th1eH |
| | | Th2eH |
| 955 | 6712-L2-1 | T cells treated with synthetic androgen "R1881" |
| 963 | 6752-R1-1 | bone_marrow |
| | | brain |
| | | colon |

TABLE 5-continued

Validated pre-microRNA Sequences

| SEQ ID NO: | OLIGO ID. | Tissue of Validation |
|---|---|---|
| | | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFPp |
| | | GFP.RV |
| | | GFPs |
| | | kidney |
| | | liver |
| | | lung |
| | | muscle |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | rat oestrogene stimulated |
| | | RVp |
| | | RVs |
| | | RV.Tbet |
| | | Sperm (PACH) |
| | | Sperm (SR) |
| | | spleen |
| | | T cells control |
| | | T cells treated with synthetic androgen "R1881" |
| | | testes |
| | | Th1 |
| | | Th1_early_human |
| | | Th1_early_mouse |
| | | Th1eH |
| | | Th1eM |
| | | Th1_late_mouse |
| | | Th1lM |
| | | Th2_early_human |
| | | Th2_early_mouse |
| | | Th2eH |
| | | Th2eM |
| | | Th2_late_mouse |
| | | Th2lM |
| | | Thp |
| | | Thymocytes |
| | | thymus |
| | | Thymus |
| | | Total prostate RNA (Cline 1) |
| 967 | 6762-L1-1 | Th1lH |
| | | Th2lH |
| 975 | 6797-R1-1 | T cells treated with synthetic androgen "R1881" |
| 1055 | 7089-R1-1 | Commercial prostate cell line androgen independent (Cline 2 and 3) |
| | | Commercial prostate cell line immortalized (Cline 5) |
| | | fat |
| | | testes |
| | | Th1_early_human |
| | | Th2_early_human |
| | | Total prostate RNA (Cline 1) |
| 1060 | 7104-R2-1 | T cells treated with synthetic androgen "R1881" |
| 1118 | 7356-L2-1 | Total prostate RNA (Cline 1) |
| 1129 | 7385-L1-1 | Th2eM |
| | 7385-L1-2 | Th1eH |
| | | Th2eH |
| 1137 | 7421-R2-1 | Commercial prostate cell line androgen independent (Cline 2 and 3) |
| 1145 | 7440-R1-2 | Th1eH |
| | | Th2eH |
| 1160 | 7522-L1-1 | Th1eH |
| | | Th2eH |
| 1161 | 7527-R2-2 | T cells treated with synthetic androgen "R1881" |
| 1166 | 7548-L1-1 | Th1lH |
| | | Th2lH |
| 1173 | 7571-L1-1 | bone_marrow |
| | 7571-R1-1 | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFPp |
| | | GFP.RV |

TABLE 5-continued

Validated pre-microRNA Sequences

| SEQ ID NO: | OLIGO ID. | Tissue of Validation |
|---|---|---|
| | | Prostate primary cell line cancer (Cline 8) |
| | | Prostate primary cell line normal (Cline 7) |
| | | RVs |
| | | RV.Tbet |
| | | Sperm (PACH) |
| | | Sperm (SR) |
| | | spleen |
| | | T cells control |
| | | testes |
| | | Th1 |
| | | Th1_late_mouse |
| | | Th2_late_mouse |
| | | Thymus |
| | | Total prostate RNA (Cline 1) |
| 1174 | 7572-R2-1 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1175 | 7573-R1-1 | testes |
| 1196 | 7660-L2-1 | Total prostate RNA (Cline 1) |
| 1198 | 7702-L2-1 | Commercial prostate cell line androgen independent (Cline 2 and 3) |
| | 7702-L2-2 | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1205 | | kidney |
| | | testes |
| | | Th1eH |
| | | Th2eH |
| 1207 | 7755-R1-1 | Th1lH |
| | | Th2lH |
| 1217 | 7781-R1-1 | Th1eH |
| | | Th2eH |
| 1233 | 7828-L1-1 | Th1lH |
| | 7828-R1-1 | Th2lH |
| 1238 | 7849-R2-1 | T cells treated with synthetic androgen "R1881" |
| 1251 | 7905-L2-1 | T cells treated with synthetic androgen "R1881" |
| 1267 | 7983-L1-1 | Th1lH |
| 1299 | 8107-R1-1 | Th1lH |
| | | Th2lH |
| 1321 | 8222-R1-2 | Th1lH |
| 1323 | 8231-L1-1 | Th1lH |
| | | Th2eM |
| | | Th2lH |
| 1343 | 8302-L1-1 | Th2lH |
| 1352 | 8355-R1-1 | testes |
| 1396 | 8559-R2-1 | T cells treated with synthetic androgen "R1881" |
| 1403 | 8600-L1-1 | Th1eH |
| | 8600-R1-1 | Th2eH |
| 1485 | 9068-R2-1 | Commercial prostate cell line androgen dependent (Cline 4) |
| | | Commercial prostate cell line androgen independent (Cline 2 and 3) |
| | | Commercial prostate cell line immortalized (Cline 5) |
| | | Prostate primary cell line cancer (Cline 8) |
| | | Prostate primary cell line normal (Cline 7) |
| | | T cells control |
| | | T cells treated with synthetic androgen "R1881" |
| | | Total prostate RNA (Cline 1) |
| 1531 | 9245-R2-1 | Total prostate RNA (Cline 1) |
| 1545 | 9334-L2-2 | T cells treated with synthetic androgen "R1881" |

TABLE 5-continued

Validated pre-microRNA Sequences

| SEQ ID NO: | OLIGO ID. | Tissue of Validation |
|---|---|---|
| 1547 | 9347-R2-1 | T cells control |
|  |  | T cells treated with synthetic androgen "R1881" |
| 1559 | 9387-R2-2 | Commercial prostate cell line androgen independent (Cline 2 and 3) |
|  |  | Total prostate RNA (Cline 1) |
| 1586 | 9541-L1-1 | Th1eH |
| 1592 | 9564-R1-1 | Th1eH |
|  |  | Total prostate RNA (Cline 1) |
| 1601 | 9594-R2-1 | Total prostate RNA (Cline 1) |
| 1610 | 9625-R1-2 | Th2eM |
| 1611 | 9627-L1-1 | testes |
| 1617 | 9644-L1-1 | Th1eH |
|  | 9644-R2-2 | T cells treated with synthetic androgen "R1881" |
| 1634 | 9700-R1-1 | Th1eH |
|  |  | Th2eH |
|  |  | Th2eM |
| 1645 | 9736-R1-1 | Th1eH |
|  |  | Th2eH |
| 1649 | 9753-R1-1 | Th1eH |
|  | 9753-R1-2 | Th2eH |
| 1653 | 9767-L1-1 | Th1eH |
|  | 9767-R1-1 | Th2eH |
| 1656 | 9774-R2-1 | Commercial prostate cell line androgen dependent (Cline 4) |
|  | 9774-R2-2 | Commercial prostate cell line androgen independent (Cline 2 and 3) |
|  |  | Commercial prostate cell line immortalized (Cline 5) |
|  |  | muscle after insulin injection (CTRav) |
|  |  | muscle before insulin injection (CTRav) |
|  |  | Prostate primary cell line cancer (Cline 8) |
|  |  | Prostate primary cell line normal + cancer (Cline 6) |
|  |  | Prostate primary cell line normal (Cline 7) |
|  |  | T cells control |
|  |  | T cells treated with synthetic androgen "R1881" |
|  |  | Th1 |
|  |  | Total prostate RNA (Cline 1) |
| 1661 | 9794-L1-1 | Th1eH |
|  | 9794-L1-2 | Th2eH |
|  | 9794-R1-1 |  |
| 1667 | 9816-R2-1 | Commercial prostate cell line androgen dependent (Cline 4) |
|  |  | T cells control |
|  |  | T cells treated with synthetic androgen "R1881" |
|  |  | Total prostate RNA (Cline 1) |
| 1681 | 9905-L1-1 | Th1eH |
|  |  | Th2eH |
| 1686 | 9936-R2-1 | T cells treated with synthetic androgen "R1881" |
| 1688 | 9955-L1-1 | Th1eH |
|  | 9955-R1-1 | Th1lH |
|  |  | Th2eH |
|  |  | Th2lH |
| 1693 | 9987-R2-2 | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | muscle after insulin injection (CTRav) |
|  |  | muscle before insulin injection (CTRav) |
|  |  | Prostate primary cell line cancer (Cline 8) |
|  |  | Prostate primary cell line normal (Cline 7) |
|  |  | T cells control |
|  |  | T cells treated with synthetic androgen "R1881" |
|  |  | Total prostate RNA (Cline 1) |
| 4773 | 5283-L1-1 | Fat |
|  |  | Testes |
|  |  | T cells |

*Th(½)eH = Th(½) early human  
Th(½)eM = Th(½) early mouse  
Th(½)lH = Th(½) late human  
Th(½)lM = Th(½) late mouse

TABLE 6

Validated microRNA Sequences

| SEQ ID NO: | OLIGO ID. | Tissue of Validation |
|---|---|---|
| 1697 | 8587-R2-1 | Commercial prostate cell line androgen independent (Cline 2 and 3) |
|  | 8587-R2-2 | Commercial prostate cell line immortalized (Cline 5) |

TABLE 6-continued

Validated microRNA Sequences

| SEQ ID NO: | OLIGO ID. | Tissue of Validation |
|---|---|---|
| | 10010-R2-1 | muscle after insulin injection (CTRav) |
| | 10010-R2-2 | muscle before insulin injection (CTRav) |
| | | muscle after insulin injection to diabetic subject (DIABav) |
| | | muscle before insulin injection to diabetic subject (DIABav) |
| | | Prostate primary cell line cancer (Cline 8) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1698 | 8587-R2-1 | Commercial prostate cell line androgen independent (Cline 2 and 3) |
| | 8587-R2-2 | Commercial prostate cell line immortalized (Cline 5) |
| | 10010-R2-1 | muscle after insulin injection (CTRav) |
| | 10010-R2-2 | muscle before insulin injection (CTRav) |
| | | muscle after insulin injection to diabetic subject (DIABav) |
| | | muscle before insulin injection to diabetic subject (DIABav) |
| | | Prostate primary cell line cancer (Cline 8) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1700 | 10018-L1-1 | Th1eH |
| | | Th2eH |
| 1719 | 10058-R1-1 | Th1eH |
| 1720 | 10058-R1-1 | Th1eH |
| 1721 | 10058-R1-1 | Th1eH |
| 1730 | 10093-L2-1 | Commercial prostate cell line androgen dependent (Cline 4) |
| | 10093-R2-1 | Commercial prostate cell line androgen independent (Cline 2 and 3) |
| | 10093-R2-2 | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1731 | 10093-L2-1 | Commercial prostate cell line androgen dependent (Cline 4) |
| | 10093-R2-1 | Commercial prostate cell line androgen independent (Cline 2 and 3) |
| | 10093-R2-2 | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1732 | 10093-L2-1 | Commercial prostate cell line androgen dependent (Cline 4) |
| | 10093-R2-1 | Commercial prostate cell line androgen independent (Cline 2 and 3) |
| | 10093-R2-2 | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1744 | 10138-L2-1 | Commercial prostate cell line androgen dependent (Cline 4) |
| | 10138-L2-2 | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |

TABLE 6-continued

Validated microRNA Sequences

| SEQ ID NO: | OLIGO ID. | Tissue of Validation |
|---|---|---|
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1745 | 10138-L2-1 | Commercial prostate cell line androgen dependent (Cline 4) |
| | 10138-L2-2 | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1746 | 10145-L2-1 | T cells control |
| | | T cells treated with synthetic androgen "R1881" |
| | | Total prostate RNA (Cline 1) |
| 1747 | 10149-R1-1 | bone_marrow |
| | | Th1eH |
| | | Th2eH |
| 1748 | 10149-R1-1 | bone_marrow |
| | | Th1eH |
| | | Th2eH |
| 1749 | 10154-R1-1 | fat |
| | | testes |
| 1750 | 10154-R1-1 | fat |
| | | testes |
| 1784 | 10233-L2-2 | T cells treated with synthetic androgen "R1881" |
| 1785 | 10233-L2-2 | T cells treated with synthetic androgen "R1881" |
| 1805 | 10273-L1-1 | Th1eH |
| | 10273-R1-2 | Th1lH |
| | | Th2eH |
| | | Th2lH |
| 1806 | 10273-L1-1 | Th1eH |
| | 10273-R1-2 | Th1lH |
| | | Th2eH |
| | | Th2lH |
| 1807 | 10273-L1-1 | Th1eH |
| | 10273-R1-2 | Th1lH |
| | | Th2eH |
| | | Th2lH |
| 1815 | 10303-L1-1 | Th2eM |
| 1816 | 10303-L1-1 | Th2eM |
| 1817 | 10303-L1-1 | Th2eM |
| 1818 | 10303-L1-1 | Th2eM |
| 1824 | 10324-L1-1 | Th1eH |
| | 10324-L1-2 | Th2eM |
| 1825 | 10324-L1-1 | Th1eH |
| | 10324-L1-2 | Th2eM |
| 1826 | 10324-L1-1 | Th1eH |
| | 10324-L1-2 | Th2eM |
| 1827 | 10324-L1-1 | Th1eH |
| | 10324-L1-2 | Th2eM |
| 1828 | 10325-R2-1 | T cells treated with synthetic androgen "R1881" |
| 1837 | 10342-R2-2 | Commercial prostate cell line androgen dependent (Cline 4) |
| | | Commercial prostate cell line androgen independent (Cline 2 and 3) |
| | | Commercial prostate cell line immortalized (Cline 5) |
| | | Prostate primary cell line cancer (Cline 8) |
| | | T cells control |
| | | T cells treated with synthetic androgen "R1881" |
| | | Total prostate RNA (Cline 1) |
| 1838 | 10342-R2-2 | Commercial prostate cell line androgen dependent (Cline 4) |
| | | Commercial prostate cell line androgen independent (Cline 2 and 3) |
| | | Commercial prostate cell line immortalized (Cline 5) |
| | | Prostate primary cell line cancer (Cline 8) |
| | | T cells control |
| | | T cells treated with synthetic androgen "R1881" |
| | | Total prostate RNA (Cline 1) |

TABLE 6-continued

Validated microRNA Sequences

| SEQ ID NO: | OLIGO ID. | Tissue of Validation |
|---|---|---|
| 1839 | 10342-R2-2 | Commercial prostate cell line androgen dependent (Cline 4) |
| | | Commercial prostate cell line androgen independent (Cline 2 and 3) |
| | | Commercial prostate cell line immortalized (Cline 5) |
| | | Prostate primary cell line cancer (Cline 8) |
| | | T cells control |
| | | T cells treated with synthetic androgen "R1881" |
| | | Total prostate RNA (Cline 1) |
| 1842 | 10347-L1-2 | Th1eH |
| | | Th2eH |
| 1843 | 10347-L1-2 | Th1eH |
| | | Th2eH |
| 1896 | 10553-L1-1 | Th1lH |
| | 10553-R1-1 | Th2lH |
| | | brain |
| | | Commercial prostate cell line androgen dependent (Cline 4) |
| | | Commercial prostate cell line androgen independent (Cline 2 and 3) |
| | | Commercial prostate cell line immortalized (Cline 5) |
| | | GFP.RV |
| | | kidney |
| | | muscle after insulin injection (CTRav) |
| | | muscle before insulin injection (CTRav) |
| | | Prostate primary cell line cancer (Cline 8) |
| | | Prostate primary cell line normal (Cline 7) |
| | | RVp |
| | | RV.Tbet |
| | | spleen |
| | | T cells control |
| | | T cells treated with synthetic androgen "R1881" |
| | | testes |
| | | Thymocytes |
| | | thymus |
| | | Total prostate RNA (Cline 1) |
| 1897 | 10553-L1-1 | Th1lH |
| | 10553-R1-1 | Th2lH |
| | | brain |
| | | Commercial prostate cell line androgen dependent (Cline 4) |
| | | Commercial prostate cell line androgen independent (Cline 2 and 3) |
| | | Commercial prostate cell line immortalized (Cline 5) |
| | | GFP.RV |
| | | kidney |
| | | muscle after insulin injection (CTRav) |
| | | muscle before insulin injection (CTRav) |
| | | Prostate primary cell line cancer (Cline 8) |
| | | Prostate primary cell line normal (Cline 7) |
| | | RVp |
| | | RV.Tbet |
| | | spleen |
| | | T cells control |
| | | T cells treated with synthetic androgen "R1881" |
| | | testes |
| | | Thymocytes |
| | | thymus |
| | | Total prostate RNA (Cline 1) |
| 1898 | 10562-L1-1 | Th1lH |
| | 10562-L1-2 | Th2eM |
| | | Th2lH |
| | | Th2lH |
| 1899 | 10562-L1-1 | Th1lH |
| | 10562-L1-2 | Th2eM |
| | | Th2lH |
| | | Th2lH |
| 1900 | 10562-L1-1 | Th1lH |
| | 10562-L1-2 | Th2eM |
| | | Th2lH |
| | | Th2lH |
| 1911 | 10615-L1-1 | Th2lH |
| | 10615-L1-2 | Th1lH |
| | 10615-R1-1 | Th2eM |
| 1912 | 10615-L1-1 | Th2lH |
| | 10615-L1-2 | Th1lH |
| | 10615-R1-1 | Th2eM |
| 1913 | 10615-L1-1 | Th2lH |
| | 10615-L1-2 | Th1lH |
| | 10615-R1-1 | Th2eM |
| 1914 | 10617-R1-1 | Th1lH |
| | | Th2lH |

TABLE 6-continued

Validated microRNA Sequences

| SEQ ID NO: | OLIGO ID. | Tissue of Validation |
|---|---|---|
| 1915 | 10617-R1-1 | Th1lH |
| | | Th2lH |
| 1916 | 10617-R1-1 | Th1lH |
| | | Th2lH |
| 1917 | 10617-R1-1 | Th1lH |
| | | Th2lH |
| 1925 | 4155-L1-1 | Th1eM |
| 1926 | 4155-L1-1 | Th1eM |
| 1933 | 3717-L2-1 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1934 | 3717-L2-1 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1944 | 3740-R1-1 | Th2lH |
| 1945 | 3740-R1-1 | Th2lH |
| 1949 | 3755-L1-2 | Th1lH |
| | | Th2eH |
| | | Th2eM |
| | | Th2lH |
| 1950 | 3755-L1-2 | Th1lH |
| | | Th2eH |
| | | Th2eM |
| | | Th2lH |
| 1951 | 8231-L1-1 | Th1lH |
| | 3755-L1-2 | Th2eH |
| | | Th2eM |
| | | Th2lH |
| 1952 | 3758-R2-2 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1953 | 3758-R2-2 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |

TABLE 6-continued

Validated microRNA Sequences

| SEQ ID NO: | OLIGO ID. | Tissue of Validation |
|---|---|---|
| | | T cells treated with synthetic androgen "R1881" |
| | | Th1 |
| | | Total prostate RNA (Cline 1) |
| 1954 | 3758-R2-2 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 1959 | 3784-R1-2 | Th1eH |
| 1960 | 3784-R1-2 | Th1eH |
| 1961 | 3784-R1-2 | Th1eH |
| 1962 | 3784-R1-2 | Th1eH |
| 1963 | 8222-R1-2 | Th1lH |
| 1963 | 3788-R2-2 | T cells treated with synthetic androgen "R1881" |
| 1964 | 8222-R1-2 | Th1lH |
| 1964 | 3788-R2-2 | T cells treated with synthetic androgen "R1881" |
| 1975 | 3817-R1-1 | Th1lH |
| | | Th2eM |
| | | Th2lH |
| 1976 | 3817-R1-1 | Th1lH |
| | | Th2eM |
| | | Th2lH |
| 1977 | 3819-L2-2 | T cells treated with synthetic androgen "R1881" |
| 1978 | 3819-L2-2 | T cells treated with synthetic androgen "R1881" |
| 1979 | 3819-L2-2 | T cells treated with synthetic androgen "R1881" |
| 1990 | 3849-L1-2 | Th1lH |
| | | Th2lH |
| 1991 | 3849-L1-2 | Th1lH |
| | | Th2lH |
| 1992 | 3849-L1-2 | Th1lH |
| | | Th2lH |
| 1993 | 3849-L1-2 | Th1lH |
| | | Th2lH |
| 2000 | 3872-L1-1 | testes |
| 2001 | 3872-L1-1 | testes |
| 2002 | 3872-L1-1 | testes |
| 2025 | 3926-R1-2 | fat |
| | | kidney |
| | | T cells control |
| | | T cells treated with synthetic androgen "R1881" |
| | | testes |
| | | Th1lH |
| 2026 | | fat |
| | | kidney |
| | | T cells control |
| | | T cells treated with synthetic androgen "R1881" |
| | | testes |
| | | Th1lH |
| 2027 | 3931-L1-1 | Th2eH |
| 2028 | 3931-L1-1 | Th2eH |
| 2068 | 3995-L2-1 | T cells control |
| | 3995-L2-2 | T cells treated with synthetic androgen "R1881" |
| | | Total prostate RNA (Cline 1) |
| | | Commercial prostate cell line androgen independent (Cline 2 and 3) |
| | | Total prostate RNA (Cline 1) |
| 2108 | 4088-L1-2 | Th1lM |
| | | Th2lM |
| 2109 | 4088-L1-2 | Th1lM |
| | | Th2lM |
| 2110 | 4088-L1-2 | Th1lM |
| | | Th2lM |
| 2111 | 9977-R2-1 | T cells control |
| | | T cells treated with synthetic androgen "R1881" |
| 2111 | 4097-R2-1 | T cells treated with synthetic androgen "R1881" |
| 2112 | 9977-R2-1 | T cells control |
| | | T cells treated with synthetic androgen "R1881" |
| 2112 | 4097-R2-1 | T cells treated with synthetic androgen "R1881" |

TABLE 6-continued

Validated microRNA Sequences

| SEQ ID NO: | OLIGO ID. | Tissue of Validation |
|---|---|---|
| 2173 | 4284-L1-1 | Th1lH |
|  | 4284-L1-2 | Th2lH |
|  |  | Th2eH |
| 2174 | 4284-L1-1 | Th1lH |
|  | 4284-L1-2 | Th2lH |
|  |  | Th2eH |
| 2175 | 4284-L1-1 | Th1lH |
|  | 4284-L1-2 | Th2lH |
|  |  | Th2eH |
| 2180 | 4303-R1-1 | bone_marrow |
|  | 4303-R1-2 | brain |
|  |  | colon |
|  |  | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | fat |
|  |  | GFPp |
|  |  | GFP.RV |
|  |  | GFPs |
|  |  | kidney |
|  |  | liver |
|  |  | muscle after insulin injection (CTRav) |
|  |  | muscle after insulin injection to diabetic subject (DIABav) |
|  |  | muscle before insulin injection (CTRav) |
|  |  | muscle before insulin injection to diabetic subject (DIABav) |
|  |  | Prostate primary cell line cancer (Cline 8) |
|  |  | Prostate primary cell line normal + cancer (Cline 6) |
|  |  | Prostate primary cell line normal (Cline 7) |
|  |  | rat oestrogene stimulated |
|  |  | RVp |
|  |  | RVs |
|  |  | RV.Tbet |
|  |  | Sperm (PACH) |
|  |  | Sperm (SR) |
|  |  | spleen |
|  |  | T cells control |
|  |  | T cells treated with synthetic androgen "R1881" |
|  |  | testes |
|  |  | Th1 |
|  |  | Th1_early_human |
|  |  | Th1_early_mouse |
|  |  | Th1eH |
|  |  | Th1_late_mouse |
|  |  | Th2_early_human |
|  |  | Th2_early_mouse |
|  |  | Th2eH |
|  |  | Th2_late_mouse |
|  |  | Thp |
|  |  | Thymocytes |
|  |  | thymus |
|  |  | Thymus |
|  |  | Total prostate RNA (Cline 1) |
|  |  | Commercial prostate cell line androgen independent (Cline 2 and 3) |
|  |  | Commercial prostate cell line immortalized (Cline 5) |
|  |  | Prostate primary cell line normal (Cline 7) |
|  |  | RV.Tbet |
|  |  | T cells treated with synthetic androgen "R1881" |
|  |  | thymus |
|  |  | Thymus |
|  |  | Total prostate RNA (Cline 1) |
| 2181 | 4303-R1-1 | bone_marrow |
|  | 4303-R1-2 | brain |
|  |  | colon |
|  |  | Commercial prostate cell line androgen dependent (Cline 4) |
|  |  | Commercial prostate cell line androgen independent (Cline 2 and 3) |
|  |  | Commercial prostate cell line immortalized (Cline 5) |
|  |  | fat |
|  |  | GFPp |
|  |  | GFP.RV |
|  |  | GFPs |
|  |  | kidney |
|  |  | liver |
|  |  | muscle after insulin injection (CTRav) |
|  |  | muscle after insulin injection to diabetic subject (DIABav) |
|  |  | muscle before insulin injection (CTRav) |
|  |  | muscle before insulin injection to diabetic subject (DIABav) |

TABLE 6-continued

Validated microRNA Sequences

| SEQ ID NO: | OLIGO ID. | Tissue of Validation |
|---|---|---|
| | | Prostate primary cell line cancer (Cline 8) |
| | | Prostate primary cell line normal + cancer (Cline 6) |
| | | Prostate primary cell line normal (Cline 7) |
| | | rat oestrogene stimulated |
| | | RVp |
| | | RVs |
| | | RV.Tbet |
| | | Sperm (PACH) |
| | | Sperm (SR) |
| | | spleen |
| | | T cells control |
| | | T cells treated with synthetic androgen "R1881" |
| | | testes |
| | | Th1 |
| | | Th1_early_human |
| | | Th1_early_mouse |
| | | Th1eH |
| | | Th1_late_mouse |
| | | Th2_early_human |
| | | Th2_early_mouse |
| | | Th2eH |
| | | Th2_late_mouse |
| | | Thp |
| | | Thymocytes |
| | | thymus |
| | | Thymus |
| | | Total prostate RNA (Cline 1) |
| | | Commercial prostate cell line androgen independent (Cline 2 and 3) |
| | | Commercial prostate cell line immortalized (Cline 5) |
| | | Prostate primary cell line normal (Cline 7) |
| | | RV.Tbet |
| | | T cells treated with synthetic androgen "R1881" |
| | | thymus |
| | | Thymus |
| | | Total prostate RNA (Cline 1) |
| 2201 | 4352-L1-1 | Th1eH |
| | | Th1lH |
| | | Th2eH |
| | | Th2eM |
| | | Th2lH |
| 2202 | 4352-L1-1 | Th1eH |
| | | Th1lH |
| | | Th2eH |
| | | Th2eM |
| | | Th2lH |
| 2203 | 4352-L1-1 | Th1eH |
| | | Th1lH |
| | | Th2eH |
| | | Th2eM |
| | | Th2lH |
| 2219 | 4392-L1-2 | bone_marrow |
| 2220 | 4392-L1-2 | bone_marrow |
| 2221 | 4392-L1-2 | bone_marrow |
| 2228 | 4417-R1-1 | bone_marrow |
| | | colon |
| | | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFP.RV |
| | | kidney |
| | | liver |
| | | muscle after insulin injection (CTRav) |
| | | muscle before insulin injection (CTRav) |
| | | Prostate primary cell line cancer (Cline 8) |
| | | Prostate primary cell line normal + cancer (Cline 6) |
| | | Prostate primary cell line normal (Cline 7) |
| | | RV.Tbet |
| | | Sperm (SR) |
| | | spleen |
| | | T cells control |
| | | testes |
| | | Th1 |
| | | Th1_early_human |
| | | Th1_early_mouse |
| | | Th1_late_mouse |

TABLE 6-continued

Validated microRNA Sequences

| SEQ ID NO: | OLIGO ID. | Tissue of Validation |
|---|---|---|
| | | Th2_early_human |
| | | Th2_early_mouse |
| | | Th2_late_mouse |
| | | Thp |
| | | thymus |
| | | Thymus |
| | | Total prostate RNA (Cline 1) |
| 2229 | 4417-R1-1 | bone_marrow |
| | | colon |
| | | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFP.RV |
| | | kidney |
| | | liver |
| | | muscle after insulin injection (CTRav) |
| | | muscle before insulin injection (CTRav) |
| | | Prostate primary cell line cancer (Cline 8) |
| | | Prostate primary cell line normal + cancer (Cline 6) |
| | | Prostate primary cell line normal (Cline 7) |
| | | RV.Tbet |
| | | Sperm (SR) |
| | | spleen |
| | | T cells control |
| | | testes |
| | | Th1 |
| | | Th1_early_human |
| | | Th1_early_mouse |
| | | Th1_late_mouse |
| | | Th2_early_human |
| | | Th2_early_mouse |
| | | Th2_late_mouse |
| | | Thp |
| | | thymus |
| | | Thymus |
| | | Total prostate RNA (Cline 1) |
| 2231 | 4432-L1-1 | Th1eH |
| | 4432-L1-2 | Th2eH |
| | 4432-R1-1 | |
| 2232 | 4432-L1-1 | Th1eH |
| | 4432-L1-2 | Th2eH |
| | 4432-R1-1 | |
| 2233 | 4432-L1-1 | Th1eH |
| | 4432-L1-2 | Th2eH |
| | 4432-R1-1 | |
| 2234 | 4432-L1-1 | Th1eH |
| | 4432-L1-2 | Th2eH |
| | 4432-R1-1 | |
| 2260 | 4482-R1-1 | Th1eH |
| 2278 | 4528-R1-1 | Th1lH |
| | | Th2lH |
| 2279 | 4528-R1-1 | Th1lH |
| | | Th2lH |
| 2280 | 4528-R1-1 | Th1lH |
| | | Th2lH |
| 2313 | 4638-L1-1 | Th2eM |
| 2314 | 4638-L1-1 | Th2eM |
| 2389 | 4829-R2-1 | Commercial prostate cell line androgen dependent (Cline 4) |
| | 4829-R2-2 | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| | | T cells treated with synthetic androgen "R1881" |
| 2390 | 4829-R2-1 | Commercial prostate cell line androgen dependent (Cline 4) |
| | 4829-R2-2 | Commercial prostate cell line androgen independent (Cline 2 and 3) |
| | | Commercial prostate cell line immortalized (Cline 5) |

TABLE 6-continued

Validated microRNA Sequences

| SEQ ID NO: | OLIGO ID. | Tissue of Validation |
|---|---|---|
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| | | T cells treated with synthetic androgen "R1881" |
| 2399 | 4875-R2-2 | Total prostate RNA (Cline 1) |
| 2408 | 4892-L1-1 | Th1lH |
| | 4892-R1-1 | Th2lH |
| | 4892-R1-2 | |
| 2409 | 4892-L1-1 | Th1lH |
| | 4892-R1-1 | Th2lH |
| | 4892-R1-2 | |
| 2410 | 4892-L1-1 | Th1lH |
| | 4892-R1-1 | Th2lH |
| | 4892-R1-2 | |
| 2427 | 4939-L1-2 | Th1lH |
| | 4939-R1-2 | Th2lH |
| | | fat |
| | | testes |
| 2428 | 4939-L1-2 | Th1lH |
| | 4939-R1-2 | Th2lH |
| | | fat |
| | | testes |
| 2429 | 4939-L1-2 | Th1lH |
| | 4939-R1-2 | Th2lH |
| | | fat |
| | | testes |
| 2430 | 4939-L1-2 | Th1lH |
| | 4939-R1-2 | Th2lH |
| | | fat |
| | | testes |
| 2431 | 4946-L1-1 | Th2eH |
| | 4946-R1-1 | Th1lH |
| | | Th2eM |
| | | Th2lH |
| 2432 | 4946-L1-1 | Th2eH |
| | 4946-R1-1 | Th1lH |
| | | Th2eM |
| | | Th2lH |
| 2433 | 4946-L1-1 | Th2eH |
| | 4946-R1-1 | Th1lH |
| | | Th2eM |
| | | Th2lH |
| 2434 | 4946-L1-1 | Th2eH |
| | 4946-R1-1 | Th1lH |
| | | Th2eM |
| | | Th2lH |
| 2437 | 4958-R2-2 | T cells control |
| | | T cells treated with synthetic androgen "R1881" |
| 2438 | 4958-R2-2 | T cells control |
| | | T cells treated with synthetic androgen "R1881" |
| 2450 | 4983-L1-1 | Th1lH |
| | | Th2eM |
| | | Th2lH |
| 2451 | 4983-L1-1 | Th1lH |
| | | Th2eM |
| | | Th2lH |
| 2469 | 5063-L2-2 | T cells treated with synthetic androgen "R1881" |
| 2470 | 5063-L2-2 | T cells treated with synthetic androgen "R1881" |
| 2471 | 5063-L2-2 | T cells treated with synthetic androgen "R1881" |
| 2476 | 5070-L1-1 | Th1lH |
| | | Th2eM |
| | | Th2lH |
| 2477 | 5071-R2-1 | Commercial prostate cell line androgen independent (Cline 2 and 3) |
| | | T cells control |
| | | T cells treated with synthetic androgen "R1881" |
| | | Total prostate RNA (Cline 1) |
| 2523 | 5193-R1-1 | testes |

TABLE 6-continued

Validated microRNA Sequences

| SEQ ID NO: | OLIGO ID. | Tissue of Validation |
|---|---|---|
| 2532 | 5232-L2-1 | Commercial prostate cell line androgen independent (Cline 2 and 3)<br>Total prostate RNA (Cline 1) |
| 2584 | 5380-R2-2 | Commercial prostate cell line androgen dependent (Cline 4)<br>Commercial prostate cell line androgen independent (Cline 2 and 3)<br>Commercial prostate cell line immortalized (Cline 5)<br>Prostate primary cell line cancer (Cline 8)<br>Prostate primary cell line normal (Cline 7)<br>Total prostate RNA (Cline 1) |
| 2585 | 5380-R2-2 | Commercial prostate cell line androgen dependent (Cline 4)<br>Commercial prostate cell line androgen independent (Cline 2 and 3)<br>Commercial prostate cell line immortalized (Cline 5)<br>Prostate primary cell line cancer (Cline 8)<br>Prostate primary cell line normal (Cline 7)<br>Total prostate RNA (Cline 1) |
| 2586 | 5380-R2-2 | Commercial prostate cell line androgen dependent (Cline 4)<br>Commercial prostate cell line androgen independent (Cline 2 and 3)<br>Commercial prostate cell line immortalized (Cline 5)<br>Prostate primary cell line cancer (Cline 8)<br>Prostate primary cell line normal (Cline 7)<br>Total prostate RNA (Cline 1) |
| 2587 | 5380-R2-2 | Commercial prostate cell line androgen dependent (Cline 4)<br>Commercial prostate cell line androgen independent (Cline 2 and 3)<br>Commercial prostate cell line immortalized (Cline 5)<br>Prostate primary cell line cancer (Cline 8)<br>Prostate primary cell line normal (Cline 7)<br>Total prostate RNA (Cline 1) |
| 2613 | 5478-L2-2 | T cells treated with synthetic androgen "R1881" |
| 2620 | 5497-R1-1 | Th1eH<br>Th2eH |
| 2621 | 5497-R1-1 | Th1eH<br>Th2eH |
| 2622 | 5497-R1-1 | Th1eH<br>Th2eH |
| 2637 | 5534-L1-1 | Th2eM |
| 2648 | 5598-R2-2 | T cells control<br>T cells treated with synthetic androgen "R1881" |
| 2649 | 5598-R2-2 | T cells control<br>T cells treated with synthetic androgen "R1881" |
| 2730 | 5795-R1-1 | bone_marrow<br>brain<br>Commercial prostate cell line androgen dependent (Cline 4)<br>Commercial prostate cell line androgen independent (Cline 2 and 3)<br>Commercial prostate cell line immortalized (Cline 5)<br>fat<br>GFP.RV<br>GFPs<br>kidney<br>liver<br>muscle after insulin injection (CTRav)<br>muscle after insulin injection to diabetic subject (DIABav)<br>muscle before insulin injection (CTRav)<br>muscle before insulin injection to diabetic subject (DIABav)<br>Prostate primary cell line cancer (Cline 8)<br>Prostate primary cell line normal + cancer (Cline 6)<br>Prostate primary cell line normal (Cline 7)<br>rat oestrogene stimulated<br>RVp<br>RVs<br>RV.Tbet<br>Sperm (PACH)<br>Sperm (SR)<br>spleen<br>T cells control<br>testes<br>Th1_early_human<br>Th1_early_mouse<br>Th1eH<br>Th1_late_mouse<br>Th2_early_human<br>Th2_early_mouse<br>Th2eH<br>Th2_late_mouse<br>Thymocytes<br>thymus<br>Thymus<br>Total prostate RNA (Cline 1) |

TABLE 6-continued

Validated microRNA Sequences

| SEQ ID NO: | OLIGO ID. | Tissue of Validation |
|---|---|---|
| 2754 | 5872-L1-1 | Th1eH |
|  | 5872-L1-2 | Th2eH |
|  |  | Th2eM |
|  |  | Th1eM |
| 2755 | 5872-L1-1 | Th1eH |
|  | 5872-L1-2 | Th2eH |
|  |  | Th2eM |
|  |  | Th1eM |
| 2756 | 5872-L1-1 | Th1eH |
|  | 5872-L1-2 | Th2eH |
|  |  | Th2eM |
|  |  | Th1eM |
| 2771 | 5903-R1-1 | Th1eH |
|  |  | Th2eH |
| 2809 | 6008-R1-1 | Th1eH |
|  |  | Th2eH |
| 2810 | 6008-R1-1 | Th1eH |
|  |  | Th2eH |
| 2811 | 6016-R2-1 | Commercial prostate cell line androgen independent (Cline 2 and 3) |
|  | 6016-R2-2 | Total prostate RNA (Cline 1) |
| 2812 | 6016-R2-1 | Commercial prostate cell line androgen independent (Cline 2 and 3) |
|  | 6016-R2-2 | Total prostate RNA (Cline 1) |
| 2813 | 6016-R2-1 | Commercial prostate cell line androgen independent (Cline 2 and 3) |
|  | 6016-R2-2 | Total prostate RNA (Cline 1) |
| 2814 | 6023-R1-1 | Th1eH |
|  |  | Th1lH |
|  |  | Th2eH |
|  |  | Th2lH |
| 2815 | 6023-R1-1 | Th1eH |
|  |  | Th1lH |
|  |  | Th2eH |
|  |  | Th2lH |
| 2862 | 6190-R1-1 | Th1eH |
|  |  | Th2eH |
| 2863 | 6190-R1-1 | Th1eH |
|  |  | Th2eH |
| 2864 | 6190-R1-1 | Th1eH |
|  |  | Th2eH |
| 2928 | 6404-R1-1 | Th1lH |
|  |  | Th2lH |
| 2929 | 6404-R1-1 | Th1lH |
|  |  | Th2lH |
| 2958 | 6478-L2-2 | Commercial prostate cell line androgen independent (Cline 2 and 3) |
|  | 6478-R2-2 | Commercial prostate cell line immortalized (Cline 5) |
|  |  | Prostate primary cell line normal (Cline 7) |
|  |  | T cells control |
|  |  | T cells treated with synthetic androgen "R1881" |
| 2959 | 6478-L2-2 | Commercial prostate cell line androgen independent (Cline 2 and 3) |
|  | 6478-R2-2 | Commercial prostate cell line immortalized (Cline 5) |
|  |  | Prostate primary cell line normal (Cline 7) |
|  |  | T cells control |
|  |  | T cells treated with synthetic androgen "R1881" |
| 2960 | 6478-L2-2 | Commercial prostate cell line androgen independent (Cline 2 and 3) |
|  | 6478-R2-2 | Commercial prostate cell line immortalized (Cline 5) |
|  |  | Prostate primary cell line normal (Cline 7) |
|  |  | T cells control |
|  |  | T cells treated with synthetic androgen "R1881" |
| 2961 | 6478-L2-2 | Commercial prostate cell line androgen independent (Cline 2 and 3) |
|  | 6478-R2-2 | Commercial prostate cell line immortalized (Cline 5) |
|  |  | Prostate primary cell line normal (Cline 7) |
|  |  | T cells control |
|  |  | T cells treated with synthetic androgen "R1881" |
| 2966 | 6509-L1-1 | Th1eH |
|  | 6509-L1-2 | Th1lH |
|  |  | Th2eH |
|  |  | Th2lH |
|  |  | Th2eM |
| 2967 | 6509-L1-1 | Th1eH |
|  | 6509-L1-2 | Th1lH |
|  |  | Th2eH |
|  |  | Th2lH |
|  |  | Th2eM |
| 2968 | 6509-L1-1 | Th1eH |
|  | 6509-L1-2 | Th1lH |
|  |  | Th2eH |

TABLE 6-continued

Validated microRNA Sequences

| SEQ ID NO: | OLIGO ID. | Tissue of Validation |
|---|---|---|
| | | Th2lH |
| | | Th2eM |
| 2971 | 6521-L1-1 | Th1lH |
| | 6521-R1-1 | Th2lH |
| | 6521-R1-2 | fat |
| | | testes |
| | | Th1eH |
| 2972 | 6521-L1-1 | Th1lH |
| | 6521-R1-1 | Th2lH |
| | 6521-R1-2 | fat |
| | | testes |
| | | Th1eH |
| 2973 | 6521-L1-1 | Th1lH |
| | 6521-R1-1 | Th2lH |
| | 6521-R1-2 | fat |
| | | testes |
| | | Th1eH |
| 2974 | 6521-L1-1 | Th1lH |
| | 6521-R1-1 | Th2lH |
| | 6521-R1-2 | fat |
| | | testes |
| | | Th1eH |
| 2999 | 6584-L1-1 | Commercial prostate cell line androgen independent (Cline 2 and 3) |
| | | Sperm (SR) |
| | | Th2eH |
| | | Total prostate RNA (Cline 1) |
| 3000 | 6587-R1-1 | Th1eH |
| | | Th2eH |
| 3001 | 6587-R1-1 | Th1eH |
| | | Th2eH |
| 3015 | 6647-R2-1 | T cells treated with synthetic androgen "R1881" |
| 3017 | 6658-L1-1 | Th1lH |
| | | Th2lH |
| 3018 | 6658-L1-1 | Th1lH |
| | | Th2lH |
| 3019 | 6658-L1-1 | Th1lH |
| | | Th2lH |
| 3021 | 6664-R2-1 | T cells control |
| | | T cells treated with synthetic androgen "R1881" |
| 3023 | 6680-L1-1 | fat |
| | | kidney |
| | | testes |
| 3024 | 6680-L1-1 | fat |
| | | kidney |
| | | testes |
| 3025 | 6681-R1-1 | Commercial prostate cell line androgen dependent (Cline 4) |
| | 6681-R2-2 | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Total prostate RNA (Cline 1) |
| 3026 | 6681-R1-1 | Commercial prostate cell line androgen dependent (Cline 4) |
| | 6681-R2-2 | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Total prostate RNA (Cline 1) |
| 3027 | 6681-R1-1 | Commercial prostate cell line androgen dependent (Cline 4) |
| | 6681-R2-2 | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |

TABLE 6-continued

Validated microRNA Sequences

| SEQ ID NO: | OLIGO ID. | Tissue of Validation |
|---|---|---|
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Total prostate RNA (Cline 1) |
| 3029 | 6692-L1-1 | Th1eH |
| | | Th2eH |
| 3030 | 6692-L1-1 | Th1eH |
| | | Th2eH |
| 3038 | 6712-L2-1 | T cells treated with synthetic androgen "R1881" |
| 3039 | 6712-L2-1 | T cells treated with synthetic androgen "R1881" |
| 3048 | 6752-R1-1 | bone_marrow |
| | | brain |
| | | colon |
| | | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFPp |
| | | GFP.RV |
| | | GFPs |
| | | kidney |
| | | liver |
| | | lung |
| | | muscle |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | rat oestrogene stimulated |
| | | RVp |
| | | RVs |
| | | RV.Tbet |
| | | Sperm (PACH) |
| | | Sperm (SR) |
| | | spleen |
| | | T cells control |
| | | T cells treated with synthetic androgen "R1881" |
| | | testes |
| | | Th1 |
| | | Th1_early_human |
| | | Th1_early_mouse |
| | | Th1eH |
| | | Th1eM |
| | | Th1_late_mouse |
| | | Th1lM |
| | | Th2_early_human |
| | | Th2_early_mouse |
| | | Th2eH |
| | | Th2eM |
| | | Th2_late_mouse |
| | | Th2lM |
| | | Thp |
| | | Thymocytes |
| | | thymus |
| | | Thymus |
| | | Total prostate RNA (Cline 1) |
| 3049 | 6752-R1-1 | bone_marrow |
| | | brain |
| | | colon |
| | | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFPp |
| | | GFP.RV |
| | | GFPs |
| | | kidney |
| | | liver |
| | | lung |

TABLE 6-continued

Validated microRNA Sequences

| SEQ ID NO: | OLIGO ID. | Tissue of Validation |
|---|---|---|
| | | muscle |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | rat oestrogene stimulated |
| | | RVp |
| | | RVs |
| | | RV.Tbet |
| | | Sperm (PACH) |
| | | Sperm (SR) |
| | | spleen |
| | | T cells control |
| | | T cells treated with synthetic androgen "R1881" |
| | | testes |
| | | Th1 |
| | | Th1_early_human |
| | | Th1_early_mouse |
| | | Th1eH |
| | | Th1eM |
| | | Th1_late_mouse |
| | | Th1lM |
| | | Th2_early_human |
| | | Th2_early_mouse |
| | | Th2eH |
| | | Th2eM |
| | | Th2_late_mouse |
| | | Th2lM |
| | | Thp |
| | | Thymocytes |
| | | thymus |
| | | Thymus |
| | | Total prostate RNA (Cline 1) |
| 3050 | 6752-R1-1 | bone_marrow |
| | | brain |
| | | colon |
| | | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFPp |
| | | GFP.RV |
| | | GFPs |
| | | kidney |
| | | liver |
| | | lung |
| | | muscle |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | rat oestrogene stimulated |
| | | RVp |
| | | RVs |
| | | RV.Tbet |
| | | Sperm (PACH) |
| | | Sperm (SR) |
| | | spleen |
| | | T cells control |
| | | T cells treated with synthetic androgen "R1881" |
| | | testes |
| | | Th1 |
| | | Th1_early_human |
| | | Th1_early_mouse |
| | | Th1eH |
| | | Th1eM |
| | | Th1_late_mouse |
| | | Th1lM |
| | | Th2_early_human |
| | | Th2_early_mouse |

TABLE 6-continued

Validated microRNA Sequences

| SEQ ID NO: | OLIGO ID. | Tissue of Validation |
|---|---|---|
| | | Th2eH |
| | | Th2eM |
| | | Th2_late_mouse |
| | | Th2lM |
| | | Thp |
| | | Thymocytes |
| | | thymus |
| | | Thymus |
| | | Total prostate RNA (Cline 1) |
| 3052 | 6762-L1-1 | Th1lH |
| | | Th2lH |
| 3053 | 6762-L1-1 | Th1lH |
| | | Th2lH |
| 3054 | 6762-L1-1 | Th1lH |
| | | Th2lH |
| 3061 | 6797-R1-1 | T cells treated with synthetic androgen "R1881" |
| 3062 | 6797-R1-1 | T cells treated with synthetic androgen "R1881" |
| 3162 | 7104-R2-1 | T cells treated with synthetic androgen "R1881" |
| 3232 | 7356-L2-1 | Total prostate RNA (Cline 1) |
| 3233 | 7356-L2-1 | Total prostate RNA (Cline 1) |
| 3249 | 7385-L1-1 | Th2eM |
| | 7385-L1-2 | Th1eH |
| | | Th2eH |
| 3250 | 7385-L1-1 | Th2eM |
| | 7385-L1-2 | Th1eH |
| | | Th2eH |
| 3261 | 7421-R2-1 | Commercial prostate cell line androgen independent (Cline 2 and 3) |
| 3271 | 7440-R1-2 | Th1eH |
| | | Th2eH |
| 3272 | 7440-R1-2 | Th1eH |
| | | Th2eH |
| 3273 | 7440-R1-2 | Th1eH |
| | | Th2eH |
| 3274 | 7440-R1-2 | Th1eH |
| | | Th2eH |
| 3300 | 7522-L1-1 | Th1eH |
| | | Th2eH |
| 3301 | 7522-L1-1 | Th1eH |
| | | Th2eH |
| 3302 | 7527-R2-2 | T cells treated with synthetic androgen "R1881" |
| 3303 | 7527-R2-2 | T cells treated with synthetic androgen "R1881" |
| 3304 | 7527-R2-2 | T cells treated with synthetic androgen "R1881" |
| 3320 | 7571-L1-1 | bone_marrow |
| | 7571-R1-1 | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFPp |
| | | GFP.RV |
| | | Prostate primary cell line cancer (Cline 8) |
| | | Prostate primary cell line normal (Cline 7) |
| | | RVs |
| | | RV.Tbet |
| | | Sperm (PACH) |
| | | Sperm (SR) |
| | | spleen |
| | | T cells control |
| | | testes |
| | | Th1 |
| | | Th1_late_mouse |
| | | Th2_late_mouse |
| | | Thymus |
| | | Total prostate RNA (Cline 1) |
| 3321 | 7571-L1-1 | bone_marrow |
| | 7571-R1-1 | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFPp |
| | | GFP.RV |
| | | Prostate primary cell line cancer (Cline 8) |
| | | Prostate primary cell line normal (Cline 7) |
| | | RVs |
| | | RV.Tbet |
| | | Sperm (PACH) |
| | | Sperm (SR) |

TABLE 6-continued

Validated microRNA Sequences

| SEQ ID NO: | OLIGO ID. | Tissue of Validation |
|---|---|---|
| | | spleen |
| | | T cells control |
| | | testes |
| | | Th1 |
| | | Th1_late_mouse |
| | | Th2_late_mouse |
| | | Thymus |
| | | Total prostate RNA (Cline 1) |
| 3322 | 7571-L1-1 | bone_marrow |
| | 7571-R1-1 | Commercial prostate cell line androgen dependent (Cline 4) |
| | | Commercial prostate cell line androgen independent (Cline 2 and 3) |
| | | Commercial prostate cell line immortalized (Cline 5) |
| | | fat |
| | | GFPp |
| | | GFP.RV |
| | | Prostate primary cell line cancer (Cline 8) |
| | | Prostate primary cell line normal (Cline 7) |
| | | RVs |
| | | RV.Tbet |
| | | Sperm (PACH) |
| | | Sperm (SR) |
| | | spleen |
| | | T cells control |
| | | testes |
| | | Th1 |
| | | Th1_late_mouse |
| | | Th2_late_mouse |
| | | Thymus |
| | | Total prostate RNA (Cline 1) |
| 3323 | 7572-R2-1 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 3324 | 7572-R2-1 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 3325 | 7572-R2-1 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle after insulin injection to diabetic subject (DIABav) |
| | | muscle before insulin injection (CTRav) |
| | | muscle before insulin injection to diabetic subject (DIABav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 3326 | 7573-R1-1 | testes |
| 3327 | 7573-R1-1 | testes |
| 3328 | 7573-R1-1 | testes |
| 3329 | 7573-R1-1 | testes |
| 3358 | 7660-L2-1 | Total prostate RNA (Cline 1) |

TABLE 6-continued

Validated microRNA Sequences

| SEQ ID NO: | OLIGO ID. | Tissue of Validation |
|---|---|---|
| 3359 | 7660-L2-1 | Total prostate RNA (Cline 1) |
| 3360 | 7660-L2-1 | Total prostate RNA (Cline 1) |
| 3363 | 7702-L2-1 | Commercial prostate cell line androgen independent (Cline 2 and 3) |
|  | 7702-L2-2 | Commercial prostate cell line immortalized (Cline 5) |
|  |  | muscle after insulin injection (CTRav) |
|  |  | muscle after insulin injection to diabetic subject (DIABav) |
|  |  | muscle before insulin injection (CTRav) |
|  |  | muscle before insulin injection to diabetic subject (DIABav) |
|  |  | Prostate primary cell line cancer (Cline 8) |
|  |  | Prostate primary cell line normal (Cline 7) |
|  |  | T cells control |
|  |  | T cells treated with synthetic androgen "R1881" |
|  |  | Th1 |
|  |  | Total prostate RNA (Cline 1) |
| 3372 | 7747-R1-1 | kidney |
|  |  | testes |
|  |  | Th1eH |
|  |  | Th2eH |
| 3373 | 7747-R1-1 | kidney |
|  |  | testes |
|  |  | Th1eH |
|  |  | Th2eH |
| 3374 | 7747-R1-1 | kidney |
|  |  | testes |
|  |  | Th1eH |
|  |  | Th2eH |
| 3375 | 7747-R1-1 | kidney |
|  |  | testes |
|  |  | Th1eH |
|  |  | Th2eH |
| 3378 | 7755-R1-1 | Th1lH |
|  |  | Th2lH |
| 3379 | 7755-R1-1 | Th1lH |
|  |  | Th2lH |
| 3391 | 7781-R1-1 | Th1eH |
|  |  | Th2eH |
| 3392 | 7781-R1-1 | Th1eH |
|  |  | Th2eH |
| 3416 | 7828-L1-1 | Th1lH |
|  | 7828-R1-1 | Th2lH |
| 3417 | 7828-L1-1 | Th1lH |
|  | 7828-R1-1 | Th2lH |
| 3422 | 7849-R2-1 | T cells treated with synthetic androgen "R1881" |
| 3423 | 7849-R2-1 | T cells treated with synthetic androgen "R1881" |
| 3424 | 7849-R2-1 | T cells treated with synthetic androgen "R1881" |
| 3440 | 7905-L2-1 | T cells treated with synthetic androgen "R1881" |
| 3441 | 7905-L2-1 | T cells treated with synthetic androgen "R1881" |
| 3442 | 7905-L2-1 | T cells treated with synthetic androgen "R1881" |
| 3461 | 7983-L1-1 | Th1lH |
| 3497 | 8107-R1-1 | Th1lH |
|  |  | Th2lH |
| 3498 | 8107-R1-1 | Th1lH |
|  |  | Th2lH |
| 3499 | 8107-R1-1 | Th1lH |
|  |  | Th2lH |
| 3528 | 8231-L1-1 | Th1lH |
|  |  | Th2eM |
|  |  | Th2lH |
| 3555 | 8302-L1-1 | Th2lH |
| 3556 | 8302-L1-1 | Th2lH |
| 3557 | 8302-L1-1 | Th2lH |
| 3567 | 8355-R1-1 | testes |
| 3619 | 8559-R2-1 | T cells treated with synthetic androgen "R1881" |
| 3620 | 8559-R2-1 | T cells treated with synthetic androgen "R1881" |
| 3621 | 8559-R2-1 | T cells treated with synthetic androgen "R1881" |
| 3627 | 8600-L1-1 | Th1eH |
|  | 8600-R1-1 | Th2eH |
| 3628 | 8600-L1-1 | Th1eH |
|  | 8600-R1-1 | Th2eH |
| 3786 | 9245-R2-1 | Total prostate RNA (Cline 1) |
| 3804 | 9334-L2-2 | T cells treated with synthetic androgen "R1881" |
| 3805 | 9334-L2-2 | T cells treated with synthetic androgen "R1881" |
| 3806 | 9334-L2-2 | T cells treated with synthetic androgen "R1881" |
| 3807 | 9334-L2-2 | T cells treated with synthetic androgen "R1881" |
| 3808 | 9347-R2-1 | T cells control |
|  |  | T cells treated with synthetic androgen "R1881" |

TABLE 6-continued

Validated microRNA Sequences

| SEQ ID NO: | OLIGO ID. | Tissue of Validation |
|---|---|---|
| 3825 | 9387-R2-2 | Commercial prostate cell line androgen independent (Cline 2 and 3) |
| | | Total prostate RNA (Cline 1) |
| 3862 | 9541-L1-1 | Th1eH |
| 3863 | 9541-L1-1 | Th1eH |
| 3870 | 9564-R1-1 | Th1eH |
| | | Total prostate RNA (Cline 1) |
| 3871 | 9564-R1-1 | Th1eH |
| | | Total prostate RNA (Cline 1) |
| 3880 | 9594-R2-1 | Total prostate RNA (Cline 1) |
| 3881 | 9594-R2-1 | Total prostate RNA (Cline 1) |
| 3882 | 9594-R2-1 | Total prostate RNA (Cline 1) |
| 3896 | 9625-R1-2 | Th2eM |
| 3897 | 9625-R1-2 | Th2eM |
| 3898 | 9625-R1-2 | Th2eM |
| 3912 | 9644-L1-1 | Th1eH |
| | 9644-R2-2 | T cells treated with synthetic androgen "R1881" |
| 3931 | 9700-R1-1 | Th1eH |
| | | Th2eH |
| | | Th2eM |
| 3943 | 9736-R1-1 | Th1eH |
| | | Th2eH |
| 3950 | 9753-R1-1 | Th1eH |
| | 9753-R1-2 | Th2eH |
| 3951 | 9753-R1-1 | Th1eH |
| | 9753-R1-2 | Th2eH |
| 3956 | 9767-L1-1 | Th1eH |
| | 9767-R1-1 | Th2eH |
| 3957 | 9767-L1-1 | Th1eH |
| | 9767-R1-1 | Th2eH |
| 3959 | 9774-R2-1 | Commercial prostate cell line androgen dependent (Cline 4) |
| | 9774-R2-2 | Commercial prostate cell line androgen independent (Cline 2 and 3) |
| | | Commercial prostate cell line immortalized (Cline 5) |
| | | muscle after insulin injection (CTRav) |
| | | muscle before insulin injection (CTRav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 3960 | 9774-R2-1 | Commercial prostate cell line androgen dependent (Cline 4) |
| | 9774-R2-2 | Commercial prostate cell line androgen independent (Cline 2 and 3) |
| | | Commercial prostate cell line immortalized (Cline 5) |
| | | muscle after insulin injection (CTRav) |
| | | muscle before insulin injection (CTRav) |
| | | Prostate primary cell line cancer (Cline 8) |
| | | Prostate primary cell line normal + cancer (Cline 6) |
| | | Prostate primary cell line normal (Cline 7) |
| | | T cells control |
| | | T cells treated with synthetic androgen "R1881" |
| | | Th1 |
| | | Total prostate RNA (Cline 1) |
| 3966 | 9794-L1-1 | Th1eH |
| | 9794-L1-2 | Th2eH |
| | 9794-R1-1 | |
| 3967 | 9794-L1-1 | Th1eH |
| | 9794-L1-2 | Th2eH |
| | 9794-R1-1 | |
| 3968 | 9794-L1-1 | Th1eH |
| | 9794-L1-2 | Th2eH |
| | 9794-R1-1 | |
| 3973 | 9816-R2-1 | Commercial prostate cell line androgen dependent (Cline 4) |
| | | T cells control |
| | | T cells treated with synthetic androgen "R1881" |
| | | Total prostate RNA (Cline 1) |
| 3974 | 9816-R2-1 | Commercial prostate cell line androgen dependent (Cline 4) |
| | | T cells control |
| | | T cells treated with synthetic androgen "R1881" |
| | | Total prostate RNA (Cline 1) |
| 3975 | 9816-R2-1 | Commercial prostate cell line androgen dependent (Cline 4) |
| | | T cells control |
| | | T cells treated with synthetic androgen "R1881" |
| | | Total prostate RNA (Cline 1) |
| 3976 | 9816-R2-1 | Commercial prostate cell line androgen dependent (Cline 4) |
| | | T cells control |

TABLE 6-continued

Validated microRNA Sequences

| SEQ ID NO: | OLIGO ID. | Tissue of Validation |
|---|---|---|
| | | T cells treated with synthetic androgen "R1881" |
| | | Total prostate RNA (Cline 1) |
| 3986 | 9905-L1-1 | Th1eH |
| | | Th2eH |
| 3987 | 9905-L1-1 | Th1eH |
| | | Th2eH |
| 3991 | 9936-R2-1 | T cells treated with synthetic androgen "R1881" |
| 3992 | 9936-R2-1 | T cells treated with synthetic androgen "R1881" |
| 3993 | 9955-L1-1 | Th1eH |
| | 9955-R1-1 | Th1lH |
| | | Th2eH |
| | | Th2lH |
| 3994 | 9955-L1-1 | Th1eH |
| | 9955-R1-1 | Th1lH |
| | | Th2eH |
| | | Th2lH |
| 4001 | 9987-R2-2 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle before insulin injection (CTRav) |
| | | Prostate primary cell line cancer (Cline 8) |
| | | Prostate primary cell line normal (Cline 7) |
| | | T cells control |
| | | T cells treated with synthetic androgen "R1881" |
| | | Total prostate RNA (Cline 1) |
| 4002 | 9987-R2-2 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle before insulin injection (CTRav) |
| | | Prostate primary cell line cancer (Cline 8) |
| | | Prostate primary cell line normal (Cline 7) |
| | | T cells control |
| | | T cells treated with synthetic androgen "R1881" |
| | | Total prostate RNA (Cline 1) |
| 4003 | 9987-R2-2 | Commercial prostate cell line androgen dependent (Cline 4) |
| | | Commercial prostate cell line androgen independent (Cline 2 and 3) |
| | | Commercial prostate cell line immortalized (Cline 5) |
| | | muscle after insulin injection (CTRav) |
| | | muscle before insulin injection (CTRav) |
| | | Prostate primary cell line cancer (Cline 8) |
| | | Prostate primary cell line normal (Cline 7) |
| | | T cells control |
| | | T cells treated with synthetic androgen "R1881" |
| | | Total prostate RNA (Cline 1) |
| 4004 | 9627-L1-1 | testes |

REFERENCES

Bartel P., Cell, 116, 281-297, 2004.
Baskerville and al., RNA., Mar.; 11(3):241-7, 2005.
Bejerano G. and al., Bioinformatics, 4; 20 Suppl 1:140-148, 2004.
Bentwich and al., Nat. Genet., Jul.; 37(7):766-70 2005.
Berezikov and al., Cell., Jan. 14; 120(1):21-4, 2005.
Blume and al., Exp Cell Res., 288(1):131-42, 2003.
Brennecke and al., Cell., 113(1):25-36, 2003.
Brennecke and al., PLoS Biol., Mar.; 3(3):e85, 2005.
Burgler and al., BMC Genomics., Jun. 8; 6(1):88, 2005.
Calin and al., Proc Natl Acad Sci, USA, 26; 99(24):15524-9, 2002.
Calin et al., Proc Natl Acad Sci, USA, 10; 101(32):11755-60, 2004.
Calin and al., 2004.
Chen and al., Science, 303(5654):83-6, 2004.
Doench and al., Genes Dev., Mar. 1; 18(5):504-11, Epub, Mar. 10, 2004.
Dostie J, Mourelatos Z, Yang M, Sharma A, Dreyfuss G., "Numerous microRNPs in neuronal cells containing novel microARNs", RNA, 9(2):180-6, 2003. Erratum in: RNA, 9(5):631-2, 2003.
Enright and al., Genome Biol., 5(1):R1, 2003.
Esau and al., J Biol. Chem., 10; 279(50):52361-5, 2004.
Grun D and al., PLoS Comput Biol., Jun.; 1(1):e13, 2005.
He and al., Nat Rev Genet., 5(7):522-31, Review, 2004.
He L. and al., Nature, Jun. 9; 435(7043):828-33, 2005.
Houbaviy and al., Dev Cell. 5(2):351-8, 2003.
Ji and al., Oncogene, 11; 22(39):8031-41, 2003.
John and al., Biochem Biophys Res Commun., 17; 322(2): 403-10, 2004.
Kawasaki and al., Proc Natl Acad Sci, USA, 6; 101(1):360-5, 2004.
Kiriakidou and al., Genes Dev., May 15; 18(10):1165-78, 2004.
Krek and al., Nat Genet, May; 37(5):495-500, 2005.
Krichevsky and al., RNA, 9(10):1274-81, 2003.
Kuwabara, Cell., 19; 116(6):779-93, 2004.
Lai and al., Nat Genet., Apr.; 30(4):363-4, 2002.
Lai and al., Genome Biol., 4(7):R42, 2003.

Lewis and al., Cell., Dec. 26; 115(7):787-98, 2003.
Lewis and al., Cell., Jan. 14; 120(1):15-20, 2005.
Lim and al., Science, Mar. 7; 299(5612):1540, 2003.
Lim and al., Nature, 30, 2005.
Lu and al., Nature, Jun. 9; 435(7043):834-8 2005.
Mattick and al., Bioessays, 25(10):930-9, 2003.
Metzler and al., Genes Chromosomes Cancer, 39(2):167-9, 2004.
Michael and al., Mol Cancer Res., 1(12):882-91, 2003.
Miska and al., Genome Biol., 5(9):R68, 2004.
Muller-Tidow et al., Lung Cancer, 45 Suppl 2:S145-50, 2004.
Nam and al., Nucleic Acids Res., Jun. 24; 33(11):3570-81, 2005.
O'Donnell and al., Nature, Jun. 9; 435(7043):839-43, 2005.
Poy and al., Nature, 11; 432(7014):226-30, 2004.
Rehmsmeier and al., RNA, Oct.; 10(10):1507-17, 2004.
Reinhart and al., Nature, 403(6772):901-6, 2000.
Sempere and al., Genome Biol., 5(3):R13, 2004.
Stark and al., PLoS Biol., Dec.; 1(3):E60, 2003.
Takamizawa J. and al., Cancer Res., 1; 64(11):3753-6, 2004.
Tinzl and al., Trends Genet., 20(12):617-24, 2004, Review.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08116987B2). An electronic copy of the "Sequence Listing" will also be available from the USPTO upon request and payment of the fee set forth in 37 CFR 1.19(b)(3).

The invention claimed is

1. A computer-implemented method of identifying microRNA precursor candidates in non-coding and coding regions of a genome, comprising:
   receiving at least a first and a second genome from two different species, each containing a plurality of sequences including highly repetitive DNA;
   masking a first set of highly repetitive DNA sequences in the first genome, wherein the first set includes SINE and LINE interspersed repeat sequences, but does not include at least 75% of other interspersed repeat sequences;
   masking a second set of highly repetitive DNA sequences in the second genome, wherein the second set includes SINE and LINE interspersed repeat sequences, but does not include at least 75% of the other interspersed repeat sequences;
   comparing the masked first genome to the masked second genome to determine pairs of sequences that are homologous between the two genomes;
   creating a list of microRNA precursor candidates from the homologous pairs; and
   analyzing, with a computer, the list of candidates to:
      eliminate sequences having less than 60 nucleotides; and
      identify sequences that have a stem-loop secondary structure with a 5' strand stem having from 20 to 45 nucleotides and with a 3' strand stem having from 20 to 45 nucleotides; and
      remove, from the list, sequences not having said stem-loop secondary structure, thereby identifying microRNA precursor candidates.

2. The computer-implemented method of claim 1, wherein the other interspersed repeat sequences include processed pseudogenes, retrotranscripts, DNA transposons, and retrovirus retrotransposons.

3. The computer-implemented method of claim 1, further comprising:
   creating a plurality of assemblies, each created from at least one pair of homologous sequences, wherein at least one assembly is created from a first group of at least two pairs of homologous sequences, wherein each pair of the first group has one sequence in common;
   clustering the assemblies into a plurality of clusters, wherein each assembly of a cluster shares at least one sequence with at least one other assembly of that cluster, wherein a cluster includes one or more assemblies;
   analyzing the properties of each cluster to eliminate sequences from the list of candidates.

4. The computer-implemented method of claim 3, further comprising:
   analyzing the properties of each cluster to determine new sequences from the clusters to be added to the first set and second set of sequences that are masked, further comprising:
   adding the new sequences to the first set and to the second set; and
   repeating masking with the first set and to the second set, comparing the masked genomes, creating a plurality of assemblies, and clustering the assemblies.

5. The computer-implemented method of claim 4, wherein analyzing the properties of a cluster to determine new sequences comprises:
   determining the number of sequences of a cluster; and
   if the number of sequences of a cluster is greater than a predetermined number, selecting the sequences of that cluster to be added to the first set and to the second set.

6. The computer-implemented method of claim 3, wherein at least one assembly is created from a second group of at least two pairs of homologous sequences, wherein the two sequences from the first genome of the second group overlap to form a first sequence, wherein the two sequences from the first genome of the second group overlap to form a second sequence, wherein the size variation between the first sequence and the second sequence is less than 10%, and wherein the alignment between the first sequence and the second sequence shows more than 85% sequence similarity.

7. The computer-implemented method of claim 3, wherein at least one assembly is created from a second group of at least two pairs of homologous sequences, wherein the two sequences from the first genome of the second group are consecutive and form a first sequence containing an intervening sequence, wherein the two sequences from the first genome of the second group are consecutive and form a second sequence containing an intervening sequence, wherein the size variation between the first sequence and the second sequence is less than 10%, and wherein the alignment between the first sequence and the second sequence shows more than 90% sequence similarity.

8. The computer-implemented method of claim 3, wherein analyzing the properties of a cluster includes:
if a cluster has more than a predetermined number of sequences, eliminating the sequences of that cluster from the list of candidates.

9. The computer-implemented method of claim 8, wherein the predetermined number is four.

10. The computer-implemented method of claim 8, wherein analyzing the properties of the cluster further includes:
flagging sequences that correspond to a coding gene as 'coding';
eliminating all of the sequences of the cluster if one of the sequences is flagged as 'coding'; and
eliminating the sequences of an assembly if the assembly is not identical by at least 85% within a minimal window of 60 nucleotides.

11. The computer-implemented method of claim 1, wherein analyzing comprises:
eliminating a pair of homologous sequences if a secondary structure resulting from a folding of the sequences does not satisfy each of a first set of criteria including:
a number of nucleotides in a pre-miRNA stem-loop;
a terminal hairpin being of a certain length;
a percentage similarity of the sequences between the two genomes; and
a Z score less than a specified amount; and
eliminating a pair of homologous sequences if a secondary structure resulting from a folding of the sequences does not satisfy a predetermined number of a second set of criteria including:
a minimal free energy (MFE) of less than a specified amount;
a GC content being within a certain percent range;
a base-paring number being within a certain percent range; and
perfect conservation of a sequence of a specified length along arms of the stem-loop.

12. The computer-implemented method of claim 11, wherein the predetermined number is three.

13. The computer-implemented method of claim 11, wherein the first set and the second set of criteria have the following values:
the pre-miRNA stem-loop is between 60 to 120 nucleotides;
the percentage similarity of the sequences between the two genomes is at least 85%;
at least one 17 nt-long sequence is perfectly conserved along the arms of the stem-loop;
the terminal hairpin-loop is between 4 and 15 nucleotides;
the GC content is from 30% to 51%;
the base-pairing number is between 30 and 40%;
the MFE is lower than −25 kcal/mol; and
the Z score is less than 0.06.

14. The computer-implemented method of claim 11, wherein analyzing further comprises:
when a sequence has a secondary structure satisfying the first set of criteria and a predetermined number of the second set of criteria, extracting exact positions of the 5' strand start and exact positions of the 3' strand end to make a new sequence;
folding the new sequence to from a new secondary structure; and
parsing the secondary structure of the new structure to determine if the secondary structure satisfies the first set of criteria and a predetermined number of the second set of criteria.

15. A computer-implemented method of identifying non-coding RNA candidates, comprising:
receiving at least a first and a second genome from two different species, each containing a plurality of sequences including highly repetitive DNA;
masking a first set of highly repetitive DNA sequences in the first genome, wherein the first set includes SINE and LINE interspersed repeat sequences, but does not include at least 75% of other interspersed repeat sequences;
masking a second set of highly repetitive DNA sequences in the second genome, wherein the second set includes SINE and LINE interspersed repeat sequences, but does not include at least 75% of the other interspersed repeat sequences;
comparing the masked first genome to the masked second genome to determine pairs of sequences that are homologous between the two genomes;
creating a list of non-coding RNA candidates from the homologous pairs;
creating a plurality of assemblies, each created from at least one pair of homologous sequences, wherein at least one assembly is created from a first group of at least two pairs of homologous sequences, wherein each pair of the first group has one sequence in common;
clustering the assemblies into a plurality of clusters, wherein each assembly of a cluster shares at least one sequence with at least one other assembly of that cluster, wherein a cluster includes one or more assemblies;
analyzing the properties of each cluster to eliminate sequences from the list of candidates;
analyzing, with a computer, the list of candidates to:
eliminate sequences having less than 60 nucleotides; and
identify sequences that have a stem-loop secondary structure with a 5' strand stem having from 20 to 45 nucleotides and with a 3' strand stem having from 20 to 45 nucleotides; and
remove, from the list, sequences not having said stem-loop secondary structure;
eliminating a pair of homologous sequences if the secondary structure does not satisfy each of a first set of criteria; and
eliminating a pair of homologous sequences if the secondary structure does not satisfy a predetermined number of a second set of criteria, thereby identifying microRNA precursor candidates.

16. A non-transitory computer readable medium storing instructions directing a computer to perform a method of identifying microRNA precursor candidates in non-coding and coding regions of a genome, the instructions comprising:

receiving at least a first and a second genome from two different species, each containing a plurality of sequences including highly repetitive DNA;

masking a first set of highly repetitive DNA sequences in the first genome, wherein the first set includes SINE and LINE interspersed repeat sequences, but does not include at least 75% of other interspersed repeat sequences;

masking a second set of highly repetitive DNA sequences in the second genome, wherein the second set includes SINE and LINE interspersed repeat sequences, but does not include at least 75% of the other interspersed repeat sequences;

comparing the masked first genome to the masked second genome to determine pairs of sequences that are homologous between the two genomes;

creating a list of microRNA precursor candidates from the homologous pairs; and analyzing the list of candidates to:
eliminate sequences having less than 60 nucleotides; and
identify sequences that have a stem-loop secondary structure with a 5' strand stem having from 20 to 45 nucleotides and with a 3' strand stem having from 20 to 45 nucleotides; and
remove, from the list, sequences not having said stem-loop secondary structure, thereby identifying microRNA precursor candidates.

17. The computer readable medium of claim 16, wherein the other interspersed repeat sequences include processed pseudogenes, retrotranscripts, DNA transposons, and retrovirus retrotransposons.

18. The computer readable medium of claim 16, further comprising:
creating a plurality of assemblies, each created from at least one pair of homologous sequences, wherein at least one assembly is created from a first group of at least two pairs of homologous sequences, wherein each pair of the first group has one sequence in common;
clustering the assemblies into a plurality of clusters, wherein each assembly of a cluster shares at least one sequence with at least one other assembly of that cluster, wherein a cluster includes one or more assemblies;
analyzing the properties of each cluster to eliminate sequences from the list of candidates.

19. The computer readable medium of claim 18, further comprising:
analyzing the properties of each cluster to determine new sequences from the clusters to be added to the first set and second set of sequences that are masked, further comprising:
adding the new sequences to the first set and to the second set; and
repeating masking with the first set and to the second set, comparing the masked genomes, creating a plurality of assemblies, and clustering the assemblies.

20. The computer readable medium of claim 19, wherein analyzing the properties of a cluster to determine new sequences comprises:
determining the number of sequences of a cluster; and
if the number of sequences of a cluster is greater than a predetermined number, selecting the sequences of that cluster to be added to the first set and to the second set.

21. The computer readable medium of claim 18, wherein at least one assembly is created from a second group of at least two pairs of homologous sequences, wherein the two sequences from the first genome of the second group overlap to form a first sequence, wherein the two sequences from the first genome of the second group overlap to form a second sequence, wherein the size variation between the first sequence and the second sequence is less than 10%, and wherein the alignment between the first sequence and the second sequence shows more than 85% sequence similarity.

22. The computer readable medium of claim 18, wherein at least one assembly is created from a second group of at least two pairs of homologous sequences, wherein the two sequences from the first genome of the second group are consecutive and form a first sequence containing an intervening sequence, wherein the two sequences from the first genome of the second group are consecutive and form a second sequence containing an intervening sequence, wherein the size variation between the first sequence and the second sequence is less than 10%, and wherein the alignment between the first sequence and the second sequence shows more than 90% sequence similarity.

23. The computer readable medium of claim 18, wherein analyzing the properties of a cluster includes:
if a cluster has more than a predetermined number of sequences, eliminating the sequences of that cluster from the list of candidates.

24. The computer readable medium of claim 23, wherein the predetermined number is four.

25. The computer readable medium of claim 23, wherein analyzing the properties of the cluster further includes:
flagging sequences that correspond to a coding gene as 'coding';
eliminating all of the sequences of the cluster if one of the sequences is flagged as 'coding'; and
eliminating the sequences of an assembly if the assembly is not identical by at least 85% within a minimal window of 60 nucleotides.

26. The computer readable medium of claim 16, wherein analyzing comprises:
eliminating a pair of homologous sequences if a secondary structure resulting from a folding of the sequences does not satisfy each of a first set of criteria including:
a number of nucleotides in a pre-miRNA stem-loop;
a terminal hairpin being of a certain length;
a percentage similarity of the sequences between the two genomes; and
a Z score less than a specified amount; and
eliminating a pair of homologous sequences if a secondary structure resulting from a folding of the sequences does not satisfy a predetermined number of a second set of criteria including:
a minimal free energy (MFE) of less than a specified amount;
a GC content being within a certain percent range;
a base-paring number being within a certain percent range; and
perfect conservation of a sequence of a specified length along arms of the stem-loop.

27. The computer readable medium of claim 26, wherein the predetermined number is three.

28. The computer readable medium of claim 26, wherein the first set and the second set of criteria have the following values:
the pre-miRNA stem-loop is between 60 to 120 nucleotides;
the percentage similarity of the sequences between the two genomes is at least 85%;
at least one 17 nt-long sequence is perfectly conserved along the arms of the stem-loop;
the terminal hairpin-loop is between 4 and 15 nucleotides;

the GC content is from 30% to 51%;
the base-pairing number is between 30 and 40%;
the MFE is lower than −25 kcal/mol; and
the Z score is less than 0.06.

29. The computer readable medium of claim 26, wherein analyzing further comprises:
when a sequence has a secondary structure satisfying the first set of criteria and a predetermined number of the second set of criteria, extracting exact positions of the 5' strand start and exact positions of the 3' strand end to make a new sequence;
folding the new sequence to from a new secondary structure; and
parsing the secondary structure of the new structure to determine if the secondary structure satisfies the first set of criteria and a predetermined number of the second set of criteria.

* * * * *